US007642400B2

(12) United States Patent
Fields et al.

(10) Patent No.: US 7,642,400 B2
(45) Date of Patent: Jan. 5, 2010

(54) PROTEIN KINASE C IOTA

(75) Inventors: Alan P. Fields, Jacksonville, FL (US); Nicole Renee Murray, Ponte Vedra Beach, FL (US); Melody Lee Stallings-Mann, Jacksonville, FL (US); Lee Jamieson, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/592,289

(22) PCT Filed: Mar. 8, 2005

(86) PCT No.: PCT/US2005/007935

§ 371 (c)(1),
(2), (4) Date: Jul. 23, 2007

(87) PCT Pub. No.: WO2005/086909

PCT Pub. Date: Sep. 22, 2005

(65) Prior Publication Data

US 2007/0283451 A1 Dec. 6, 2007

Related U.S. Application Data

(60) Provisional application No. 60/551,288, filed on Mar. 8, 2004.

(51) Int. Cl.
*A01K 67/027* (2006.01)
*G01K 33/00* (2006.01)
*C12N 15/00* (2006.01)
*C12N 5/00* (2006.01)

(52) U.S. Cl. .................. 800/18; 800/3; 800/8; 435/325
(58) Field of Classification Search .............. 800/8, 800/18, 3; 435/325
See application file for complete search history.

(56) References Cited

U.S. PATENT DOCUMENTS 4,873,191 A 10/1989 Wagner et al.

OTHER PUBLICATIONS

Murray (J. Cell Biology, vol. 145, No. 4, May 17, 1999, 699-711).*
Yu (2001, Oncogene, vol. 20, p. 4777-4792).*
GenBank Accession No. NM_033360 dated Apr. 15, 2007, 6 pages.
Adjei, "Blocking Oncogenic Ras Signaling for Cancer Therapy," *J. Natl. Cancer Inst.*, 2001, 93(14):1062-1074.
Bos, "*ras* Oncogenes in Human Cancer: A Review," *Cancer Res.*, 1989, 49:4682-4689.
Choi et al., "Expression of the PKC epsilon in the brain controls ethanol-drinking behavior," *Soc. Neurosci. Abstracts*, 2001, 27(1):1495 (see abstract).
Cibelli et al., "Cloned Transgenic Calves Produced from Nonquiescent Fetal Fibroblasts," *Science*, 1998, 280:1256-1258.
Coghlan et al., "Atypical Protein Kinases Cλ and -ξ Associate with the GTP-Binding Protein Cdc42 and Mediate Stress Fiber Loss," *Mol. Cell. Biol.*, 2000, 20(8):2880-2889.
De Corte et al., "Gelsolin-induced epithelial cell invasion is dependent on Ras-Rac signaling," *EMBO J.*, 2002, 21(24):6781-6790.
Fujimoto et al., "Transforming Growth Factor-β1 Promotes Invasiveness after Cellular Transformation with Activated Ras in Intestinal Epithelial Cells," *Exp. Cell Res.*, 2001, 266:239-249.
Glasser et al., "Human *SP-C* gene sequences that confer lung epithelium-specific expression in transgenic mice," *Am. J. Physiol. Lung Cell Mol. Physiol.*, 2000, 278:L933-L945.
Gökmen-Polar et al., "Elevated Protein Kinase C αII Is an Early Promotive Event in Colon Carcinogenesis," *Cancer Res.*, 2001, 61:1375-1381.
Guatelli et al., "Isothermal, in vitro amplification of nucleic acids by a multienzyme reaction modeled after retroviral replication," *Proc. Natl. Acad. Sci. USA*, 1990, 87:1874-1878.
Huang et al., "Inhibition of Atypical PKC Blocks Ultraviolet-Induced AP-1 Activation by Specifically Inhibiting ERKs Activation," *Mol. Carcinogenesis*, 2000, 27:65-75.
Huang et al., "Ultraviolet B-induced Activated Protein-1 Activation Does Not Require Epidermal Growth Factor Receptor but Is Blocked by a Dominant Negative PKCλ/ι," *J. Biol. Chem.*, 1996, 271(49):31262-31268.
Igarashi et al., "Ksp-cadherin gene promoter. II. Kidney-specific activity in transgenic mice," *Am. J. Physiol.*, 1999, 277:F599-F610.
Ireton et al., "A novel role for p120 catenin in E-cadherin function," *J. Cell Biol.*, 2002, 159(3):465-476.
Jamieson et al., "Protein Kinase Cι Activity Is Necessary for Bcr-Abl-mediated Resistance to Drug-induced Apoptosis," *J. Biol. Chem.*, 1999, 274(7):3927-3930.
Jansen et al., "Relation of the induction of epidermal ornithine decarboxylase and hyperplasia to the different skin tumor-promotion susceptibilities of protein kinase Cα, -δ and -ε transgenic mice," *Int. J. Cancer*, 2001, 93:635-643.
Johnson et al., "Somatic activation of the *K-ras* oncogene causes early onset lung cancer in mice," *Nature*, 2001, 410:1111-1116.
Kampfer et al., "Protein Kinase C Isoforms Involved in the Transcriptional Activation of Cyclin D1 by Transforming Ha-Ras," *J. Biol. Chem.*, 2001, 276(46):42834-42842.
Khosravi-Far et al., "Activation of Rac1, RhoA, and Mitogen-Activated Protein Kinases Is Required for Ras Transformation," *Mol. Cell. Biol.*, 1995, 15(11):6443-6453.
Ko et al., "TGF-β1 effects on proliferation of rat intestinal epithelial cells are due to inhibition of cyclin D1 expression," *Oncogene*, 1998, 16:3445-3454.
Lewis, "PCR's Competitors Are Alive and Well and Moving Rapidly Towards Commercialization," *Genetic Engineering News*, 1992, 12:1-3.
Lo, "Transformation by Iontophoretic Microinjection of DNA: Multiple Integrations Without Tandem Insertions," *Mol. Cell. Biol.*, 1983, 3(10):1803-1814.

(Continued)

*Primary Examiner*—Michael C. Wilson
(74) *Attorney, Agent, or Firm*—Fish & Richardson P.C.

(57) ABSTRACT

The invention involves PKCι signaling. The invention provides, for example, transgenic animals, inhibitors of PKCι signaling, methods for inhibiting PKCι signaling, methods for identifying inhibitors of PKCι signaling, and methods for diagnosing cancer.

9 Claims, 21 Drawing Sheets

OTHER PUBLICATIONS

Lu et al., NF-κB/RelA transactivation is required for atypical protein kinase Cι-mediated cell survival, *Oncogene*, 2001, 20:4777-4792.

Magnuson et al., "Ability of Aberrant Crypt Foci Characteristics to Predict Colonic Tumor Incidence in Rats Fed Cholic Acid," *Cancer Res.*, 1993, 53:4499-4504.

Masumori et al., "A Probasin-Large T Antigen Transgenic Mouse Line Develops Prostate Adenocarcinoma and Neuroendocrine Carcinoma with Metastatic Potential," *Cancer Res.*, 2001, 61:2239-2249.

McLellan et al., "Dose response and proliferative characteristics of aberrant crypt foci: putative preneoplastic lesions in rat colon," *Carcinogenesis*, 1991, 12(11):2093-2098.

McLellan et al., "Sequential Analyses of the Growth and Morphological Characteristics of Aberrant Crypt Foci: Putative Preneoplastic Lesions," *Cancer Res.*, 1991, 51:5270-5274.

Murray and Fields, "Atypical Protein Kinase C ι Protects Human Leukemia Cells against Drug-induced Apoptosis," *J. Biol. Chem.*, 1997, 272(44):27521-27524.

Murray et al., "Overexpression of Protein Kinase C $β_{II}$ Induces Colonic Hyperproliferation and Increased Sensitivity to Colon Carcinogenesis," *J. Cell Biol.*, 1999, 145(4):699-711.

Murray et al., "Protein kinase C βII and TGFβRII in ω-3 fatty acid-mediated inhibition of colon carcinogenesis," *J. Cell Biol.*, 2002, 157(6):915-920.

Murray et al., "Protein kinase Cι is required for Ras transformation and colon carcinogenesis in vivo," *J. Cell Biol.*, 2004, 164(6):797-802.

Noda et al., "Human homologues of the *Caenorhabditis elegans* cell polarity protein PAR6 as an adaptor that links the small GTPases Rac and Cdc42 to atypical protein kinase C," *Genes to Cells*, 2001, 6:107-119.

Perander et al., "Nuclear Import and Export Signals Enable Rapid Nucleocytoplasmic Shuttling of the Atypical Protein Kinase C λ," *J. Biol. Chem.*, 2001, 276(16):13015-13024.

Pinkert et al., "An albumin enhancer located 10 kb upstream functions along with its promoter to direct efficient, liver-specific expression in transgenic mice," *Genes Dev.*, 1987, 1:268-276.

Pretlow et al., "K-ras Mutations in Putative Preneoplastic Lesions in Human Colon," *J. Natl. Cancer Inst.*, 1993, 85(24):2004-2007.

Qiu et al., "An essential role for Rac in Ras transformation," *Nature*, 1995, 374:457-459.

Sakai et al., "Brain region specific and inducible PKC-GFP transgenic mice as a tool for analysing PKC functions in central nervous system," *Soc. Neurosci. Abstracts*, 2003, Abstract No. 162.12.

Sakai et al., "Development of brain region specific and tet-regulated PKC-GFP transgenic mice as a tool for analysing PKC functions in central nervous system," *Soc. Neurosci. Abstracts*, 2001, 27(1):110.

Sambrook et al., *Molecular Cloning, A Laboratory Manual*, 1989, second edition, sections 9.37-9.52, Cold Spring Harbor Press, Plainview, NY.

Sander et al., "Matrix-dependent Tiam1/Rac Signaling in Epithelial Cells Promotes Either Cell-Cell Adhesion or Cell Migration and Is Regulated by Phosphatidylinositol 3-Kinase," *J. Cell Biol.*, 1998, 143(5):1385-1398.

Sheng et al., "Transforming Growth Factor-β1 Enhances Ha-*ras*-induced Expression of Cyclooxygenase-2 in Intestinal Epithelial Cells via Stabilization of mRNA," *J. Biol. Chem.*, 2000, 275(9):6628-6635.

Shi et al., "Brain-specific expression of an exogenous gene after i.v. administration," *Proc. Natl. Acad. Sci. USA*, 2001, 98(22):12754-12759.

Shivapurkar et al., "K-*ras* and *p53* mutations in aberrant crypt foci and colonic tumors from colon cancer patients," *Cancer Lett.*, 1997, 115:39-46.

Simon et al., "Suppressor and Activator Functions Mediated by a Repeated Heptad Sequence in the Liver Fatty Acid-binding Protein Gene (*Fabpl*). Effects on renal, small intestinal, and colonic epithelial cell gene expression in transgenic mice," *J. Biol. Chem.*, 1997, 272(16):10652-10663.

Suzuki et al., "aPKC kinase activity is required for the asymmetric differentiation of the premature junctional complex during epithelial cell polarization," *J. Cell Sci.*, 2002, 115:3565-3573.

Suzuki et al., "Protein Kinase C λ/ι (PCKλ/ι): A PKC Isotype Essential for the Development of Multicellular Organisms," *J. Biochem.*, 2003, 133:9-16.

Takayama et al., "Aberrant crypt foci of the colon as precursors of adenoma and cancer," *N. Engl. J. Med.*, 1998, 339:1277-1284.

Tessier et al., "Mammary Tumor Induction in Transgenic Mice Expressing an RNA-Binding Protein," *Cancer Res.*, 2004, 64:209-214.

Thompson et al., "Germ Line Transmission and Expression of a Corrected HPRT Gene Produced by Gene Targeting in Embryonic Stem Cells," *Cell* 1989, 56:313-321.

Überall et al., "Evidence That Atypical Protein Kinase C-λ and Atypical Protein Kinase C-ξ Participate in Ras-mediated Reorganization of the F-actin Cytoskeleton," *J. Cell Biol.*, 1999, 144(3):413-425.

Van der Putten et al., "Efficient insertion of genes into the mouse germ line via retroviral vectors," *Proc. Natl. Acad. Sci. USA*, 1985, 82:6148-6152.

Wakayama et al., "Full-term development of mice from enucleated oocytes injected with cumulus cell nuclei," *Nature*, 1998, 394:369-374.

Walsh and Bar-Sagi, "Differential Activation of the Rac Pathway by Ha-Ras and K-Ras," *J. Biol. Chem.*, 2001, 276(19):15609-15615.

Weiss, "Hot Prospect for New Gene Amplifier," *Science*, 1991, 254:1292-1293.

White et al., "Phosphorylation of Tyrosine 256 Facilitates Nuclear Import of Atypical Protein Kinase C," *J. Cell. Biochem.*, 2002, 85:42-53.

Wilmut et al., "Viable offspring derived from fetal and adult mammalian cells," *Nature*, 1997, 385:810-813.

Wooten et al., "Nerve Growth Factor Stimulates Multisite Tyrosine Phosphorylation and Activation of the Atypical Protein Kinase C's via a src Kinase Pathway," *Mol. Cell. Biol.*, 2001, 21(24):8414-8427.

Yasuda et al., "Identification of Novel Pancreas-specific Regulatory Sequences in the Promoter Region of Human Pancreatic Secretory Trypsin Inhibitor Gene," *J. Biol. Chem.*, 1998, 273(51):34413-34421.

Yu et al., "Role of Cyclooxygenase 2 in Protein Kinase C βII-mediated Colon Carcinogenesis," *J. Biol. Chem.*, 2003, 278(13):11167-11174.

Zaidi et al., "Transgenic expression of human *MGMT* protects against azoxymethane-induced aberrant crypt foci and G to A mutations in the K-*ras* oncogene of mouse colon," *Carcinogenesis*, 1995, 16(3):451-456.

* cited by examiner

Figure 6

```
                                        atgtcc cacacggtcg caggcggcgg cagcggggac
cattcccacc aggtccgggt gaaagcctac taccgcgggg atatcatgat aacacatttt
gaaccttcca tctcctttga gggcctttgc aatgaggttc gagacatgtg ttcttttgac
aacgaacagc tcttcaccat gaaatggata gatgaggaag gagacccgtg tacagtatca
tctcagttgg agttagaaga agcctttaga ctttatgagc taaacaagga ttctgaactc
ttgattcatg tgttcccttg tgtaccagaa cgtcctggga tgccttgtcc aggagaagat
aaatccatct accgtagagg tgaacgccgc tggagaaagc tttattgtgc caatggccac
actttccaag ccaagcgttt caacaggcgt gctcactgtg ccatctgcac agaccgaata
tggggacttg gacgccaagg atataagtgc atcaactgca aactcttggt tcataagaag
tgccataaac tcgtcacaat gaatgtggg cggcattctt tgccacagga accagtgatg
cccatggatc agtcatccat gcattctgac catgcacaga cagtaattcc atataatcct
tcaagtcatg agagtttgga tcaagttggt gaagaaaaag aggcaatgaa caccagggaa
agtggcaaag cttcatccag tctaggtctt caggattttg atttgctccg ggtaatagga
agaggaagtt atgccaaagt actgttggtt cgattaaaaa aaacagatcg tatttatgca
atgaaagttg tgaaaaaga gcttgttaat gatgatgagg atattgattg ggtacagaca
gagaagcatg tgtttgagca ggcatccaat catcctttcc ttgttgggct gcattcttgc
tttcagacag aaagcagatt gttctttgtt atagagtatg taaatggagg agacctaatg
tttcatatgc agcgacaaag aaaacttcct gaagaacatg ccagatttta ctctgcagaa
atcagtctag cattaaatta tcttcatgag cgagggataa tttatagaga tttgaaactg
gacaatgtat tactggactc tgaaggccac attaaactca ctgactacgg catgtgtaag
gaaggattac ggccaggaga taaccagc actttctgtg gtactcctaa ttacattgct
cctgaaattt taagaggaga agattatggt ttcagtgttg actggtgggc tcttggagtg
ctcatgtttg agatgatggc aggaaggtct ccatttgata ttgttgggag ctccgataac
cctgaccaga acacagagga ttatctcttc caagttattt tggaaaaaca aattcgcata
ccacgttctc tgtctgtaaa agctgcaagt gttctgaaga gtttcttaa taaggaccct
aaggaacgat tgggttgtca tcctcaaaca ggatttgctg atattcaggg cacccgttc
ttccgaaatg ttgattggga tatgatggag caaaaacagg tggtacctcc ctttaaacca
aatatttctg gggaatttgg tttggacaac tttgattctc agtttactaa tgaacctgtc
cagctcactc cagatgacga tgacattgtg aggaagattg atcagtctga atttgaaggt
tttgagtata tcaatcctct tttgatgtct gcagaagaat gtgtctga (SEQ ID NO:1)
```

MSHTVAGGGSGDHSHQVRVKAYYRGDIMITHFEPSISFEGLCNEVRDMCSFDNEQLFTMKWIDEEGDPC
TVSSQLELEEAFRLYELNKDSELLIHVFPCVPERPGMPCPGEDKSIYRRG<u>E</u>RRWRKLYCANGHTFQAKR
FNRRAHCAICTDRIWGLGRQGYKCINCKLLVHKKCHKLVTIECGRHSLPQEPVMPMDQSSMHSDHAQTV
IPYNPSSHESLDQVGEEKEAMNTRESGKASSSLGLQDFDLLRVIGRGSYAKVLLVRLKKTDRIYAMKVV
KKELVNDDEDIDWVQTEKHVFEQASNHPFLVGLHSCFQTESRLFFVIEYVNGGDLMFHMQRQRKLPEEH
ARFYSAEISLALNYLHERGIIYRDLKLDNVLLDSEGHIKLTDYGMCKEGLRPGDTTSTFCGTPNYIAPE
ILRGEDYGFSVDWWALGVLMFEMMAGRSPFDIVGSSDNPDQNTEDYLFQVILEKQIRIPRSLSVKAASV
LKSFLNKDPKERLGCHPQTGFADIQGHPFFRNVDWDMMEQKQVVPPFKPNISGEFGLDNFDSQFTNEPV
QLTPDDDDIVRKID
QSEFEGFEYINPLLMSAEECV (SEQ ID NO:2)

Figure 7

```
                              atgtcc cacacggtcg caggcggcgg cagcggggac
cattcccacc aggtccgggt gaaagcctac taccgcgggg atatcatgat aacacatttt
gaaccttcca tctcctttga gggcctttgc aatgaggttc gagacatgtg ttcttttgac
aacgaacagc tcttcaccat gaaatggata gatgaggaag gagacccgtg tacagtatca
tctcagttgg agttagaaga agcctttaga ctttatgagc taaacaagga ttctgaactc
ttgattcatg tgttcccttg tgtaccagaa cgtcctggga tgccttgtcc aggagaagat
aaatccatct accgtagagg tgcacgccgc tggagaaagc tttattgtgc caatggccac
actttccaag ccaagcgttt caacaggcgt gctcactgtg ccatctgcac agaccgaata
tggggacttg gacgccaagg atataagtgc atcaactgca aactcttggt tcataagaag
tgccataaac tcgtcacaat tgaatgtggg cggcattctt gccacagga accagtgatg
cccatggatc agtcatccat gcattctgac catgcacaga cagtaattcc atataatcct
tcaagtcatg agagtttgga tcaagttggt gaagaaaaag aggcaatgaa caccagggaa
agtggcaaag cttcatccag tctaggtctt caggattttg atttgctccg ggtaatagga
agaggaagtt atgccaaagt actgttggtt cgattaaaaa aaacagatcg tatttatgca
atgtggttg tgaaaaaga gcttgttaat gatgatgagg atattgattg ggtacagaca
gagaagcatg tgtttgagca ggcatccaat catcctttcc ttgttgggct gcattcttgc
tttcagacag aaagcagatt gttcttttgtt atagagtatg taaatggagg agacctaatg
tttcatatgc agcgacaaag aaaacttcct gaagaacatg ccagatttta ctctgcagaa
atcagtctag cattaaatta tcttcatgag cgaggataa tttatagaga tttgaaactg
gacaatgtat tactggactc tgaaggccac attaaactca ctgactacgg catgtgtaag
gaaggattac ggccaggaga tacaaccagc actttctgtg gtactcctaa ttacattgct
cctgaaattt taagaggaga agattatggt ttcagtgttg actggtgggc tcttggagtg
ctcatgtttg agatgatggc aggaaggtct ccatttgata ttgttgggag ctccgataac
cctgaccaga acacagagga ttatctcttc caagttattt tggaaaaaca aattcgcata
ccacgttctc tgtctgtaaa agctgcaagt gttctgaaga gtttttcttaa taaggaccct
aaggaacgat tgggttgtca tcctcaaaca ggatttgctg atattcaggg acaccccgttc
ttccgaaatg ttgattggga tatgatggag caaaaacagg tggtacctcc ctttaaacca
aatatttctg gggaatttgg tttggacaac tttgattctc agtttactaa tgaacctgtc
cagctcactc cagatgacga tgacattgtg aggaagattg atcagtctga atttgaaggt
tttgagtata tcaatcctct tttgatgtct gcagaagaat gtgtctga  (SEQ ID NO:3)
```

MSHTVAGGGSGDHSHQVRVKAYYRGDIMITHFEPSISFEGLCNEVRDMCSFDNEQLFTMKWIDEEGDPC
TVSSQLELEEAFRLYELNKDSELLIHVFPCVPERPGMPCPGEDKSIYRRGARRWRKLYCANGHTFQAKR
FNRRAHCAICTDRIWGLGRQGYKCINCKLLVHKKCHKLVTIECGRHSLPQEPVMPMDQSSMHSDHAQTV
IPYNPSSHESLDQVGEEKEAMNTRESGKASSSLGLQDFDLLRVIGRGSYAKVLLVRLKKTDRIYAMWVV
KKELVNDDEDIDWVQTEKHVFEQASNHPFLVGLHSCFQTESRLFFVIEYVNGGDLMFHMQRQRKLPEEH
ARFYSAEISLALNYLHERGIIYRDLKLDNVLLDSEGHIKLTDYGMCKEGLRPGDTTSTFCGTPNYIAPE
ILRGEDYGFSVDWWALGVLMFEMMAGRSPFDIVGSSDNPDQNTEDYLFQVILEKQIRIPRSLSVKAASV
LKSFLNKDPKERLGCHPQTGFADIQGHPFFRNVDWDMMEQKQVVPPFKPNISGEFGLDNFDSQFTNEPV
QLTPDDDDIVRKIDQSEFEGFEYINPLLMSAEECV  (SEQ ID NO:4)

PROTEIN KINASE C IOTA

CROSS-REFERENCE TO RELATED APPLICATIONS

This application is a National Stage application under 35 U.S.C. §371 and claims benefit under 35 U.S.C. §119(a) of International Application No. PCT/US2005/007935 having an International Filing Date of Mar. 8, 2005, which claims the benefit of U.S. Provisional Application Serial No. 60/551,288, filed Mar. 8, 2004.

STATEMENT AS TO FEDERALLY SPONSORED RESEARCH

This invention was made with government support under 5R01CA081436-09 and 5R01CA094122-06 awarded by The National Institutes of Health National Cancer Institute. The government has certain rights in the invention.

STATEMENT AS TO FEDERALLY SPONSORED RESEARCH

Funding for the work described herein was provided by the federal government, which may have certain rights in the invention.

BACKGROUND

1. Technical Field

The invention relates to methods and materials involved in protein kinase C iota signaling. The invention also relates to transgenic animals, inhibitors of protein kinase C iota signaling, methods for inhibiting protein kinase C iota signaling, methods for identifying inhibitors of protein kinase C iota signaling, and methods for diagnosing cancer.

2. Background Information

Protein kinase C iota (PKC iota or PKCι) plays a requisite role in Bcr-Abl mediated resistance to chemotherapy-induced apoptosis (Jamieson et al., *J. Biol. Chem.*, 274:3927-3930 (1999) and Murray et al., *J. Biol. Chem.*, 272:27521-4 (1997)), and is critical for epithelial cell polarity (Suzuki et al., *J. Cell Sci.*, 115:3565-73 (2002)) and cell survival (Jamieson et al., *J. Biol. Chem.*, 274:3927-3930 (1999) and Murray et al., *J. Biol. Chem.*, 272:27521-4 (1997)). PKCι has also been implicated in Ras-mediated signaling (Coghlan et al., *Mol. Cell. Biol.*, 20:2880-9 (2000); Kampfer et al, *J. Biol. Chem.*, 276:42834-42 (2001); and Uberall et al 1., *J. Cell Biol.*, 144:413-25 (1999)). Activating Ras mutations occur in about 30 percent of all human cancers (Adjei, *J. Natl. Cancer Inst.*, 93:1062-74 (2001)), and in about 50 percent of human colon adenomas and carcinomas (Bos, *Cancer Res.*, 49:4682-9 (1989)). Ras mutations are an early event in colon carcinogenesis and are often present in preneoplastic lesions in the colon (Pretlow et al., *J. Natl. Cancer Inst.*, 85:2004-7 (1993) and Zaidi et al, *Carcinogenesis.*, 16:451-6 (1995)).

SUMMARY

The invention involves PKCι signaling. The invention relates to transgenic animals, inhibitors of PKCι signaling, methods for inhibiting PKCι signaling, methods for identifying inhibitors of PKCι signaling, and methods for diagnosing cancer. As described herein, Ras-mediated transformation, invasion, and anchorage-independent growth of cells (e.g., intestinal epithelial cells) requires PKCι activity. In addition, PKCι is involved in Ras- and carcinogen-mediated colon carcinogenesis in vivo. PKCι also is involved in other cancers including, without limitation, lung cancers. For example, transgenic mice expressing constitutively active PKCι (caPKCι) in the colon are highly susceptible to carcinogen-induced colon carcinogenesis, whereas mice expressing kinase-deficient PKCι (kdPKCι) are resistant to both carcinogen- and oncogenic Ras-mediated carcinogenesis. Expression of kdPKCι in Ras-transformed rat intestinal epithelial (RIE/Ras) cells blocks oncogenic Ras-mediated activation of Rac1, cellular invasion, and anchorage-independent growth. Constitutively active Rac1 (RacV12) restores invasiveness and anchorage-independent growth in RIE/Ras cells expressing kdPKCι. These results demonstrate that PKCι is required for oncogenic Ras- and carcinogen-mediated carcinogenesis (e.g., colon carcinogenesis) in vivo and define a pro-carcinogenic signaling axis consisting of Ras, PKCι, and Rac1.

In general, the invention features a transgenic rodent, the nucleated cells of which contain a transgene, the transgene containing a promoter sequence operably linked to a nucleic acid sequence encoding a protein kinase C iota polypeptide, wherein the transgenic rodent expresses the protein kinase C iota polypeptide and develops more preneoplastic colonic lesions after azoxymethane treatment than a corresponding wild-type rodent treated with the azoxymethane. The transgenic rodent can be a mouse. The protein kinase C iota polypeptide can be a constitutively active protein kinase C iota polypeptide. The promoter sequence can promote expression in a cell from the colonic epithelium. The promoter sequence can contain a sequence present in a liver fatty acid-binding protein gene. The promoter sequence can be an $Fabpl^{4\times\,at\,-132}$ promoter sequence.

In another embodiment, the invention features a transgenic rodent, the nucleated cells of which contain a transgene, the transgene containing a promoter sequence operably linked to a nucleic acid sequence encoding a protein kinase C iota polypeptide lacking protein kinase C iota activity, wherein the transgenic rodent expresses the protein kinase C iota polypeptide and exhibits less protein kinase C iota activity in the colonic epithelium than a corresponding wild-type rodent. The transgenic rodent can be a mouse. The promoter sequence can promote expression in a cell from the colonic epithelium. The promoter sequence can contain a sequence present in a liver fatty acid-binding protein gene. The promoter sequence can be a $Fabpl^{4\times\,at\,-132}$ promoter sequence. The nucleated cells can contain a second transgene, the second transgene containing a second promoter sequence operably linked to a second nucleic acid sequence encoding a ras polypeptide. The ras polypeptide can be a K-Ras polypeptide. The transgenic rodent can develop fewer aberrant crypt foci in the proximal colon than a corresponding rodent with nucleated cells containing the second transgene and lacking the transgene. The transgenic rodent can be a $K-Ras^{L A2}$/kdPKCι mouse.

In another aspect, the invention features progeny of a transgenic rodent, wherein the nucleated cells of the transgenic rodent contain a transgene, the transgene containing (a) a promoter sequence operably linked to a nucleic acid sequence encoding a protein kinase C iota polypeptide, wherein the transgenic rodent expresses the protein kinase C iota polypeptide and develops more preneoplastic colonic lesions after azoxymethane treatment than a corresponding wild-type rodent treated with the azoxymethane, or (b) a promoter sequence operably linked to a nucleic acid sequence encoding a protein kinase C iota polypeptide lacking protein kinase C iota activity, wherein the transgenic rodent expresses the protein kinase C iota polypeptide and exhibits less protein kinase C iota activity in the colonic epithelium than a corresponding wild-type rodent. The nucleated cells of the progeny contain the transgene.

In another aspect, the invention features an isolated cell of a transgenic rodent wherein the nucleated cells of the transgenic rodent contain a transgene, the transgene containing (a) a promoter sequence operably linked to a nucleic acid sequence encoding a protein kinase C iota polypeptide, wherein the transgenic rodent expresses the protein kinase C iota polypeptide and develops more preneoplastic colonic lesions after azoxymethane treatment than a corresponding wild-type rodent treated with the azoxymethane, or (b) a promoter sequence operably linked to a nucleic acid sequence encoding a protein kinase C iota polypeptide lacking protein kinase C iota activity, wherein the transgenic rodent expresses the protein kinase C iota polypeptide and exhibits less protein kinase C iota activity in the colonic epithelium than a corresponding wild-type rodent.

In another aspect, the invention features a method for inhibiting a protein kinase C iota polypeptide response in a mammal. The method includes administering an inhibitor to the mammal under conditions wherein the response is inhibited, wherein the inhibitor reduces the interaction between a protein kinase C iota polypeptide and a polypeptide selected from the group consisting of Par-6, Src, Par-4, p62/ZIP, and Par-3 polypeptides. The response can be cell transformation, development of cancer, and/or colon carcinogenesis. The inhibitor can be a polypeptide fragment. The polypeptide fragment can contain an amino acid sequence present in the protein kinase C iota polypeptide. The inhibitor can be aurothioglucose, aurothiomaleate, thimerosal, phenylmercuric acetate, ebselen, cisplatin, apomorphine, pyrantel pamoate, gossypol-acetic acid complex, ellagic acid, or hexestrol.

In another aspect, the invention features a method for identifying an agent that inhibits transformation of a cell. The method includes (a) administering a test agent and a carcinogen to a transgenic rodent, the nucleated cells of which contain a transgene containing a promoter sequence operably linked to a nucleic acid sequence encoding a protein kinase C iota polypeptide, wherein the transgenic rodent expresses the protein kinase C iota polypeptide and develops more preneoplastic colonic lesions after azoxymethane treatment than a corresponding wild-type rodent treated with the azoxymethane, and (b) determining if the test agent inhibits cell transformation in the transgenic rodent as compared with a corresponding transgenic rodent to which the test agent has not been administered. The cell can be an intestinal cell. The test agent can be a test polypeptide. The test polypeptide can contain an amino acid sequence present in a protein kinase C iota polypeptide. The protein kinase C iota polypeptide can be a constitutively active protein kinase C iota polypeptide. The carcinogen can be azoxymethane or dimethylhydrazine.

In another aspect, the invention features a method for identifying an agent that inhibits the interaction between a protein kinase C iota polypeptide and a polypeptide selected from the group consisting of Par-6, Src, Par-4, p62/ZIP, and Par-3 polypeptides. The method includes (a) contacting a test agent with the protein kinase C iota polypeptide and the polypeptide, wherein the protein kinase C iota polypeptide and the polypeptide each contain a fluorescent molecule under conditions wherein fluorescent resonance energy transfer is detectable when the protein kinase C iota polypeptide interacts with the polypeptide, and (b) determining whether or not the presence of the test agent reduced fluorescent resonance energy transfer between the protein kinase C iota polypeptide and the polypeptide as compared to the fluorescent resonance energy transfer observed between the protein kinase C iota polypeptide and the polypeptide in the absence of the test agent, wherein a reduction is the fluorescent resonance energy transfer observed between the protein kinase C iota polypeptide and the polypeptide in the presence of the test agent indicates that the test agent is the agent. The polypeptide can be a Par-6 polypeptide. The test agent can be a test polypeptide. The test polypeptide can contain an amino acid sequence present in a protein kinase C iota polypeptide. The test agent can be aurothioglucose, aurothiomaleate, thimerosal, phenylmercuric acetate, ebselen, cisplatin, apomorphine, pyrantel pamoate, gossypol-acetic acid complex, ellagic acid, or hexestrol.

In another aspect, the invention features a method for determining whether or not a mammal is developing cancerous cells. The method includes determining whether or not the mammal contains an elevated level of a protein kinase C iota polypeptide, wherein the presence of the elevated level of the protein kinase C iota polypeptide indicates that the mammal is developing cancerous cells. The cells can be intestinal cells. The mammal can be a human.

In another aspect, the invention features a transgenic rodent, the nucleated cells of which contain a transgene. The transgene contains a promoter sequence operably linked to a nucleic acid sequence encoding a protein kinase C iota polypeptide, where the transgenic rodent is capable of expressing the protein kinase C iota polypeptide in lung tissue. The a promoter sequence can be an inducible promoter sequence. The protein kinase C iota polypeptide can be a kinase-deficient protein kinase C iota polypeptide. The carcinogen can be N-nitroso-tris-chloroethylurea. The transgenic rodent can develop more cancerous lesions after carcinogen treatment or expression of a ras polypeptide than a comparable rodent lacking said transgene.

In another aspect, the invention features a method for inhibiting the binding of a protein kinase C iota polypeptide to a Par-6 polypeptide. The method includes contacting the protein kinase C iota polypeptide or the Par-6 polypeptide with a protein kinase C iota polypeptide/Par-6 polypeptide inhibitor. The protein kinase C iota polypeptide/Par-6 polypeptide inhibitor can be aurothioglucose, aurothiomaleate, thimerosal, phenylmercuric acetate, ebselen, cisplatin, apomorphine, pyrantel pamoate, gossypol-acetic acid complex, ellagic acid, or hexestrol.

In another aspect, the invention features a method for assessing the prognosis of a mammal (e.g., human) having lung cancer. The method includes determining whether or not the mammal contains cancer cells having an increased copy number of nucleic acid encoding a protein kinase C iota polypeptide or an increased level of protein kinase C iota polypeptide expression or activity, as compared to the copy number or level observed in control cells (e.g., non-cancerous control cells).

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 6 is a listing of a nucleic acid sequence (SEQ ID NO:1) that encodes an amino acid sequence (SEQ ID NO:2) of a constitutively active mutant of human PKCι. The mutation is highlighted in underlined bold.

FIG. 7 is a listing of a nucleic acid sequence (SEQ ID NO:3) that encodes an amino acid sequence (SEQ ID NO:4) of a kinase deficient mutant of human PKCι. The mutation is highlighted in underlined bold.

FIG. 10A contains a photograph of an immunoblot analysis of human NSCLC cell lines for PKCι, PKCζ, and actin. PKCι is overexpressed in all NSCLC cell lines, whereas PKCζ was not detected. Purified recombinant human PKCζ and PKCι were included as controls for antibody specificity. FIG. 10B contains a photograph of an immunoblot analysis of A549 cell transfectants expressing either pBabe, wild-type human PKCι (wtPKCι), or kinase-deficient human PKCι (kdPKCι) for Flag, PKCι, and actin. FIG. 10C is a graph plotting growth of A549 transfectants in adherent culture in growth medium supplemented with 10%, 2%, or no serum. FIG. 10D is a bar graph plotting the number of A549/pBabe, A549/wtPKCι, and A549/kdPKCι cells invading through Matrigel coated chambers. FIG. 10E is a bar graph plotting the number of colonies formed by anchorage-independent growth of A549/pBabe, A549/wtPKCι, or A549/kdPKCι cells in soft agar.

FIG. 11E also contains a bar graph plotting the number of colonies formed by anchorage-independent growth of ChaGoK cell transfectants in soft agar.

DETAILED DESCRIPTION

Figure 1:
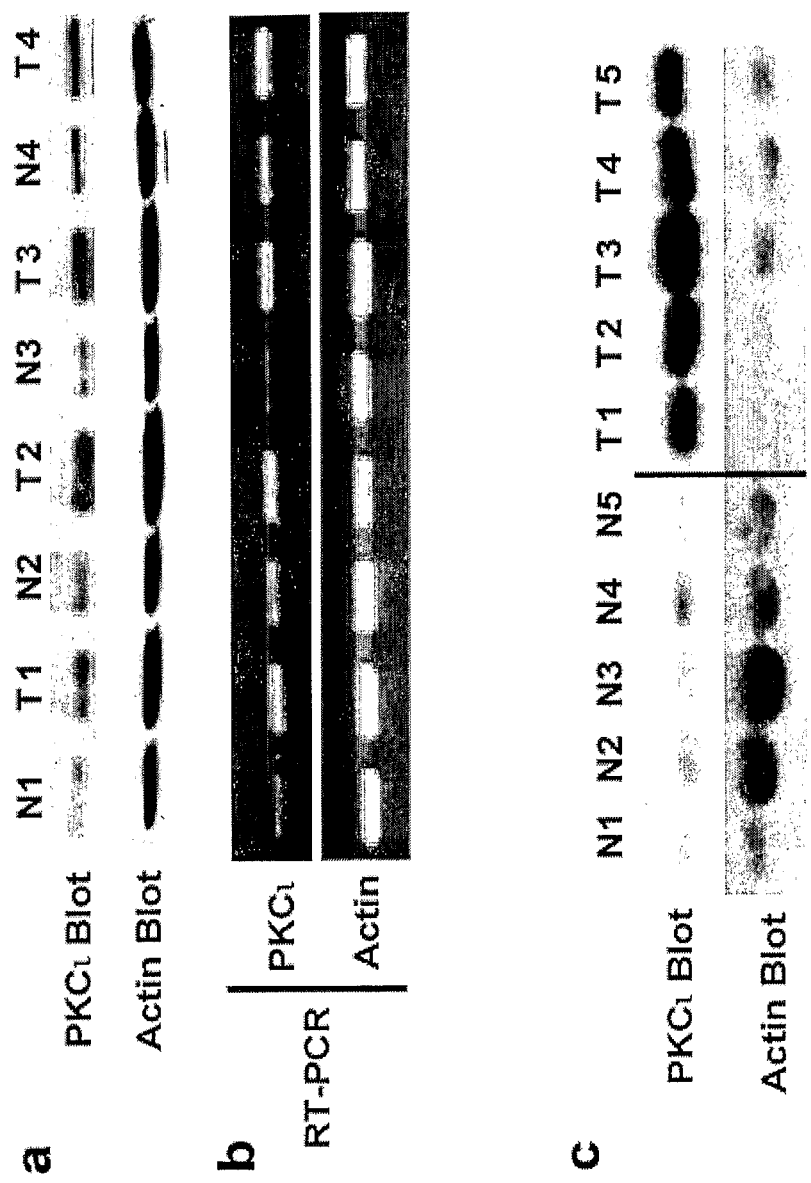
FIG. 1: PKCι expression is increased in azoxymethane (AOM)-induced mouse colon tumors and in human colon tumors. Total protein lysates (a) and total RNA extracts (b) were prepared from AOM-induced mouse colon tumors and uninvolved scraped colonic epithelium from the same animals as described elsewhere (Gokmen-Polar et al., *Cancer Res.*, 61:1375-81 (2001)). (a) Protein extracts were subjected to immunoblot analysis for PKCι and actin. (b) Mouse PKCι and β-actin mRNA expression was assessed by RT-PCR analysis as described elsewhere (Gokmen-Polar et al., *Cancer Res.*, 61:1375-81 (2001)). Lanes N1-N4, uninvolved mouse colonic epithelium; T1-T4, mouse colon tumors. (c) Total protein lysates were prepared from matched, uninvolved colonic epithelium and colon tumor tissue from five patients with colon carcinoma as described elsewhere (Gokmen-Polar et al., *Cancer Res.*, 61:1375-81 (2001)). Equal amounts of protein (50 μg) were electrophoresed, transferred to nitrocellulose, and subjected to immunoblot analysis for PKCι and actin as described elsewhere (Gokmen-Polar et al., *Cancer Res.*, 61:1375-81 (2001)). Lanes N1-N5, uninvolved human colonic epithelium, Lanes T1-T5, matched human colon tumors.

The invention provides methods and materials related to PKCι signaling. It is noted that PKCι generally refers to a human polypeptide. The corresponding polypeptide in rodents, which is about 95 percent homologous at the amino acid level to human PKCι, is generally referred to as protein kinase C lambda. For the purpose of this document, the term "PKCι" refers to any PKCι polypeptide including, without limitation, human PKCι polypeptides and rodent protein kinase C lambda.

In some embodiments, the invention provides transgenic non-human animals. Such non-human animals can be farm animals such as pigs, goats, sheep, cows, horses, and rabbits, rodents such as rats, guinea pigs, and mice, and non-human primates such as baboons, monkeys, and chimpanzees. The term "transgenic non-human animal" as used herein includes, without limitation, founder transgenic non-human animals as well as progeny of the founders, progeny of the progeny, and so forth, provided that the progeny retain the transgene. The nucleated cells of the transgenic non-human animals provided herein can contain a transgene that includes a promoter sequence operably linked to a nucleic acid sequence encoding a PKCι polypeptide. A PKCι polypeptide can be a wild-type PKCι polypeptide (e.g., wild-type human PKCι), a constitutively active PKCιpolypeptide (e.g., constitutively active human PKCι), or a kinase deficient PKCιpolypeptide (e.g., kinase deficient human PKCι). The transgenic non-human animal can express the PKCι polypeptide and can develop more preneoplastic colonic lesions after carcinogen (e.g., azoxymethane) treatment than a corresponding wild-type non-human animal treated with the carcinogen.

The nucleic acid sequence encoding the PKCι polypeptide can be a cDNA or can include introns or adjacent 5'- or 3'-untranslated regions (e.g., a genomic nucleic acid). The nucleic acid sequence encoding the PKCι polypeptide can be operably linked to any promoter sequence. For example, a promoter sequence that facilitates the expression of a nucleic acid without significant tissue- or temporal-specificity can be used. Examples of such promoter sequences include, without limitation, viral promoters such as a herpes virus thymidine kinase (TK) promoter sequence, a SV40 promoter sequence, or a cytomegalovirus (CMV) promoter sequence. In some examples, nucleic acid encoding a PKCι polypeptide can be operably linked to a tissue-specific promoter sequence such as a colon-specific promoter sequence (e.g., a $Fabpl^{4x\ at\ -132}$ promoter sequence). Other tissue-specific promoter sequences include, without limitation, those listed in Table 1.

TABLE 1

Alternative Tissue-specific promoters

| Tissue | Promoter | Reference |
|---|---|---|
| Breast | Whey acidic protein | Tessier et al., Cancer Res., 64: 209-214 (2004) |
| Prostate | Probasin | Masumori et al., Cancer Res., 61: 2239-2249 (2001) |
| Lung | Surfactant protein C | Glasser et al., Am. J. Physiol. Lung Cell Mol. Physiol., 278: L933-945 (2000) |
| Kidney | Ksp-cadherin | Igarashi et al., Am. J. Physiol, 277: F599-610 (1999) |
| Liver | Albumin | Pinkert et al., Genes Dev., 1: 268-276 (1987) |
| Brain | Glial fibrillary acidic protein | Shi et al., Proc. Natl. Acad. Sci. USA, 98: 12754-12759 (2001) |
| Pancreas | Human pancreatic secretory trypsin inhibitor | Yasuda et al., J. Biol. Chem., 273: 34413-34421 (1998) |

In some cases, an inducible promoter sequence can be used. For example, a Tet-on or Tet-off expression system can be used to design one or more constructs that allow expression to be regulated in response to a drug (e.g., tetracycline or doxycycline). Briefly, Tet-on and Tet-off expression systems are binary transgenic systems in which expression from a target transgene depends on the activity of an inducible transcriptional activator. In both the Tet-on and Tet-off systems, expression of the transcriptional activator can be regulated both reversibly and quantitatively by exposing a transgenic animal to varying concentrations of tetracycline or a tetracycline derivatives such as doxycycline. In some cases, a Tet-on or Tet-off system can be used with a tissue-specific promoter sequence (e.g., a lung-specific promoter sequence) such that a PKCι polypeptide is expressed in a particular tissue (e.g., lung tissue) in response to changes in, for example, tetracycline or doxycycline.

The term "operably linked" as used herein refers to positioning a regulatory element (e.g., a promoter sequence, an inducible element, or an enhancer sequence) relative to a nucleic acid sequence encoding a polypeptide in such a way as to permit or facilitate expression of the encoded polypeptide. In the transgenes disclosed herein, for example, an enhancer can be positioned 3' or 5' relative to the nucleic acid encoding a PKCι polypeptide, and can be positioned within the transgene in either the 5' to 3' or the 3' to 5' orientation.

Various techniques known in the art can be used to introduce transgenes into non-human animals to produce founder lines, in which the transgene is integrated into the genome. Such techniques include, without limitation, pronuclear microinjection (See, e.g., U.S. Pat. No. 4,873,191), retrovirus mediated gene transfer into germ lines (Van der Putten et al., Proc. Natl. Acad. Sci. USA, 82:6148-1652 (1985)), gene targeting into embryonic stem cells (Thompson et al., Cell 56:313-321 (1989)), electroporation of embryos (Lo, Mol. Cell. Biol., 3:1803-1814 (1983)), and in vitro transformation of somatic cells, such as cumulus or mammary cells, followed by nuclear transplantation (Wilmut et al., Nature, 385:810-813 (1997); and Wakayama et al., Nature, 394:369-374 (1998)). For example, fetal fibroblasts can be genetically modified to express a PKCι polypeptide, and then fused with enucleated oocytes. After activation of the oocytes, the eggs are cultured to the blastocyst stage. See, for example, Cibelli et al., Science, 280:1256-1258 (1998). Standard breeding techniques can be used to create animals that are homozygous for the transgene from the initial heterozygous founder animals. Homozygosity is not required, however, as the phenotype can be observed in hemizygotic animals.

Once transgenic nonhuman animals have been generated, expression of a PKCι polypeptide can be assessed using standard techniques. Initial screening can be accomplished by Southern blot analysis to determine whether or not integration of the transgene has taken place. For a description of Southern analysis, see sections 9.37-9.52 of Sambrook et al., 1989, Molecular Cloning, A Laboratory Manual, second edition, Cold Spring Harbor Press, Plainview; NY. Polymerase chain reaction (PCR) techniques also can be used in the initial screening. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example PCR Primer: A Laboratory Manual, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis, Genetic Engineering News, 12:1 (1992); Guatelli et al., Proc. Natl. Acad. Sci. USA, 87:1874-1878 (1990); and Weiss, Science, 254:1292-1293 (1991).

Expression of a nucleic acid sequence encoding a PKCι polypeptide in the tissues of transgenic non-human animals can be assessed using techniques that include, without limitation, Northern blot analysis of tissue samples obtained from the animal (e.g., intestinal tissue), in situ hybridization analysis, Western analysis, immunoassays such as enzyme-linked immunosorbent assays, and reverse-transcriptase PCR (RT-PCR). As described herein, expression of a constitutively active PKCι polypeptide can result in transgenic animals exhibiting more preneoplastic colonic lesions after carcinogen (e.g., azoxymethane) treatment than a corresponding wild-type animal treated with the carcinogen.

In some embodiments, transgenic animals containing a transgene that encodes a PKCι polypeptide lacking protein kinase C iota activity can exhibit less protein kinase C iota activity in, for example, the colonic epithelium than a corresponding wild-type rodent. It is understood that a particular phenotype in a transgenic animal typically is assessed by comparing the phenotype in the transgenic animal to the corresponding phenotype exhibited by a control non-human animal that lacks the transgene.

In some embodiments, the transgenic non-human animals can include a second transgene that contains a nucleic acid sequence of an oncogene such as ras (e.g., a K-Ras polypeptide). The nucleic acid sequence of human K-ras can be obtained from GenBank (e.g., GenBank Accession No. NM_033360). The second transgene also can include regulatory elements as discussed above (e.g., a tissue-specific promoter sequence).

The invention also provides tissues (e.g., colon sections, lung sections, etc.) and cells (e.g., intestinal cells, lung cells, etc.) obtained from the transgenic non-human animals provided herein.

In addition, the invention provides inhibitors of PKCι signaling. For example, a polypeptide sequence corresponding to amino acids 1-113 of a PKCι polypeptide can be used to block Ras-mediated transformation. Expression of the 1-113 polypeptide region of PKCι appears to block PKCι signaling through disruption of protein/protein interactions between PKCι and Par-6. Polypeptides shorter (e.g., the 1-110 region, the 5-113 region, the 10-113 region, or 5-110 region) or longer (e.g., the 1-115 region, the 1-117 region, or the 1-120 region) than a 113 amino acid fragment of a PKCι polypeptide can be used as an inhibitor of PKCι signaling.

In addition, polypeptides derived from other regions of PKCι that are involved in the interaction of PKCι with other signaling molecules (e.g., Src, Par-4, p62/ZIP, and Par-3 polypeptides) can be used as inhibitors of PKCι signaling. Likewise, the corresponding regions on molecules such as Par-6, Src, Par-4, p62/ZIP, and Par-3 that mediate the binding of these molecules to PKCι can be used as inhibitors. Regions that can be used to design an inhibitor include, without limitation, (a) the PXXP domain that mediates binding of Src to PKCι and (b) sites on PKCι that are phosphorylated (either by PKCι itself or by other kinases). For example, Src phosphorylates multiple sites on PKCι including tyrosines 256, 271 and 325 (Wooten et al., *Mol. Cell. Biol.*, 21:8414-8427 (2001)). Phosphorylation at Y325 can be responsible for src-mediated activation of PKCι activity. Polypeptides surrounding this region can act as inhibitors of src-mediated activation of PKCι. Likewise, phosphorylation of Y256 (by src or other kinases) can regulate the ability of PKCι to enter the nucleus of the cell (White et al., *J. Cell. Biochem.*, 85:42-53 (2002)), although other regions on PKCι can also be involved in regulating nuclear localization of PKCι (Perander et al., *J. Biol. Chem.*, 276:13015-13024 (2001)). Expression of polypeptides surrounding any of these regions of PKCι can be used to disrupt PKCι signaling.

In some embodiments, an inhibitor of PKCι signaling is not a polypeptide. Examples of non-polypeptide inhibitors of PKCι signaling include, without limitation, aurothioglucose, aurothiomaleate, thimerosal, phenylmercuric acetate, ebselen, cisplatin, apomorphine, pyrantel pamoate, gossypol-acetic acid complex, ellagic acid, and hexestrol.

The invention also provides methods for identifying PKCι signaling inhibitors. In general, such methods include (a) designing an assay to measure the binding of a PKCι polypeptide and a polypeptide (e.g., a Par6 polypeptide) that interacts with a PKCι polypeptide and (b) screening for compounds that disrupt this interaction. For example, expression plasmids can be designed to express a fragment of a Par6 polypeptide (e.g. amino acids 1-125 of a human Par6 polypeptide) as a fusion protein containing a naturally fluorescent protein (e.g., cyan fluorescent protein (CFP) or yellow fluorescent protein (YFP)). Another set of plasmids can be designed to express a region of a PKCι polypeptide (e.g., amino acids 1-113 or a full-length PKCι polypeptide) that binds to the Par6 region. This region of a PKCι polypeptide also can be expressed as a fusion protein with either CFP or YFP. The binding of these recombinant polypeptides can be followed by measuring fluorescence from the polypeptides when the complex is excited by a specific wave length of light. CFP and YFP fluoresce when they are stimulated by light. However, the wavelength of light that excites CFP is different from that which excites YFP. Thus, if one wavelength of light is used, CFP can emit cyan fluorescent light but YFP will not fluoresce. If a different wavelength of light is used, YFP can fluoresce yellow, but CFP will not fluoresce. When CFP and YFP are brought into very close proximity, such as when Par6/CFP and PKCι/YFP bind to each other, and when the wavelength of light is used that will cause CFP to emit cyan fluorescent light, then some of the energy that would ordinarily be emitted as cyan colored light will be transferred to the adjacent YFP molecule on the PKCι/YFP molecule. This energy can excite YFP to emit yellow fluorescent light. This process of energy transfer from CFP to YFP is called fluorescence energy transfer (FRET). FRET can be a very sensitive way of measuring binding between two molecules that contain CFP and YFP. For example, when Par6/CFP and PKCι/YFP (or the converse pair: Par6/YFP and PKCι/CFP) are put together, FRET can occur. In addition, FRET can be used to assess binding of these two molecules since when binding is disrupted, FRET can be abolished.

In one embodiment, recombinant Par6/CFP and PKCι/YFP polypeptides can be added to the wells of either 96 well or 384 well plates. Then, a single compound from a large compound library can be added to each of the individual wells. The entire plate can be placed in a fluorescence plate reader that can measure FRET in each of the wells. Those wells that show a decrease or loss of FRET can contain a compound that can potentially disrupt the interaction between Par6 and PKCι. Appropriate controls can be included in the assay to avoid identifying compounds that inhibit FRET by other, non-specific means. This type of assay can be adapted for high throughput screening of compound libraries containing thousands and even hundreds of thousands of compounds.

Once a compound is identified as being a candidate for disrupting the interaction of Par6 and PKCι polypeptides, the compound can be put through a secondary screen in which its ability to disrupt Par6/PKCι polypeptide binding is determined in cells expressing recombinant Par6 and PKCι polypeptides. Compounds that disrupt Par6/PKCι polypeptide binding in cells can be further screened for the ability to inhibit PKCι-dependent cellular transformation.

The invention also provides methods for diagnosing cancer. For example, samples can be obtained and assessed for the presence of an elevated level of PKCι polypeptides or an elevated level of PKCι polypeptide activity. The presence of an elevated level of PKCι polypeptides or elevated level of PKCι polypeptide activity can indicate the presence of cancer and/or precancerous cells. Any method can be used to assess the level of PKCι polypeptide expression. For example, immunoblot analysis and/or immunohistochemistry can be used to examine the expression of PKCι polypeptides in tissue and/or cell samples. In some cases, PKCι polypeptide activity can be assessed using any of the methods provided herein.

The invention will be further described in the following examples, which do not limit the scope of the invention described in the claims.

EXAMPLES

Example 1

Methods and Materials

Analysis of PKCι Expression in Mouse and Human Colon Tumors

AOM-induced colon tumors were produced in C57B1/6 mice as described elsewhere (Gokmen-Polar et al., *Cancer Res.*, 61:1375-81 (2001)). Fresh frozen tissue from human colon carcinomas and uninvolved colonic epithelium was obtained from surgical specimens. Isolation of RNA and protein for RT-PCR and immunoblot analysis, respectively, was performed as described elsewhere (Gokmen-Polar et al., *Cancer Res.*, 61:1375-81 (2001)). Immunoblot analysis for PKCι and actin was conducted using isozyme-specific antibody against PKCι and actin (Santa Cruz, Inc.) as described elsewhere (Gokmen-Polar et al., *Cancer Res.*, 61:1375-81 (2001) and Murray et al., *J. Biol. Chem.*, 272:27521-4 (1997)). This PKCι antibody recognizes PKCι, but not PKCζ (Murray et al., *J. Biol. Chem.*, 272:27521-4 (1997)).

Primers for RT-PCR analysis were as follows: PKCι forward primer: 5'-GCTTA-TGTTTGAGATGATGGCGG-3' (SEQ ID NO:5), PKCι reverse primer: 5-GTGACA-ACCCAATCGTTCCG-3' (SEQ ID NO:6); actin forward primer: 5'-GTGGGC-CGCTCTAGGCACCAA-3' (SEQ ID NO:7), actin reverse primer: 5'-CTCTTTGAT-GTCACG-CACGATTTC-3' (SEQ ID NO:8).

Colon tumors and uninvolved colonic epithelium from AOM-treated mice were fixed in 10% buffered formalin, sectioned, and subjected to antigen retrieval (Vector Labs). Immunohistochemical detection of PKCι was performed using the specific PKCι antibody (Santa Cruz) and the DAKO LSAB2 (DAB) detection system (DAKO). Specificity of immunostaining for PKCι was demonstrated by inclusion of a 5-fold molar excess of the peptide used to generate the PKCι antibody (Santa Cruz) in the antibody dilution. Digital images were acquired on an Olympus DX51 microscope equipped with a DP70 digital camera using a 20× objective lens. Images were captured using the DP Controller software and processed in Adobe Photoshop.

Production of Transgenic Mice and Carcinogenesis Studies

Nucleic acid encoding a constitutively active human PKCι (caPKCι) and nucleic acid encoding a kinase deficient human PKCι (kdPKCι) were generated and characterized elsewhere (Jamieson et al., *J. Biol. Chem.*, 274:3927-3930 (1999) and Lu et al., *Oncogene*, 20:4777-4792 (2001)). Transgenic caPKCι and kdPKCι mice were generated on a C57B1/6 background using the Fabpl$^{4\times\ at\ -132}$ promoter (Simon et al., *J. Biol. Chem.*, 272:10652-63 (1997); provided by J. Gordon, Washington University, St. Louis, Mo.) to direct transgene expression to the colonic epithelium (Murray et al., *J. Cell Biol.*, 145:699-711 (1999)). Isolation of colonic epithelium, immunoblot analysis for PKCι, and immunoprecipitation histone kinase assays were described elsewhere (Jamieson et al., *J. Biol. Chem.*, 274:3927-3930 (1999) and Murray et al., *J. Cell Biol.*, 145:699-711 (1999)). Transgenic caPKCι, transgenic kdPKCι, and non-transgenic mice were injected with either AOM (10 mg/kg) or saline as described elsewhere (Gokmen-Polar et al., *Cancer Res.*, 61:1375-81 (2001)). ACF analysis was performed 12 weeks after the last AOM injection (Murray et al., *J. Cell Biol.*, 157:915-920 (2002)), using well-defined criteria (McLellan et al., *Carcinogenesis*, 12:2093-8 (1991). Mice were analyzed at 40 weeks for tumor number, size, location, and pathological grade as described elsewhere (Gokmen-Polar et al., *Cancer Res.*, 61:1375-81 (2001)). All tumors were classified as either tubular adenomas or intramucosal carcinomas (carcinoma in situ) by a board-certified pathologist. Digital images of the tumors were captured using a Nikon Eclipse E600 microscope equipped with a ProgRes C14 camera (Jenoptik, Jena, Germany) using a 20× objective lens. Images were acquired using ProgRes C14 software with Microsoft Photoeditor and processed with Microsoft Photoshop.

Transgenic K-ras$^{LA2}$ mice (Johnson et al., *Nature*, 410: 1111-6 (2001); provided by T. Jacks, M.I.T., Boston, Mass.) were bred to transgenic kdPKCι mice to obtain bi-transgenic K-ras$^{LA2}$/kdPKCι mice. At 12 weeks of age, transgenic K-ras$^{LA2}$ and transgenic K-ras$^{LA2}$/kdPKCι mice were assessed for spontaneous ACF formation (McLellan et al., *Carcinogenesis*, 12:2093-8 (1991) and Murray et al., *J. Cell Biol.*, 145:699-711 (1999)).

RIE Cell Transfections and Cellular Analyses

RIE cells and derivatives were grown in DMEM containing 5% FBS as described elsewhere (Ko et al., *Oncogene*, 16:3445-54 (1998)). RIE/Ras cells were described elsewhere (Sheng et al., *J. Biol. Chem.*, 275:6628-35 (2000); provided by Dr. H. M. Sheng, University of Texas Medical Branch, Galveston, Tex.). Microarray analysis of RIE/Ras cells demonstrated that these cells express no PKCζ. cDNAs encoding human wtPKCι and kdPKCι were cloned into the pBABE/FLAG/puro retroviral expression vector, and virus stocks were produced using Phoenix-E cells (provided by Dr. G. Nolan, Stanford University, Palo Alto, Calif.). Puromycin-resistant, stable transfectants were generated. Expression of FLAG-epitope-tagged PKCι was confirmed by immunoblot analysis using an anti-FLAG antibody (Sigma-Aldrich), and PKCι kinase activity was determined by immunoprecipitation histone kinase assay as described elsewhere (Jamieson et al., *J. Biol. Chem.*, 274:3927-3930 (1999)).

Recombinant retroviruses containing a dominant negative Rac1 (RacN17) that is Myc-tagged or a Myc-tagged RacV12 were generated by excising the Myc-tagged Rac1 constructs from pEXV/Rac vectors (Qiu et al., *Nature*, 374:457-9 (1995)) with EcoRI and ligating them into the EcoRI site of the LZRS-GFP retrovirus. The entire coding sequence of each construct was confirmed by DNA sequence analysis. LZRS-GFP-Rac1 retroviruses were used to infect RIE cells and derivative cell lines as described elsewhere (Ireton et al., *J. Cell Biol.*, 159:465-76 (2002)). Rac1 activity was assessed by affinity-isolation of GTP-bound Rac1 as described elsewhere (Sander et al., *J. Cell Biol.*, 143:1385-98 (1998)). Active GTP-bound Rac1 and total Rac1 were identified by immunoblot analysis using a Rac1 monoclonal antibody (BD Transduction Laboratories) and quantitated by densitometry.

Invasiveness of RIE cell transfectants was assessed in Transwell inserts pre-coated with Matrigel (6.5 mm diameter, 8 μm pore size; BD Biosciences). DMEM containing 10% FBS was added to the lower chamber and 5×10$^4$ cells were suspended in serum-free DMEM (500 μl) and placed in the top chamber of the Transwell insert. Cells were incubated for 22 h at 37° C. in 5% CO$_2$, at which time non-invading cells were removed from the upper chamber. Cells that had invaded through the Matrigel-coated filter were fixed in 100% methanol, stained with Crystal Violet and counted on a microscope using a calibrated ocular grid. Fifteen representative areas of the lower chamber were counted to determine the number of invasive cells in each well.

To assess anchorage-independent growth, RIE cell transfectants were suspended in DMEM supplemented with 10% FBS, 1.5% agarose, and a 1% insulin, transferrin and selenium solution (Sigma-Aldrich), and plated (300 cells/60 mm dish) on a layer of 1.5% agar containing the same medium. Cell colonies were fixed with 20% methanol and stained with Giemsa after 7-14 days in culture and quantified under a dissecting microscope.

Example 2

PKCι Expression

The potential involvement of PKCι in colon carcinogenesis was assessed by determining expression of PKCι in normal mouse colonic epithelium and in colon tumors induced by the carcinogen, azoxymethane (AOM). Immunoblot analysis demonstrated that PKCι expression is elevated in AOM-induced colon tumors when compared to matched, uninvolved colonic epithelium (FIG. 1a). Reverse transcriptase-(RT)-PCR analysis demonstrated a corresponding increase in PKCι mRNA in these tumors (FIG. 1b). Immunoblot analysis demonstrated that PKCι expression is also elevated in human colon carcinoma specimens when compared to matched uninvolved colonic epithelium (FIG. 1c), demonstrating that elevated PKCι is a common feature of AOM-induced mouse colon tumors and human colon carcinomas.

Figure 2:
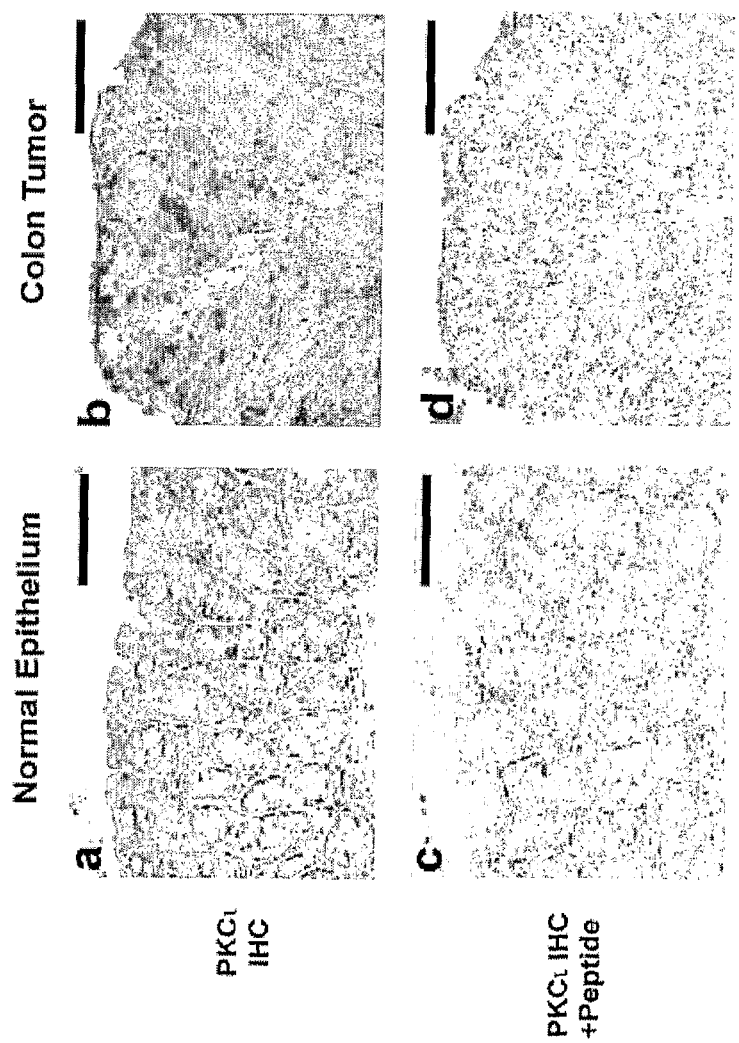
FIG. 2: PKCι expression is elevated in AOM-induced colon tumors. Immunohistochemical analysis of sections from normal, uninvolved epithelium (a and c) and an AOM-induced colon tumor (b and d) in the same animal was performed using a specific PKCι antibody in the absence (a and b) or presence (c and d) of a competing PKCι peptide. Bars equal 50 μm.

Immunohistochemical staining confirmed the elevated expression of PKCι in AOM-induced colon tumors in mice when compared to normal adjacent colonic epithelium (FIG. 2). Significant expression of PKCι was detected in normal colonic epithelium (FIG. 2, panel a), but much stronger staining was observed in colon tumor tissue (FIG. 2, panel b), consistent with our immunoblot analysis. Specificity of the immunostaining was assessed by staining sections from the same tissue with an antibody dilution to which had been added a five-fold molar excess of a peptide corresponding to the epitope on PKCι used to generate the PKCι antibody (FIG. 2, panels c and d). Inclusion of the blocking PKCι peptide abolished the immunostaining, confirming the specificity for PKCι.

Example 3

Carcinogenesis

The elevated expression of PKCι in colon tumors indicated that PKCι may play an important role in colon carcinogenesis. To test this hypothesis, transgenic mice were generated to express either a constitutively active (caPKCι) or kinase-deficient (kdPKCι) form of human PKCι in the colonic epithelium using a modified rat liver fatty acid binding protein promoter (Murray et al., *J. Cell Biol.*, 157:915-920 (2002) and Simon et al., *J. Biol. Chem.*, 272:10652-63 (1997)). Briefly, nucleic acid encoding caPKCι was generated by PCR-mediated site-directed mutagenesis and amplification of a fragment containing an alanine to glutamine ($A^{120}E$) substitution within the pseudosubstrate domain of human PKCι (FIG. 6). Nucleic acid encoding kdPKCι was created using a two-step PCR mutagenesis method to introduce a ($K^{274}W$) substitution at the ATP binding site of human PKCι (FIG. 7). Transgene constructs consisting of the Fabpl$^{4\times\ at}_{-132}$ promoter (Simon et al., *J. Biol. Chem.*, 272:10652-10663 (1997)), the caPKCι or kdPKCι cDNA, and the SV40 large T antigen polyadenylation site were produced by conventional cloning techniques, and the sequences confirmed by direct microsequencing. The transgene constructs were propagated in the mammalian expression vector pREP4. The transgene inserts were excised from the cloning vector using NheI (5') and XbaI (3'), purified, and microinjected into C57BL/6J mouse oocytes as described elsewhere (Hogan et al., (1994) Manipulating the Mouse Embryo: A Laboratory Manual, 2nd Ed., Cold Spring Harbor Press, Cold Spring Harbor, N.Y.). The microinjections and generation of transgenic founder mice were conducted at a transgenic mouse facility.

Figure 3:
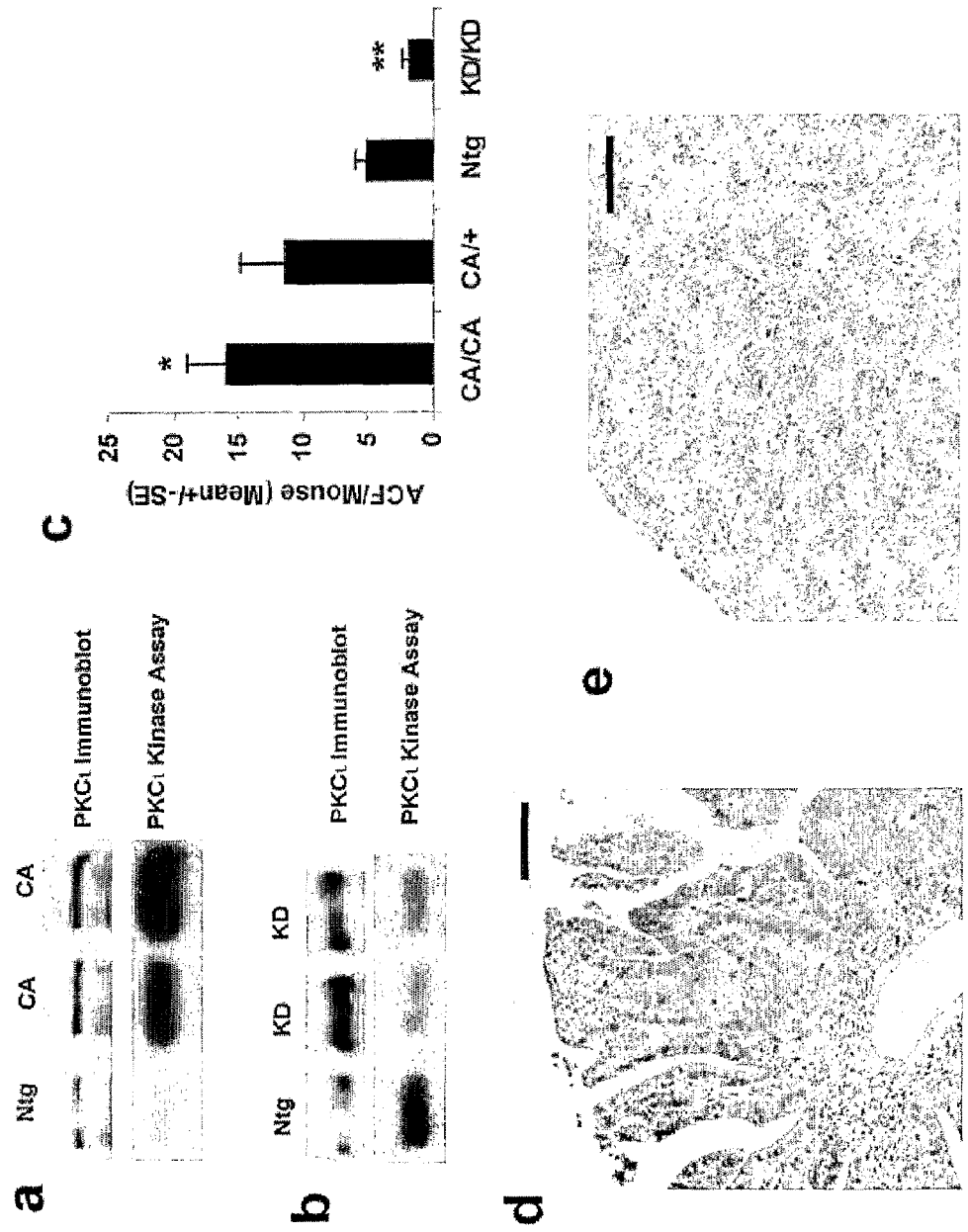
FIG. 3: Transgenic caPKCι mice are susceptible to AOM-induced colon carcinogenesis. a) and b) Total protein lysates from scraped colonic epithelium from non-transgenic (Ntg) and transgenic a) caPKCι (CA) or b) kdPKCι (KD) mice were subjected to immunoblot analysis for PKCι expression (a and b, upper panels) and to immunoprecipitation kinase assay for PKCι activity (a and b, lower panels). c) Colons from AOM-treated mice with the indicated genotype were scored for ACF (aberrant crypt foci; McLellan et al., *Carcinogenesis*, 12:2093-8 (1991) and Murray et al., *J. Cell Biol.*, 145:699-711 (1999)). CA/CA: homozygous caPKCι mice; CA/+: heterozygous caPKCι mice, KD/KD: homozygous kdPKCι; Ntg: non-transgenic mice. Results represent the average ACF per animal ±SEM (n=4-9; *p=0.05 versus Ntg; **p=0.02 versus Ntg). d) H&E stained section of a tubular adenoma from the colon of a non-transgenic mouse 40 weeks after AOM treatment. e) H&E stained section of a carcinoma in situ from the colon of a caPKCι mouse 40 weeks after AOM treatment. d) and e) Bars equal 100 μm.

Immunoblot analysis demonstrated that transgenic caPKCι and kdPKCι mice express elevated PKCι protein in the colonic epithelium (FIGS. 3a and b, upper panels). Transgenic caPKCι mice exhibited high intrinsic PKCι activity in the colonic epithelium when compared to non-transgenic littermates (FIG. 3a, lower panel). In contrast, transgenic kdPKCι mice exhibited decreased colonic PKCι kinase activity when compared to non-transgenic littermates (FIG. 3b, lower panel; the autoradiograph in FIG. 3b is a longer exposure than FIG. 3a in order to reveal the decreased PKCιactivity in transgenic kdPKCι mice). Neither transgenic caPKCι nor transgenic kdPKCι mice exhibited demonstrable changes in proliferative index, proliferation zone, or expression of differentiation markers in the colonic epithelium.

To assess the importance of PKCι in colon carcinogenesis, transgenic caPKCι, transgenic kdPKCι, and non-transgenic mice were treated with AOM (Gokmen-Polar et al., *Cancer Res.*, 61:1375-81 (2001) and Murray et al., *J. Cell Biol.*, 145:699-711 (1999)). Initially, mice were analyzed 12 weeks after AOM treatment for the development of preneoplastic colonic lesions, aberrant crypt foci (ACF) (FIG. 3c). Heterozygous transgenic caPKCι mice developed about twice as many ACF, and homozygous caPKCι mice about three times as many ACF, as non-transgenic littermates (FIG. 3c). In contrast, homozygous transgenic kdPKCι mice developed significantly fewer ACF than non-transgenic mice. Thus, PKCι activity in the colonic epithelium correlates directly with susceptibility to AOM-induced ACF formation. ACF occur in both humans and mice and are considered to be precursors to colon tumors (McLellan et al., *Cancer Res.*, 51:5270-4 (1991) and Takayama et al., *N. Engl. J. Med.*, 339:1277-84 (1998)). ACF contain many of the same genetic and biochemical alterations found in colon tumors, including increased expression of PKCβII (Gokmen-Polar et al., *Cancer Res.*, 61:1375-81 (2001)) and activating K-Ras mutations (Shivapurkar et al., *Cancer Lett.*, 115:39-46 (1997)). Both the number and multiplicity (number of crypts/focus) of ACF are highly predictive of subsequent colon tumor formation in rodents (Magnuson et al., *Cancer Res.*, 53:4499-504 (1993)).

The effect of transgenic caPKCι expression on colon tumor formation was assessed. Transgenic caPKCι mice exhibited a three-fold higher incidence of tumors than non-transgenic control mice [63.6% (7/11) versus 20% (2/10) tumor-bearing mice]. In addition to an increase in tumor incidence, transgenic caPKCι mice developed predominantly malignant intramucosal carcinomas (6/7 tumors; FIG. 3e), whereas non-transgenic control mice developed mainly benign tubular adenomas (2/3 tumors; FIG. 3d). These results demonstrate that elevated PKCι activity in the colonic epithelium has two major effects on colon carcinogenesis. The first effect is an increase in formation of preneoplastic lesions and subsequent colon tumors. The second effect is to promote tumor progression from benign adenoma to malignant intramucosal carcinoma. Due to the low tumor incidence in non-transgenic mice it was impractical to assess whether transgenic kdPKCι mice would develop significantly fewer tumors.

Example 4

Ras Signaling

Figure 4:
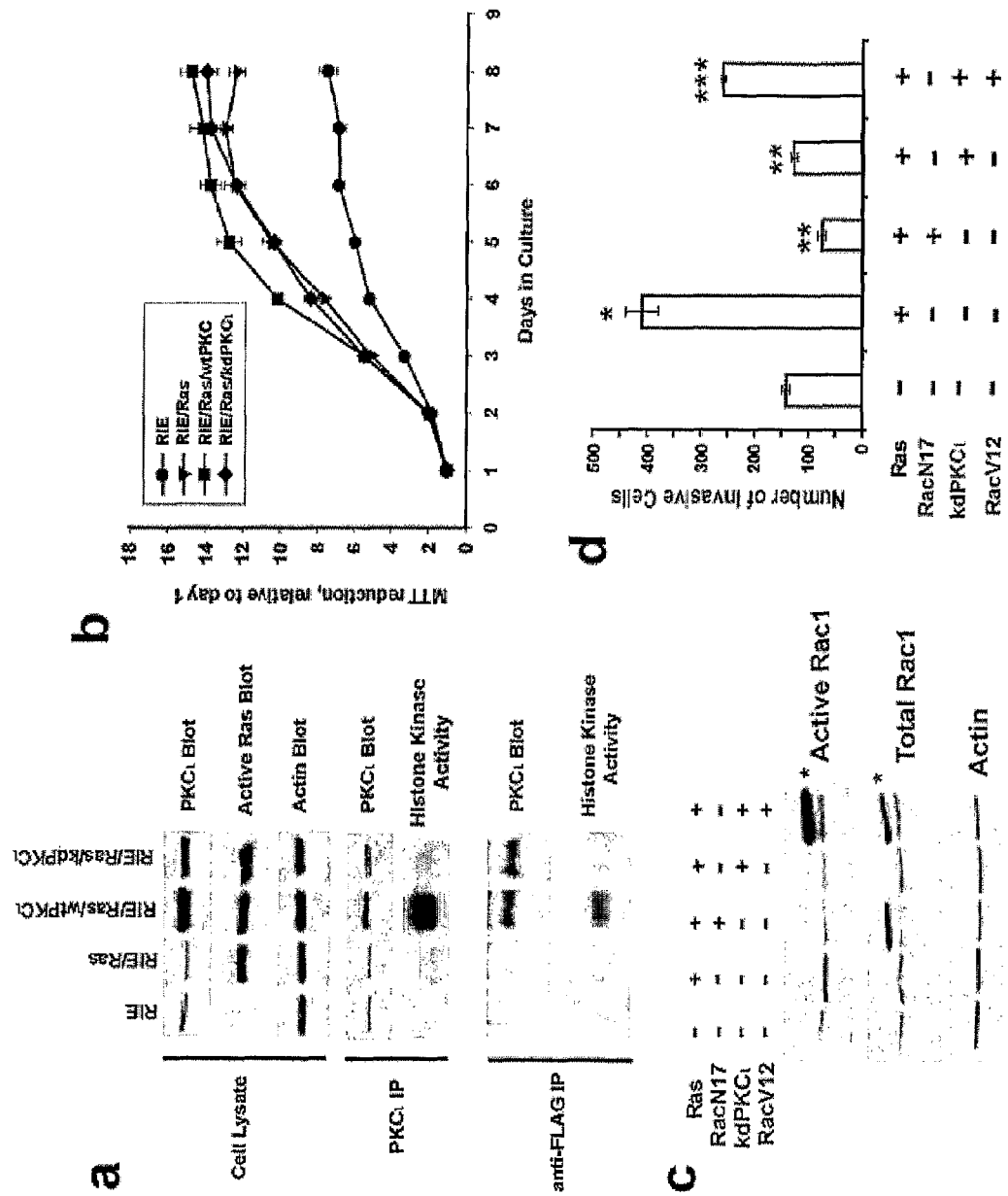
FIG. 4: PKCι is required for oncogenic Ras-induced Rac1 activation and invasion in vitro. a) rat intestinal epithelial (RIE) cells were stably transfected with control empty vector (RIE); Ras (RIE/Ras); Ras and wtPKCι (RIE/Ras/wtPKCι); or Ras and dnPKCι (RIE/Ras/kdPKCι). Total cell lysates from these cell lines were subjected to immunoblot analysis for expression of PKCι (first panel), oncogenic V12 Ras (second panel) and β-actin (third panel). Immunoprecipitates from cells using a specific PKCι antibody were analyzed by immunoblot analysis for PKCι (fourth panel) and for PKCι activity (fifth panel). Anti-FLAG immunoprecipitates from these cells were analyzed by immunoblot analysis for PKCι (sixth panel) and assayed for PKCι activity (seventh panel). b) Growth of RIE cells and RIE cell transfectants was monitored daily by measuring $OD_{570}$ after reduction of 3-(4,5-dimethylthiazol-2-yl)-2,5-diphenyl tetrazolium bromide as described previously (Murray et al., *J. Cell Biol.*, 157:915-920 (2002)). Data represent the mean ±SD from three independent determinations. c) Active (GTP-bound) Rac1 was isolated from the indicated RIE cell transfectants: control empty vector; Ras; Ras and a dominant negative Rac1 (RacN17); Ras and kdPKCι; and Ras and kdPKCι and RacV12. Immunoblot analysis was conducted for active Rac1 (upper panel), total cellular Rac1 (middle panel) and β-actin (lower panel). The asterisk indicates the migration of Myc-tagged, virally-expressed Rac1 mutants. d) The indicated RIE transfectants were evaluated for invasiveness in Matrigel-coated Transwell chambers. Data represent the average number of cells invading into the lower chamber ±SD from three independent experiments. *p=0.02 versus RIE+control vector; p= or <0.02 versus RIE/Ras; *p=0.005 versus RIE/Ras/kdPKCι.

A relationship may exist between PKCι and Ras signaling (Coghlan et al., *Mol. Cell. Biol.*, 20:2880-9 (2000); Kampfer et al, *J. Biol. Chem.*, 276:42834-42 (2001); and Uberall et al., *J. Cell Biol.*, 144:413-25 (1999)). The importance of PKCι in Ras-mediated transformation of the intestinal epithelium was assessed. Rat intestinal epithelial (RIE) cells were used to study Ras-mediated transformation and to elucidate the molecular mechanisms by which PKCβII promotes a pro-carcinogenic phenotype (Murray et al., *J. Cell Biol.*, 157:915-920 (2002); Sheng et al., *J. Biol. Chem.*, 275:6628-35 (2000); and Yu et al, *J. Biol. Chem.*, 278:11167-74 (2003)). RIE cells stably transfected with oncogenic V12H-ras (RIE/Ras) were transfected with FLAG-tagged-, wild-type (wt) PKCι, or kdPKCι. Both RIE/Ras/wtPKCι and RIE/Ras/kdPKCι cells expressed elevated levels of PKCι when compared to RIE or RIE/Ras cells (FIG. 4a, top panel). Immunoblot analysis using an antibody to oncogenic V12 Ras demonstrated that RIE/Ras, RIE/Ras/wtPKCι, and RIE/Ras/kdPKCι cells express comparable levels of active oncogenic Ras (FIG. 4a, second panel). Actin immunoblot analysis confirmed that equal amounts of protein were loaded for each cell line (FIG. 4a, third panel).

Immunoprecipitation kinase assays (Jamieson et al., *J. Biol. Chem.*, 274:3927-3930 (1999)) were performed on RIE, RIE/Ras, RIE/Ras/wtPKCι, and RIE/Ras/kdPKCι cells to assess total PKCι activity in these cell lines (FIG. 4a, fourth and fifth panels). Whereas RIE and RIE/Ras cells expressed equivalent levels of endogenous PKCι (FIG. 4a, fourth panel), RIE/Ras cells exhibited elevated PKCι activity as a result of the expression of oncogenic Ras (FIG. 4a, fifth panel). Thus, expression of oncogenic Ras leads to activation of endogenous PKCι, while having no demonstrable effect on PKCι expression. RIE/Ras/wtPKCι cells expressed elevated levels of both PKCι protein and activity when compared to RIE or RIE/Ras cells, whereas RIE/Ras/kdPKCι exhibited elevated expression of PKCι, but showed no increase in PKCι activity when compared to RIE/Ras cells (FIG. 4a, fourth and fifth panel). Immunoprecipitation with an anti-FLAG antibody followed by immunoblot analysis for PKCι confirmed the expression of FLAG-wtPKCι and FLAG-kdPKCι in RIE/Ras/wtPKCι and RIE/Ras/kdPKCι cells, respectively (FIG. 4a, sixth panel). PKCι kinase assay of anti-FLAG immunoprecipitates demonstrated that RIE/Ras/wtPKCι cells contain catalytically active, FLAG-wtPKCι, whereas RIE/Ras/kdPKCι cells contain catalytically inactive FLAG-kdPKCι (FIG. 4a, seventh panel). Taken together, these data demonstrate that oncogenic Ras can activate both endogenous and transfected PKCι, and confirm that the kdPKCι construct is deficient in kinase activity.

RIE/Ras cells exhibit an increase in anchorage-dependent growth rate and saturation density when compared to RIE cells (FIG. 4b). Expression of either wtPKCι or kdPKCι had little effect on the Ras-mediated increase in anchorage-dependent growth rate or saturation density (FIG. 4b). RIE cells expressing either wtPKCι or kdPKCι in the absence of oncogenic Ras exhibited no demonstrable change in growth rate compared to RIE cells and no signs of cellular transformation.

Ras transformation is dependent upon Ras-mediated activation of the small molecular weight GTPase, Rac1 (Qiu et al., *Nature*, 374:457-9 (1995)). Therefore, Rac1 activity in RIE/Ras cells was measured (FIGS. 4c and d). RIE/Ras cells exhibit elevated Rac1 activity when compared to RIE cells (FIG. 4c). Expression of either a dominant negative Rac1 mutant, RacN17 (Qiu et al., *Nature*, 374:457-9 (1995)), or kdPKCι in RIE/Ras cells blocked Ras-mediated Rac1 activation. In contrast, expression of a constitutively active Rac1 mutant, RacV12 (Qiu et al., *Nature*, 374:457-9 (1995)), had little effect on Ras-mediated activation of endogenous Rac1. Expression of wild-type PKCι in the absence of oncogenic Ras was not sufficient to induce Rac1 activity (unpublished data). Thus, oncogenic Ras activates Rac1 in a PKCι-dependent fashion.

Both Ras and Rac1 have been implicated in cellular motility and invasion (De Corte et al., *Embo. J.*, 21:6781-90 (2002)) and RIE/Ras cells exhibit an invasive phenotype (Fujimoto et al., *Exp. Cell Res.*, 266:239-49 (2001)). The following was used to assess whether the invasive phenotype observed in RIE/Ras cells is dependent upon Rac1 and PKCι. RIE/Ras cells exhibited a highly invasive phenotype in Matrigel chambers, whereas RIE cells did not (FIG. 4d). Expression of either RacN17 or kdPKCι in RIE/Ras cells blocked Ras-mediated cellular invasion (FIG. 4d). However, expression of RacV12 in RIE/Ras/kdPKCι cells partially restored invasiveness. These results demonstrate that oncogenic Ras-mediated cellular invasion is dependent upon both Rac1 and PKCι. Interestingly, expression of either wild-type or constitutively active PKCι in the absence of oncogenic Ras failed to induce invasion, indicating that PKCι is necessary for oncogenic Ras-mediated invasion, but is not sufficient to induce invasion in the absence of oncogenic Ras.

Figure 5:
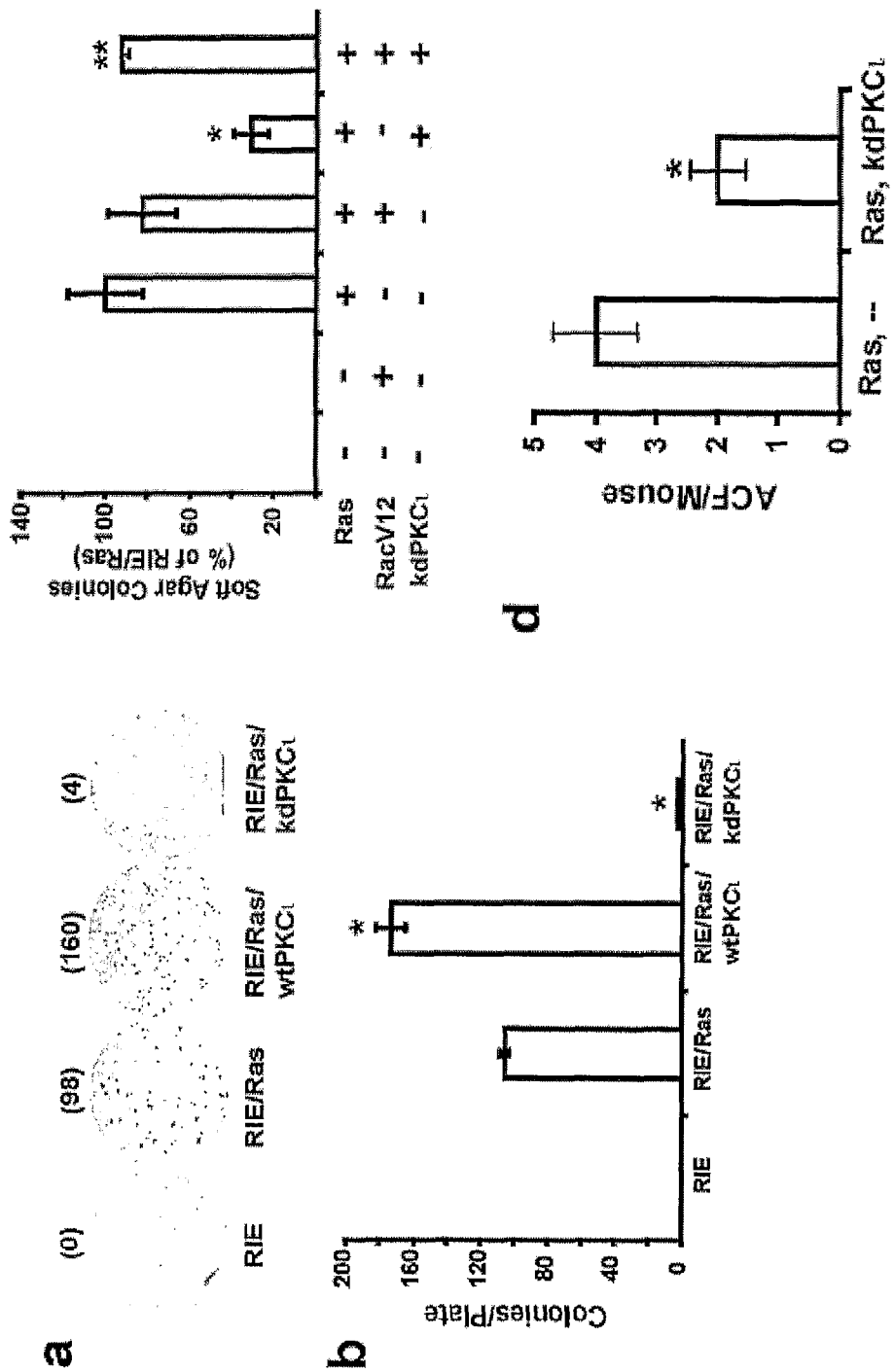
FIG. 5: Expression of dnPKCι blocks Ras-mediated transformation of the intestinal epithelium in vitro and in vivo. a) and b) RIE cells were stably transfected with control empty vector (RIE), Ras (RIE/Ras), Ras and wtPKCι (RIE/Ras/wtPKCι), or Ras and kdPKCι (RIE/Ras/kdPKCι) and evaluated for growth in soft agar. Colonies were visualized by staining with Giemsa and enumerated. a) Representative experimental results. Numbers in parenthesis represents number of colonies formed in each dish. b) Values represent the average of three independent soft agar colony formation experiments ±SEM. *p<0.002 versus RIE/Ras. c) The indicated RIE cell transfectants were analyzed as described in a). Values represent the average of five determinations ±SEM. *p=0.008 versus RIE/Ras; **p=0.0001 versus RIE/Ras/kdPKCι. d) Twelve week old K-Ras$^{LA2}$ and K-Ras$^{LA2}$/kd PKCι mice were analyzed for ACF in the proximal colon. Average number of ACF per mouse is plotted +/–the SEM, (n=5) *p=0.04.

RIE/Ras cells exhibited anchorage-independent growth in soft agar, whereas RIE cells did not (FIGS. 5a and b). Expression of wtPKCι significantly enhanced soft agar colony formation, while expression of kdPKCι blocked soft agar colony formation of RIE/Ras cells (FIGS. 5a and b). Furthermore, expression of RacV12 in RIE/Ras/kdPKCι cells restored the ability to form colonies in soft agar (FIG. 5c). Expression of RacV12 in RIE cells in the absence of oncogenic Ras did not induce soft agar colony formation, indicating that expression of active Rac1 is not sufficient to cause cellular transformation (FIG. 5c), consistent with previous reports that constitutively active Rac1 exhibits very weak transforming potential (Khosravi-Far et al., *Mol. Cell. Biol.*, 15:6443-53 (1995)). These data demonstrate that PKCι plays a critical role in Ras-mediated transformation of RIE cells since PKCι is required for Ras-mediated activation of Rac1, cellular invasion, and anchorage-independent growth. These results place PKCι downstream of oncogenic Ras and upstream of Rac1 in a pathway that stimulates invasiveness and soft agar colony formation, two hallmarks of the transformed phenotype.

The importance of PKCι in Ras-mediated colon carcinogenesis in vivo was assessed. For this purpose, a mouse model of Ras transformation consisting of a latent oncogenic K-ras allele (G12D) that is activated by spontaneous recombination in vivo was used (Johnson et al., *Nature*, 410:1111-6 (2001)). Latent K-ras (K-Ras$^{LA2}$) mice develop Ras-dependent lung carcinomas and ACF in the colonic epithelium (Johnson et al., *Nature*, 410:1111-6 (2001)). The transgenic kdPKCι mice were bred with K-Ras$^{LA2}$ mice to generate bitransgenic K-Ras$^{LA2}$/kdPKCι mice, which were then assessed for spontaneous ACF development (FIG. 5d). K-Ras$^{LA2}$/kdPKCι mice developed significantly fewer ACF in the proximal colon than K-Ras$^{LA2}$ mice. These data are consistent with the results in RIE/Ras cells in vitro, and demonstrate that PKCι is critical for oncogenic K-ras-mediated colon carcinogenesis in vivo.

Taken together, these results provide direct evidence that PKCι and Rac1 are necessary for the transformed phenotype induced by oncogenic Ras. Rac has previously been shown to be required for transformation by both H-Ras and K-Ras, the two most commonly mutated forms of Ras in human cancers. The data provided herein demonstrate that like, Rae1, PKCι is also required for both H-Ras and K-Ras-mediated transformation. Whereas H-Ras and K-Ras have been shown to have both common and distinct effectors, recent evidence indicates that both of these Ras isoforms activate Rac 1, though K-Ras appears to be able to activate Rac1 more effectively than does H-Ras (Walsh et al., *J. Biol. Chem.*, 276:15609-15 (2001)). The data provided herein also demonstrate that H-Ras induces Rac 1 activity through a PKCι-dependent pathway and that PKCι is required for K-Ras mediated colon carcinogenesis. Given the increased propensity of K-Ras to activate Rac 1, it is therefore quite likely that the Ras, PKCι, Rac 1 pathway present in RIE cells is also involved in K-Ras-mediated colon carcinogenesis in vivo. Interestingly, PKCι and Rac1 have also been implicated in the establishment of epithelial cell polarity through the formation of complexes containing PKCι, the Par6 polarity protein and Rac1 (Noda et al., *Genes Cells*, 6:107-19 (2001)). Rac1 is thought to regulate PKCι activity within these complexes to affect cell polarity (Noda et al., *Genes Cells*, 6:107-19 (2001)). The data further implicate signaling through PKCι/Par6/Rac1 complexes in Ras-mediated transformation.

These results provide conclusive evidence that PKCι activity is critical for colonic epithelial cell transformation in vivo. However, disruption of PKCι signaling (by expression of kdPKCι) has little effect on normal intestinal epithelial cell homeostasis in vitro and in vivo. Taken together, these characteristics indicate that PKCι can be an attractive target for development of novel therapeutics against colon cancer.

Example 5

PKCι Expression Levels in Human Cancers

Figure 8:
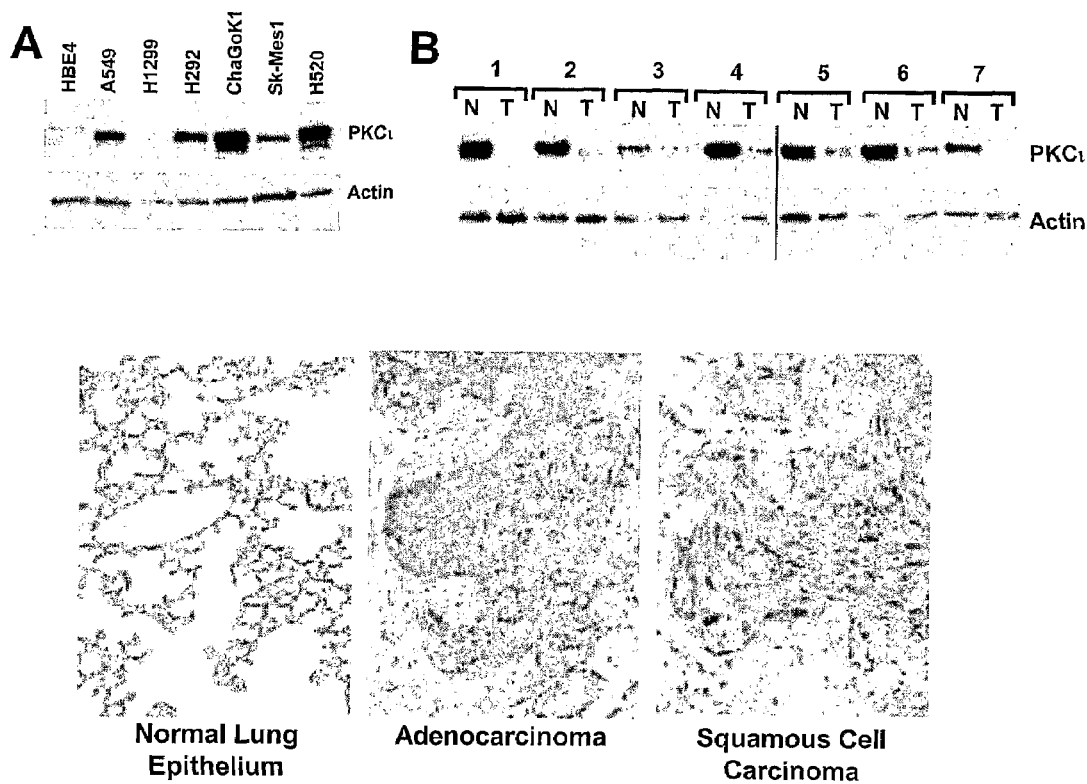
FIG. 8: Expression of PKCι in Human Cancer Tissues. A). Immunoblot analysis of PKCι expression in human non-small lung cancer cell lines. HBE4 is a non-transformed human lung epithelial cell line. The other cell lines are established human lung cancer cell lines obtained from ATCC. B) Immunoblot analysis of non-small cell lung cancer patient samples and matched normal lung epithelium from 7 patients. N=normal lung epithelium; T=lung tumor tissue from same patient. 1-7=case number. Cases 1-4 are on one immunoblot, and cases 5-7 are on a separate blot. C) Immunohistochemical staining of sections from normal lung epithelium, an adenocarcinoma of the lung, and a squamous cell carcinoma of the lung. These results are representative of more than 80 lung cancer patient samples examined.
Figure 9:
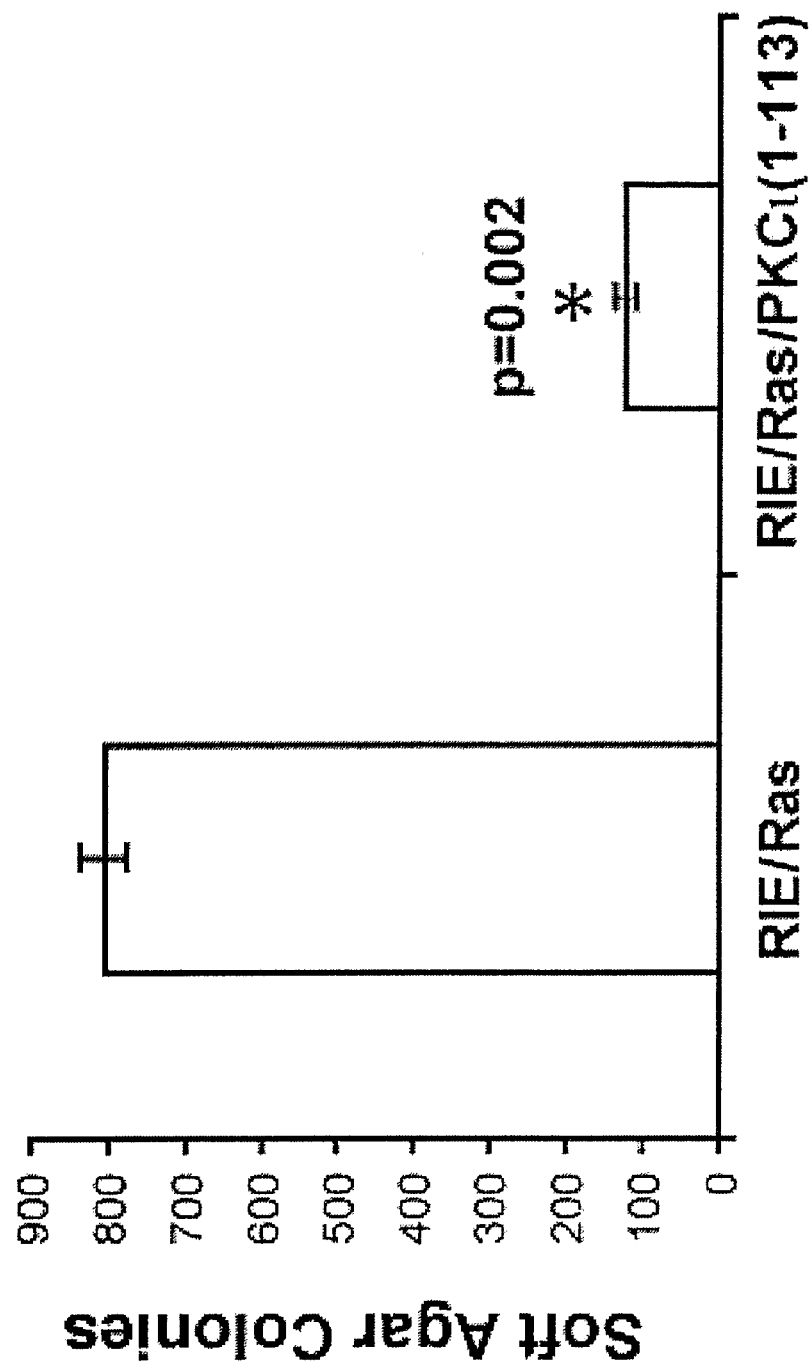
FIG. 9 is a bar graph plotting the number of soft agar colonies by RIE/Ras cells and RIE/Ras/PKCι(1-113) cells. The cells with PKCι(1-113) exhibited significantly less soft agar colony formation than cells lacking PKCι(1-113). These results demonstrate that PKCι(1-113) can block Ras transformation.

Immunoblot analysis and/or immunohistochemistry was used to examine the expression of PKCι polypeptides in samples of human cancers and human cancer cell lines. Elevated expression of PKCι polypeptides was detected in the following cancers: colon, lung, head and neck, ovary, esophagus, prostate, ovary, kidney, and pancreas. More than 80 patient cases of adenocarcinoma and squamous carcinoma of the lung for PKCι expression were analyzed by both immunoblot analysis and immunohistochemistry using tissue arrays. Representative results are shown in FIG. 8. Without exception, these samples exhibited elevated PKCι expression when compared to patient matched normal lung tissue. These results indicate that elevated expression of PKCι can be a common feature of most, if not all, cancers.

Example 6

PKCι and Lung Cancer

Non-small cell lung cancer (NSCLC) is the most common cause of cancer death in the United States. Long-term survival in NSCLC is low, indicating a need for better prognostic and therapeutic tools to detect and treat this disease. PKCι is highly expressed in human non-small cell lung cancer cell lines and primary tumors, and is required for transformed growth of lung cancer cells in vitro and tumorigenicity in vivo. PKCι activates a Rac1→Pak1→Mek1,2→Erk1,2 signaling pathway that regulates lung cancer growth. In addition, the PKCι gene is frequently amplified in lung squamous cell carcinoma cell lines and primary tumors, and PKCι expression predicts poor survival in patients with lung adenocarcinoma.

Methods and Materials

Experimental Procedures Reagents: Antibodies were from the following sources and were used at the indicated concentrations: anti-PKCζ (Santa Cruz #sc-17640; 1:100), PKCι (Transduction Labs #P20520; 1:4000), actin (Santa Cruz #sc-1616; 1:2000), the FLAG epitope (Sigma #A8592; 1:2000), Rac1 (Transduction Labs #610651; 1:3000), cIAP2 (Santa Cruz #sc-7944; 1:500), Bcl-XL (Cell Signaling #2762; 1:1000), PARP/cleaved PARP (Cell Signaling #9542; 1:1000), MEK, Phospho-(Ser217/221)-MEK and Phospho-(Ser298)-MEK (Cell Signaling #9122,9121 and 9128; 1:1000), ERK and Phospho-(Thr202/Tyr204)-ERK (Cell Signaling #9102/9101; 1:1000), CD31 (or Pecam-1; Santa Cruz #sc-1506; 1:1000), and BrdU (DAKO # M0744; 1:100). TUNEL staining was performed using the TdT-FragEL DNA fragmentation detection kit (Calbiochem #QIA33). Recombinant human PKCι and PKCζ polypeptides were obtained from Upstate Biochemical (#14-505 and #14-525, respectively). The myristoylated atypical PKC pseudosubstrate inhibitor peptide was obtained from Biosource (#77-749).

Cell Culture, Plasmids, Transfections and Drug Treatments: Human A549, ChaGo-K-1, H292, H520, H1299, and SK-MES-1 non-small cell lung cancer cell lines as well as the non-transformed HBE4 lung epithelial cell line were obtained from ATCC (Manassas, Va., USA) and maintained as suggested by the supplier. The cells were maintained in a humidified tissue culture incubator at 37° C. in 5% $CO_2$. A549, H1299, and ChaGo-K-1 cells were stably transfected with recombinant pBabe retroviruses containing Flag-tagged human full-length wild-type PKCι (wtPKCι), kinase dead PKCι (kdPKCι), or empty vector as described previously (Lu et al., *Oncogene*, 20:4777-4792 (2001)). Expression of FLAGepitope-tagged PKCι and total PKCι was analyzed by immunoblot analysis as described previously (Murray et al., *J. Cell Biol.*, 164:797-802 (2004)).

Adherent growth kinetics of A549 and H1299 cells transfected with empty pBabe, pbabe/kdPKCι, or pbabe/wtPKCι were determined by plating cells ($1 \times 10^4$ cells/well) into multi-well culture dishes and monitoring cell growth daily over a seven day period. Each day, cells from triplicate wells were trypsinized and counted using a hemocytometer. In some experiments, A549 cells were maintained in medium containing either 10%, 2%, or no fetal bovine serum.

Cell Invasion and Soft Agar Growth Assays: A549 and H1299 transfectants were assayed for cell invasion using Matrigel-coated Transwell cell culture chambers (6,5-mm diameter, 8-μm pore size; BD Biosciences). A549 and H1299 cell transfectants in logarithmic growth phase were harvested with trypsin, the trypsin neutralized with serum-containing medium, and the cells pelleted and resuspended in serum-free growth medium. $2.5 \times 10^4$ cells were placed into the upper chamber of the Transwell insert, and growth medium containing 10% FBS was added to the lower chamber. After 22 hours at 37° C. in 5% $CO_2$, non-invasive cells in the upper chambers were removed and invasive cells were fixed in 100% methanol and stained with 0.5% crystal violet (Sigma) in 2% ethanol. Cells which had invaded through the Matrigel-coated filter were counted on a microscope (X40, Olympus) using a calibrated ocular grid.

Anchorage-independent growth was assayed by the ability of cells to form colonies in soft agar. The bottom agar consisted of growth medium containing 10% FBS and 0.75% agarose in 60-mm tissue culture dishes. Nine hundred cells were resuspended in growth medium containing 10% FBS and 0.75% agarose, and plated on top of the bottom agar. The cells were incubated at 37° C. in 5% $CO_2$. Cell colonies were visualized and quantified under a dissecting microscope (Olympus) after 4-6 weeks in culture.

Rac 1 Activity Assays: Rac1 activity in A549 and H1299 cell transfectants was assessed by affinity isolation of GTP-bound Rac1 using binding domains of PAK as described previously (Sander et al., *J. Cell Biol.*, 143(5):1385-98 (1998)). Briefly, cells were lysed in lysis buffer (50 mM Tris-HCl pH 7.5, 150 mM NaCl, 20 mM $MgCl_2$, 5 mM EGTA, 10% glycerol, 1% Triton X-100, 1% NP-40, 25 mM NaF, 1 mM phenylmethylsulfonyl fluoride, 1 mM sodium orthovanadate, 10 µg/ml leupeptin, 10 µg/ml aprotinin) at 4° C. for 5 min. Cellular debris was removed by centrifugation at 20,000×g for 5 min, and supernatants were transferred to new tubes containing 20 µl of GST-p21-binding domain of PAK1 (PAK1-PBD) coupled to agarose beads (Upstate). An aliquot of each supernatant was reserved to determine total Rac1 and actin expression by immunoblot analysis. Following a 30-minute incubation at 4° C., the agarose beads were collected by centrifugation and washed three times in wash buffer (50 mM Tris-HCl pH 7.5, 150 mM NaCl, 20 mM $MgCl_2$, 5 mM EGTA, 10% glycerol, 1% Triton X-100, 1% NP-40, 25 mM NaF, 1 mM phenylmethylsulfonyl fluoride, 1 mM sodium orthovanadate, 10 µg/ml leupeptin, 10 µg/ml aprotinin). Bound polypeptides were solubilized by the addition of 30 µl of SDS sample buffer, resolved by SDS-PAGE, and subjected to immunoblot analysis for Rac1. An equivalent aliquot of the total cell lysate was subjected to immunoblot analysis to determine total Rac1 expression.

NF-κB Transcriptional Activity Assays: NF-κB transcriptional activity was assayed using a dual-luciferase reporter system (Promega) as described previously (Lu et al., *Oncogene*, 20:4777-4792 (2001)). In brief, A549 cells stably expressing kdPKCι or pBabe vector control were transiently transfected with 500 ng of 3×MHCLuc, a plasmid containing three NF-κB response elements from the MHC promoter linked to a luciferase reporter gene, and 25 ng of phRL-SV40 using the FuGene6 lipofection reagent (Roche Applied Science) as described by the manufacturer. Twenty four hours after transfection, NF-κB activity was stimulated with 50 ng/ml TNFα (R&D Systems) for 2 hours. Total cell extracts were prepared for the dual-luciferase assay according to manufacturer's (Promega) instructions. Firefly and *Renilla* luciferase activity were measured using a Veritas Microplate Luminometer (Turner BioSystems). The activity of *Renilla* luciferase was used as an internal control for transfection efficiency.

Tumorigenicity in Nude Mice: The growth of stably infected A549 human lung carcinoma cells as established subcutaneous tumors was studied in athymic nude mice (Harlan-Sprague-Dawley, Indianapolis, Ind.) in a defined pathogen-free environment. Briefly, A549 cell transfectants were grown in F-12K Nutrient Mixture containing 10% FBS. A549 cell transfectants were harvested and resuspended in serum-containing medium. 4-6 week old female nude mice were injected subcutaneously into the flank with $5 \times 10^6$ cells in 100 µl of growth medium. Once palpable tumors were established, tumor size was measured once a week. Tumor growth was quantified by measuring the tumors in three dimensions with calipers. Tumor volume ($mm^3$) was calculated using the formula: 0.5236 (L×W×H), where L represents the length of the tumor, W represents the width of the tumor, and H represents the height of the tumor. Animals were individually monitored throughout the experiment. At the conclusion of the study, mice were injected intraperitoneally with 100 µg/g of 5-bromo-2-deoxyuridine (BrdU) 1 hour prior to sacrificing the mice by $CO_2$ asphyxiation. Tumors were excised and divided into sections for protein extraction and tumor fixation. Total tumor extracts were prepared in SDS buffer [2% (w/v) SDS, 4 M urea, 62.5 mM Tris-HCl (pH 6.8), 1 mM EDTA, 5% (v/v) β-mercaptoethanol] and equal amounts of polypeptide were subjected to immunoblot analysis as described herein. A section of tumor was also fixed in 10% buffered formalin, embedded in paraffin, sectioned (5 µm thickness), and stained for appropriate antigens.

Immunoblot Analysis: Cells were harvested by washing with PBS and scraping off the plate. The cell pellet was lysed in SDS sample buffer. Protein lysates were quantitated by using the nitration of tyrosine in nitric acid (Bible et al., *Anal. Biochem.*, 267(1):217-21 (1999)). Equal amounts of protein (~20 µg) were loaded for each sample, resolved in 12% or 4-20% SDS-PAGE gels (Invitrogen) and transferred to PVDF membrane (Millipore Immobilin-P). A solution of 5% milk and PBS-Tween 20 was used for blocking. TBS-Tween 20 was used for phospho-specific antibodies. Western blot analysis was performed with appropriate antibodies and detected using ECL-Plus (Amersham).

Analysis of Human Lung Cancer Tissues: H&E stained sections of matched normal and lung tumor tissues were analyzed by a pathologist in order to confirm initial diagnosis, staging, and overall integrity of the tissue samples. Based on this analysis, 40 cases of squamous cell carcinoma of the lung, 40 cases of adenocarcinoma of the lung, and matched normal lung tissues were chosen for extraction of DNA, RNA, and protein. Ten 10 µm thick slices were cut from each frozen block. DNA was isolated in phenol/chloroform, total RNA was isolated using RNAqueous 4PCR kit (Ambion), and protein was isolated by direct solubilization in SDS-PAGE sample buffer.

Real Time PCR Analysis for PKCι Gene Amplification: Genomic DNA from each sample was analyzed for amplification of PKCι using TaqMan technology on an Applied Biosystems 7900HT sequence detection system. The human RNaseP1 gene was used as a DNA template control and for normalization of results to total DNA. The primer/probe set for the human PKCι gene was as follows: forward primer, 5'-GGC-TGCATTCTTGCTTTCAGA-3' (SEQ ID NO:9); reverse primer, 5'-CCAAAAATA-TGAAGCCCAG-TAATCA-3' (SEQ ID NO:10); and probe: 5'-CAATCTTAC-CTG-CTTTCT-3' (SEQ ID NO:11). The primer/probe set for the RNAseP1 gene was designed and provided by ABI Assay on Demand.

Real-time Reverse Transcriptase-PCR Analysis of PKCι mRNA Abundance: PKCι mRNA abundance was determined by real-time Reverse Transcriptase-PCR using TaqMan technology on Applied Biosystems 7900HT sequence detection system. Human glyceraldehyde-3-phosphate dehydrogenase was used as an endogenous control. Samples were subjected to RT-PCR in the absence of reverse transcriptase controlled for the presence of genomic DNA. The primer/probe set for human PKCι mRNA spans the exon 16/17 border and was as follows: forward primer, 5'-CGTTCTTCCGAAATGT-TGAT-TG-3' (SEQ ID NO:12); reverse primer, 5'-TCCCCA-GAAATATTTGGTTTAAAGG-3' (SEQ ID NO:13); and probe, 5'-TTGCTCCATCATATCC-3' (SEQ ID NO:14).

Analysis of PKCι Polypeptide Expression: Polypeptides from human tumor samples was quantified using nitric acid mediated nitration of tyrosine (Bible et al., *Anal. Biochem.*, 267(1):217-21 (1999)). Equal amounts of polypeptide (~30 µg) from each sample was resolved in 12% SDS-PAGE gels (Invitrogen), transferred to PVDF membrane (Millipore Immobilin-P), and subjected to immunoblot analysis using the appropriate antibodies and ECL-Plus detection (Amersham) as described previously (Murray et al., *J. Cell Biol.*, 164:797-802 (2004) and Zhang et al., *J. Biol. Chem.*, 279, 22118-22123 (2004)). Images were obtained on X-omat AR film, and antigens quantified by fluorescence detection using a Typhoon 9410 Variable Mode Imager. The fluorescent signal was analyzed using ImageQuant 5.2 software (Amersham).

Immunohistochemistry was performed on paraffin embedded sections of primary tumor and normal lung tissues. The tissue was deparaffinized by placing slides into 3 changes of xylene and rehydrated in a graded ethanol series. The rehydrated tissue samples were rinsed in water and subjected to antigen retrieval in citrate buffer pH 6.0 as described by the manufacturer (Dako). Slides were treated with 3% $H_2O_2$ for five minutes to reduce endogenous peroxidase activity and washed with PBS containing 0.5% (w/v) Tween 20. PKCι was detected using PKCι antibody at a 1:100 dilution in PBS/Tween and visualized using the Envision Plus Dual Labeled Polymer Kit following the manufacturer's instructions (Dako). Images were captured and analyzed using ImagePro software.

Statistical and Survival Analysis: Cancer-specific survival was estimated using the Kaplan-Meier method. The duration of follow-up was calculated from the sample date to the date of death or last follow-up. The associations of the clinical and pathologic features studied with death from lung cancer were assessed using Cox proportional hazards regression models and summarized with risk ratios and 95% confidence intervals (CI). Natural logarithmic transformations were explored if the distributions of continuously scaled variables were not approximately normal. In addition, the relationships between continuously scaled variables and death from lung cancer were investigated using martingale residuals from the Cox model (Therneau et al., Modeling Survival Data Extending the Cox Model. First edition. Ami Arbor, Springer-Verlag, (2000)). Statistical analyses were performed using the SAS software package (SAS Institute; Cary, N.C.) and p-values <0.05 were considered statistically significant.

Results

Figure 10:
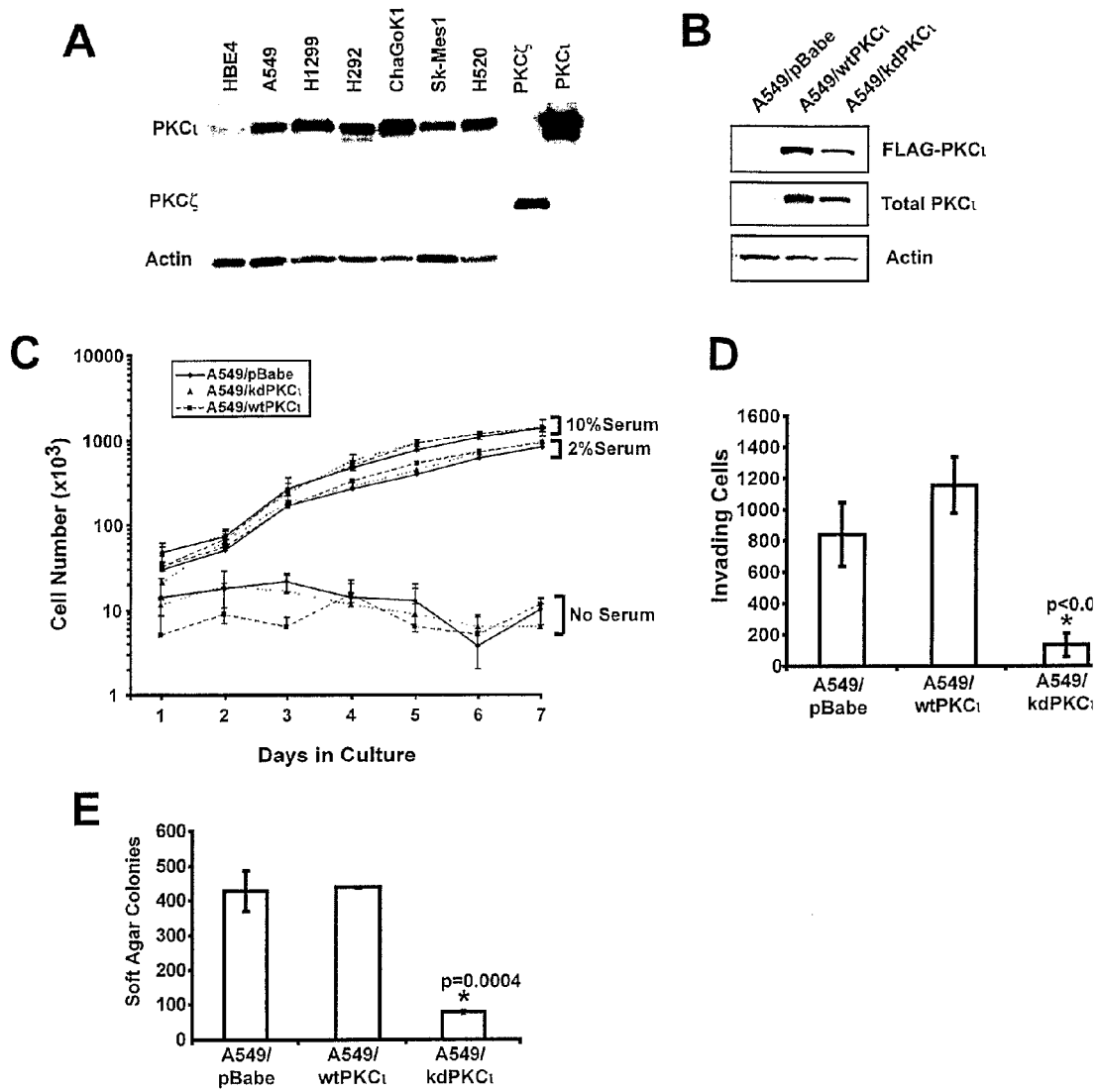

Atypical PKCι Expression is Elevated in Human NSCLC Cells: The expression of PKCι and PKCζ in established human NSCLC cell lines was assessed. Immunoblot analysis of total cell lysates from six human NSCLC cell lines (A549, H1299, H292, ChaGoK1, Sk-Mes1, and H520) revealed that each cell line expressed elevated levels of PKCι when compared to non-transformed human HBE4 lung epithelial cells (FIG. 10A). In contrast, none of the cell lines expressed detectable levels of PKCζ. Purified recombinant human PKCι and PKCζ were included in the immunoblot analyses to ensure the specificity and activity of the antibodies for their respective antigens. Quantitative real time PCR analysis of isolated RNA revealed an increase in PKCι mRNA abundance in each of the NSCLC cell lines compared to HBE4 cells. In contrast, PKCζ mRNA was detected at much lower levels in each cell line and was not elevated in NSCLC cell lines. Thus, PKCι is the major, and perhaps the only atypical PKC isozyme expressed in non-transformed lung epithelial and NSCLC cells, and PKCι expression is elevated in NSCLC cell lines when compared to non-transformed lung epithelial cells.

PKCι is Required for Human NSCLC Cell Transformation in vitro: Having identified PKCι as the major atypical PKC isozyme expressed in human NSCLC cell lines, the role of PKCι in the transformed phenotype exhibited by lung cancer cells was examined. A549 cells, a commonly studied LAC cell line, were stably transfected with retroviruses expressing either wild type human PKCι (wtPKCι), a kinase deficient PKCιmutant (kdPKCι) which acts in a dominant negative fashion (Jamieson et al., J. Biol. Chem., 274, 3927-3930 (1999) and Murray et al., J. Cell Biol., 164:797-802 (2004)), or empty retroviral vector (pBabe). Immunoblot analysis using an anti-Flag antibody confirmed expression of the appropriate recombinant PKCι polypeptides and a PKCι-specific antibody monitored total PKCι polypeptide expression (FIG. 10B). No significant change in growth rate, saturation density, or survival was observed in any of the A549 cell transfectants grown in adherent culture in 10% serum, 2% (reduced) serum, or in the absence of serum (FIG. 10C). Thus, PKCι signaling does not appear to be important for growth or survival of A549 cells in adherent culture.

Despite having no effect on adherent growth or survival of A549 cells, expression of kdPKCι had a dramatic inhibitory effect on several aspects of the transformed phenotype of A549 cells. Thus, A549/pBabe and A549/wtPKCι cells exhibited a highly invasive phenotype as measured by invasion through Matrigel-coated chambers, whereas A549/kdPKCι cells showed a significantly reduced invasive potential (FIG. 10D). Similarly, both A549/pBabe and A549/wtPKCι cells form abundant colonies in soft agar, whereas A549/kdPKCι cells exhibit a significant impairment in anchorage-independent growth (FIG. 1E). Thus, PKCι appears to be involved in the transformed phenotype of A549 cells and cellular invasion and anchorage-independent growth.

Figure 11:
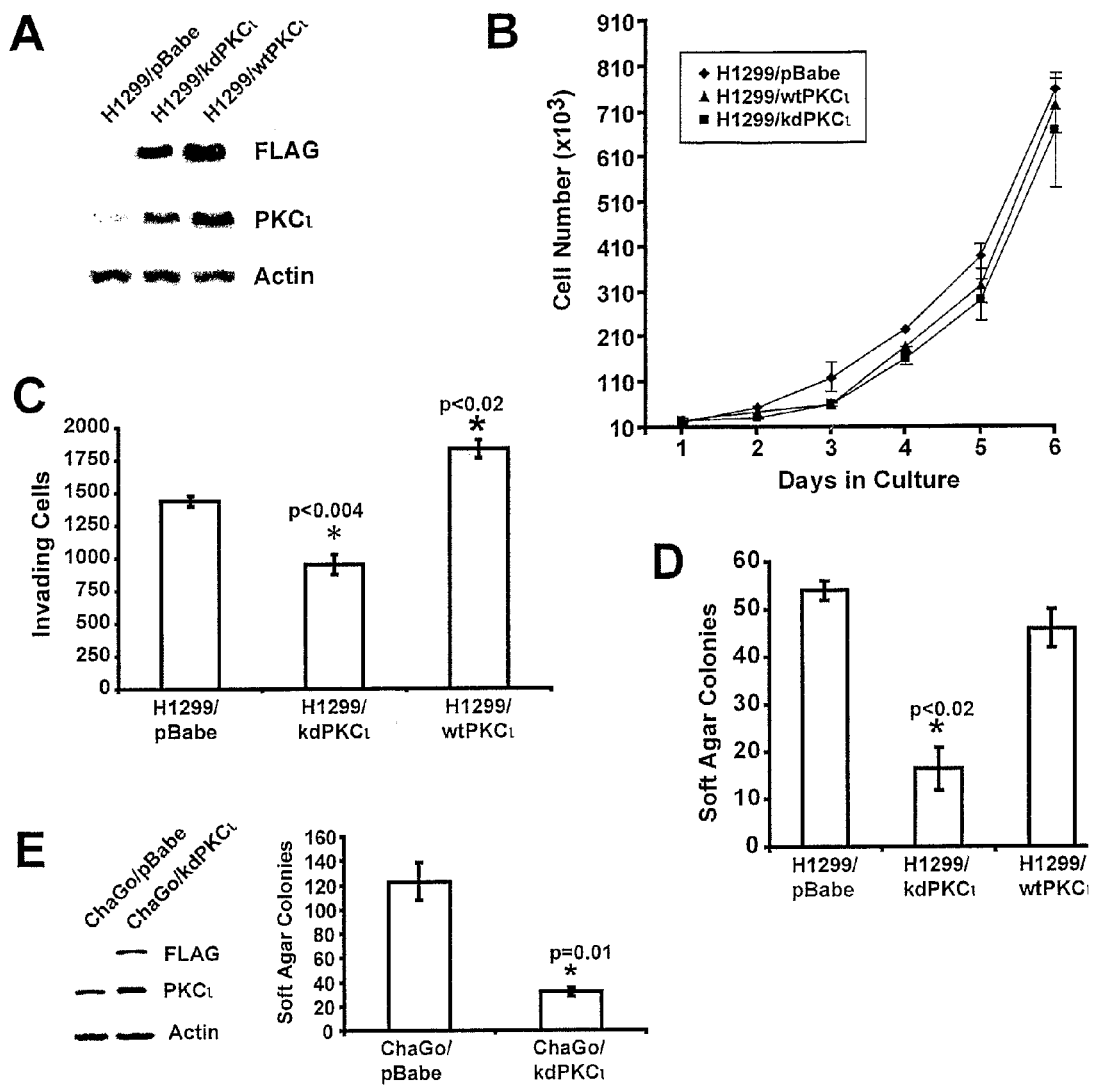
FIG. 11A contains a photograph of an immunoblot analysis of H1299 cells stably transfected with pBabe, kdPKCι, or wtPKCι for Flag, PKCι, or actin.
FIG. 11B is a graph plotting the growth kinetics of H1299 cell transfectants in adherent culture in the presence of 10% serum.
FIG. 11C is a bar graph plotting the number of H1299 cell tranfectants invading through Matrigel coated chambers.
FIG. 11D is a bar graph plotting the number of colonies formed by anchorage-independent growth of H1299 cell transfectants in soft agar.
FIG. 11E contains a photograph of an immunoblot analysis of ChaGoK cells stably transfected with empty pBabe or kdPKCι for Flag, PKCι, and actin.

To assess whether the effects of kdPKCι on transformation were specific to A549 cells, H1299 cells, a SCC cell line, stably expressing either wtPKCι or kdPKCι were established (FIG. 11A). Consistent with the results in A549 cells, expression of either wtPKCι or kdPKCι had no effect on anchorage-dependent cell growth of H1299 cells (FIG. 11B). However, kdPKCι significantly inhibited both cellular invasion (FIG. 11C) and anchorage-independent growth of H1299 cells in soft agar (FIG. 11D), whereas wtPKCι had little or no effect. Expression of kdPKCι in ChaGoK1 cells, another SCC cell line, resulted in a similar inhibition of transformed growth in soft agar (FIG. 11E). Therefore, PKCι signaling is involved in the transformation of both SCC and LAC, and is not peculiar to A549 cells.

Figure 12:
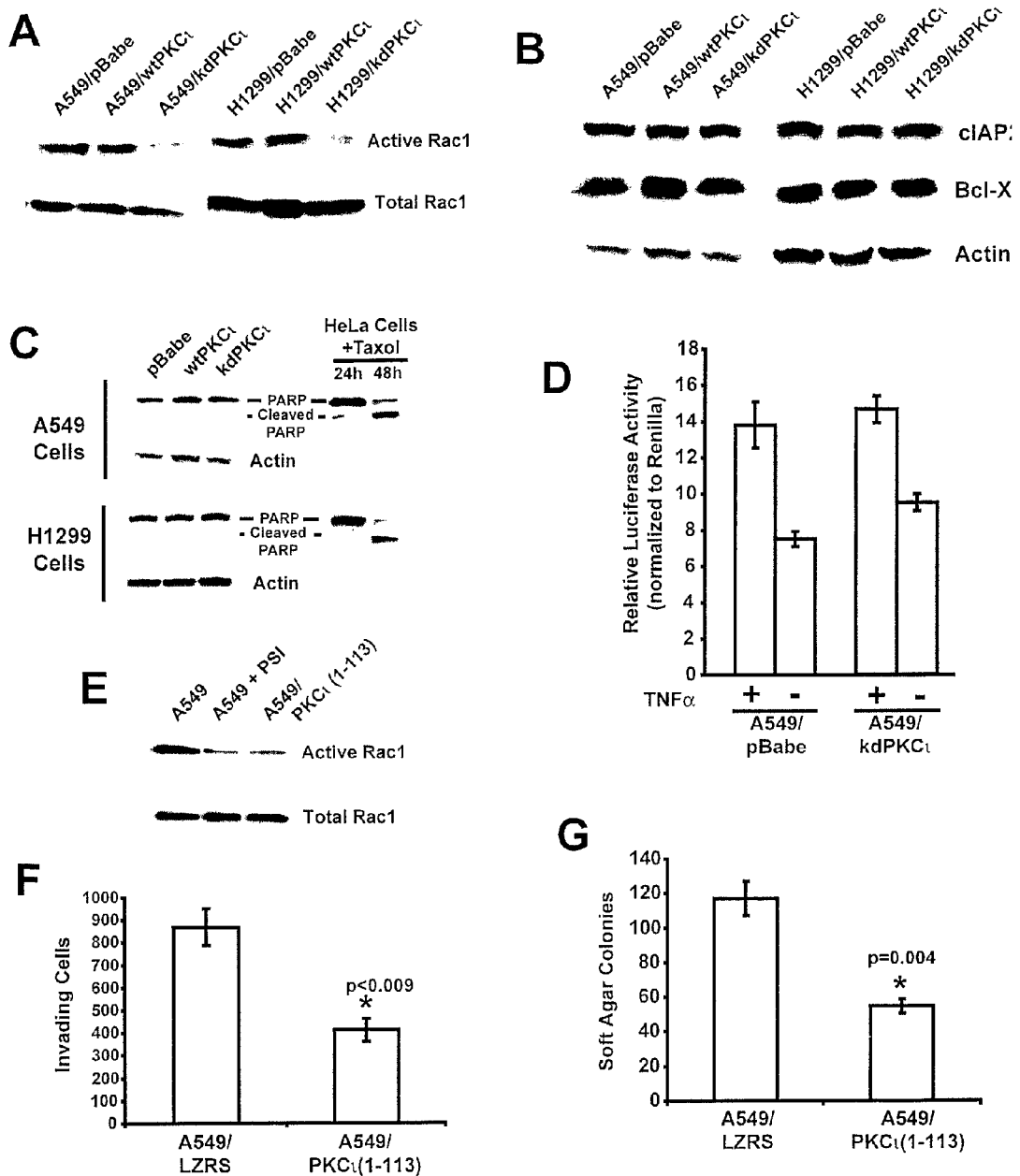
FIG. 12A contains a photograph of active GTP-bound Rac1 and total Rac1 expression in A549 and H1299 cell transfectants.
FIG. 12B contains a photograph of an immunoblot analysis of A549 and H1299 cell transfectants for cIAP2, Bcl-XL, and actin.
FIG. 12C contains a photograph of the analysis of A549 and H1299 cell transfectants for PARP and cleaved PARP. HeLa cells treated with taxol for either 24 or 48 hours served as a positive control.
FIG. 12D is a bar graph plotting transcriptional activity of an NF-κB-luciferase reporter in A549/pBabe and A549/kdPKCι cells in the presence and absence of TNFα.
FIG. 12E contains a photograph of active and total Rac1 expression assessed in parental A549 cells, A549 cells treated with the PKCι-selective pseudosubstrate peptide inhibitor (PSI), and A549 cells expressing the PB1 domain of PKCι (PKCι(1-113)).
FIG. 12F is a bar graph plotting the number of A549/LZRS and A549/PKCι(1-113) cell transfectants invading through Matrigel coated chambers.
FIG. 12G is a bar graph plotting the number of colonies formed by anchorage-independent growth of A549/LZRS and A549/PKCι(1-113) cell transfectants in soft agar.

Rac1 is a Downstream Target of PKCι in Lung Cancer Cell Transformation: The relative importance of Rac1 and NF-κB in mediating PKCι-dependent transformation of NSCLC cells was assessed (FIG. 12). Both A549/pBabe and H1299/pBabe cells exhibited significant Rac1 activity, as assessed by the level of GTP-bound Rac1, which is inhibited by the expression of kdPKCι but not wtPKCι (FIG. 12A). These results are consistent with the results from Ras-transformed RIE cells which exhibited a similar inhibition of Rac1 activity by kdPKCι expression (Murray et al., J. Cell Biol., 164:797-802 (2004)).

The involvement of NF-κB signaling in PKCι-dependent transformation was also assessed. NF-κB plays a role in the protection of NSCLC cells from apoptosis through direct transcriptional induction of expression of the antiapoptotic genes cIAP2 and Bcl-XL (Cheng et al., Oncogene, 19, 4936-4940 (2000); Jiang et al., Oncogene, 20, 2254-2263 (2001); and Webster et al., Endocrinology, 143, 3866-3874 (2002)). Neither wtPKCι nor kdPKCι had an effect on the steady-state levels of cIAP2 or Bcl-XL in either A549 or H1299 cells (FIG. 12B). Furthermore, neither wtPKCι nor kdPKCι induced apoptosis in A549 or H1299 cells as measured by caspase-mediate cleavage of PARP (FIG. 12C) or trypan blue exclusion viability analysis. Inhibition of NF-κB transcriptional activity in A549 and H1299 cells induces apoptosis (Jiang et al., Oncogene, 20, 2254-2263 (2001)). Direct measurement of NF-κB transcriptional activity revealed that A549 cells exhibited significant basal and TNFα-stimulated NF-κB activity that is not affected by expression of kdPKCι (FIG. 12D). Taken together, these results demonstrate that PKCι regulates Rac1 activity in A549 and H1299 cells. However, PKCι does not appear to be required for NF-κB signaling in these cells.

These results are interesting in light of the results obtained in other cell systems. For instance, in CML cells, PKCι is required for Bcr-Abl-mediated transformation and NF-κB was identified as a requisite downstream effector of PKCι-dependent cell survival (Jamieson et al., *J. Biol. Chem.*, 274, 3927-3930 (1999); Lu et al., *Oncogene*, 20:4777-4792 (2001); and Murray et al., *J. Biol. Chem.*, 272, 27521-27524 (1997)). In contrast, in rat intestinal epithelial (RIE) cells, the small molecular weight GTPase Rac1 was identified as a downstream effector of oncogenic Ras-mediated, PKCι-dependent transformation (Murray et al., *J. Cell Biol.*, 164:797-802 (2004)). Thus, it appears that PKCι can contribute to transformation through activation of at least two different signaling pathways depending upon the cellular context.

The PB1 Domain is Involved in PKCι-dependent Transformation: The ability of kdPKCι to block Rac1 activity suggests that the kinase activity of PKCι is required for Rac1 activation in NSCLC cells. Treatment of A549 cells with the highly selective cell permeant atypical PKC pseudosubstrate peptide inhibitor, PSI, also blocks Rac1 activity (FIG. 12E), confirming the involvement of PKCι activity in Rac1 activation. PKCι regulates Rac1 through PB1 domain-mediated complex formation between PKCι, Rac1, and the adapter protein Par6 (Etienne-Manneville et al., *Curr. Opin. Cell Biol.*, 15, 67-72 (2003)). It is possible that expression of the PB1 domain of PKCι would act as a competitive inhibitor of PKCι-mediated activation of Rac1. Indeed, A549 cells stably transfected with a plasmid containing the first 113 amino acids of PKCι, PKCι(1-113), which encompasses the PB1 domain of the PKCι, inhibits Rac1 activity (FIG. 12E). Furthermore, expression of PKCι(1-113) inhibits both A549 cell invasion (FIG. 12F) and anchorage-independent growth in soft agar (FIG. 12G), indicating the involvement of the PB1 domain in PKCι-dependent activation of Rac1 and cellular transformation.

Figure 13:
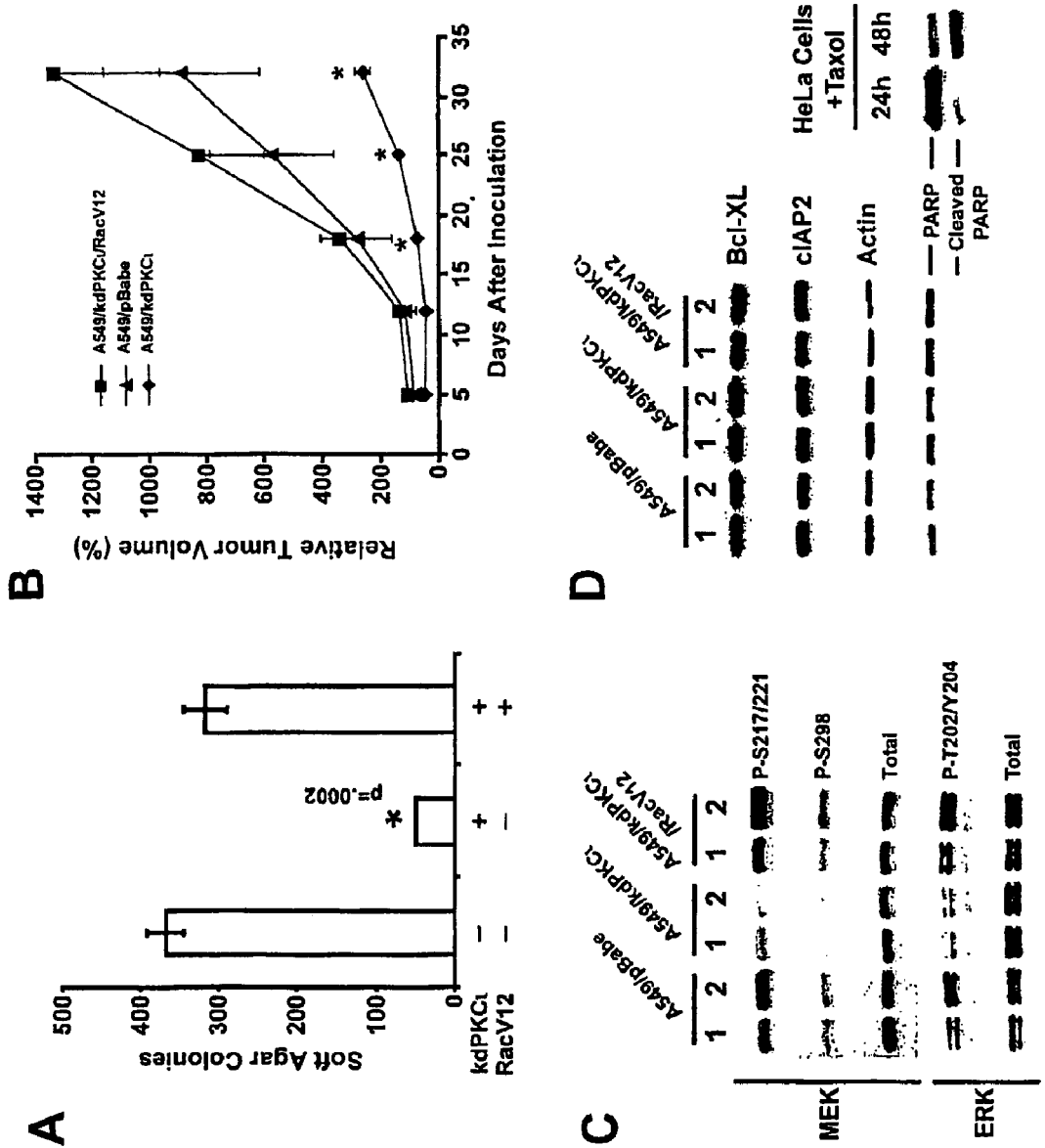
FIG. 13A is a bar graph plotting the number of colonies formed by anchorage-independent growth of A549/pBabe, A549/kdPKCι, and A549/kdPKCι/RacV12 cell transfectants in soft agar.
FIG. 13B is a graph plotting the tumorigenic growth of A549 cell transfectants as subcutaneous xenografts in nude mice.
FIG. 13C is a photograph of an immunoblot analysis of A549 cell transfectants grown as xenografts in nude mice for phospho-Ser217/221 MEK, phospho-Ser298 MEK, total MEK, phosphor-Thr202/Tyr204 ERK 1/2, and total ERK 1/2.
FIG. 13D contains a photograph of an immunoblot analysis of A549 transfectants grown as xenografts in nude mice for Bcl-XL, cIAP2, actin, and PARP/cleaved PARP. Taxol-treated HeLa cells were included as a positive control for cleaved PARP.

The PKCι-Rac1 Signaling Axis is Required for Lung Cancer Cell Tumorigenicity in vivo: Since Rac1 was identified as a molecular target for PKCι in NSCLC cells, Rac1 was assessed for the ability to be a downstream effector of PKCι-dependent transformation. Expression of a constitutively active mutant of Rac1, RacV12, restores transformed growth of A549/kdPKCι cells in soft agar (FIG. 13A). Thus, Rac1 appears to be both necessary and sufficient for PKCι-dependent transformation in vitro. The involvement of the PKCι-Rac1 signaling axis in A549 cell tumorigenicity was assessed in vivo. Athymic nude mice were inoculated subcutaneously with A549/pBabe, A549/kdPKCι, or A549/kdPKCι/RacV12 cells, and tumor growth was assessed over time. Expression of kdPKCι in A549 cells resulted in significant inhibition of tumor growth in vivo, whereas tumor growth was restored to levels indistinguishable from A549/pBabe cells by expression of RacV12 in A549/kdPKCι cells (FIG. 13B). Taken together, these results demonstrate the involvement of the PKCι-Rac1 signaling axis in A549 tumorigenicity in vivo.

The status of Rac1 and NF-κB signaling in tumors derived from A549 cell transfectants was also assessed. Rac1 activity in A549 cell tumors was measured by monitoring the level of activity of the downstream Rac1 effector MEK 1/2. MEK 1/2 was demonstrated to be a PKCι- and Rac1-dependent molecular target in Ras-transformed RIE cells (Murray et al., *J. Cell Biol.*, 164:797-802 (2004)). Immunoblot analysis of lysates from A549/pBabe cell tumors revealed significant levels of activated MEK that is phosphorylated on the Ser217/221 Raf activation sites on MEK1/2 (FIG. 13C). Likewise, significant levels of active ERK, phosphorylated on the MEK-specific Thr202/Tyr204 phosphorylation sites, were detected in these tumors, indicating MEK/ERK activation (FIG. 13C). In addition, significant phosphorylation was observed on the PAK1-specific phosphorylation site on MEK1/2, Ser298 in A549/pBabe tumors (FIG. 13C). In contrast, A549/kdPKCι cell tumors exhibit reduced levels of phospho-MEK at both Raf- and Pak1-mediated sites with a concomitant decrease in phospho-ERK levels. A549/kdPKCι/RacV12 cell tumors exhibit phospho Ser217/221-MEK, phospho-Ser298 MEK, and phospho-Thr202/Tyr204-ERK levels indistinguishable from A549/pBabe cells. Taken together, these results demonstrate that PKCι regulates the MEK/ERK pathway in A549 cell tumors in vivo and indicate that a PKCι/Rac1/PAK1/MEK/ERK pathway is involved in A549 cell tumorigenicity.

Though no evidence for PKCι-dependent NF-κB activation in A549 cells was detected in vitro, it was possible that PKCι may be involved in maintenance of NF-κB activity and tumor survival in the in vivo setting. However, immunoblot analysis demonstrated that expression of the NF-κB transcriptional targets cIAP2 and Bcl-Xl were not affected by expression of kdPKCι or RacV12 (FIG. 13D). In addition, no evidence for induction of apoptosis in tumors expressing kdPKCι or RacV12 was found as measured by caspase-mediated cleavage of PARP (FIG. 13D). Likewise, Tunel analysis of A549/pBabe, A549/kdPKCι, and A549/kdPKCι/RacV12 cell tumors revealed very low levels of apoptosis in all tumors (apoptotic index of <0.2%) and no significant difference among the three tumor groups. Thus, it appears unlikely that NF-κB is a critical target for PKCι-dependent tumorigenicity of A549 cells in vivo.

Figure 14:
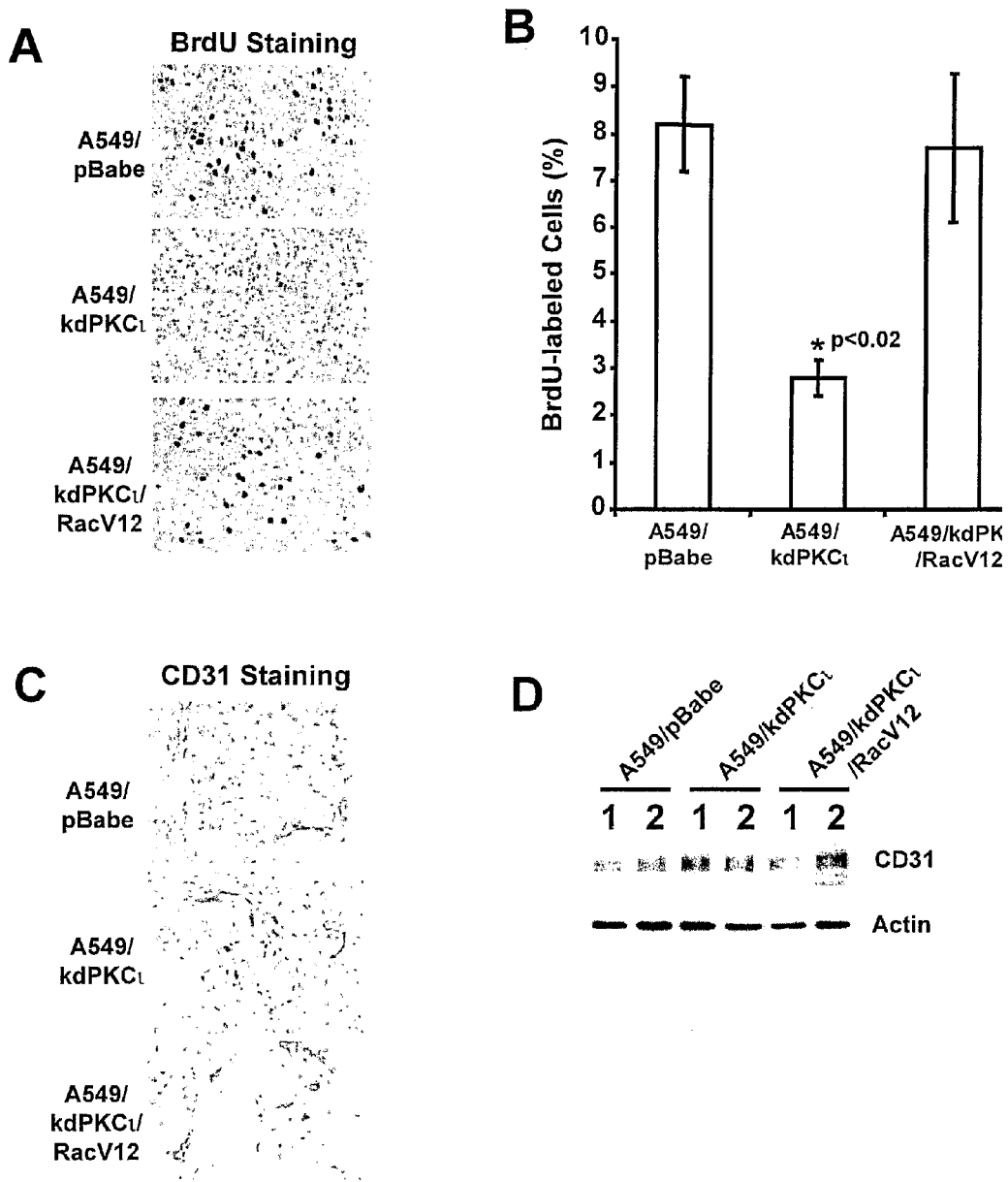
FIG. 14A contains photographs of immunohistochemical staining of A549/pBabe, A549/kdPKCι, and A549/kdPKCι/RacV12 cell tumors for BrdU. Tumor-bearing animals were injected intraperitoneally with BrdU one hour prior to sacrifice.
FIG. 14B is a bar graph plotting the percent of BrdU-labeled cells in A549/pBabe, A549/kdPKCι, and A549/kdPKCι/RacV12 tumors.
FIG. 14C contains photographs of immunohistochemical staining of A549 cell transfectant tumors for the endothelial cell marker, CD31.
FIG. 14D contains a photograph of an immunoblot analysis of A549 cell transfectant tumors for CD31 and actin.

PKCι is Critical for Tumor Cell Proliferation in vivo: The mechanism by which kdPKCι inhibits A549 tumor formation in vivo was assessed. As described herein, induction of apoptosis in A549 cells expressing kdPKCι was not observed, indicating that kdPKCι does not inhibit tumor formation by impairing tumor cell survival. However, BrdU labeling of A549 cell tumors revealed that A549/kdPKCι tumors exhibited a significant decrease in BrdU-positive, cycling tumor cells when compared to A549/pBabe tumors (FIG. 14A). In A549/kdPKCι/RacV12 tumors, the BrdU labeling index is indistinguishable from that of A549/pBabe cell tumors. Quantitative measurement of BrdU-labeled cells revealed a 2.5-3-fold reduction in proliferative index in A549/kdPKCι tumors compared to A549/pBabe tumors that was completely restored by expression of RacV12 (FIG. 14B). Thus, PKCι plays a role in A549 cell tumor proliferation.

It is possible that A549/kdPKCι tumors exhibit a reduced proliferative index due to a reduction in tumor vascularization as a result of decreased angiogenesis. However, immunohistochemical staining with the endothelial cell marker CD31 revealed no change in tumor-associated vessel density in A549 cell tumors in the presence of kdPKCι or RacV12 (FIG. 14C). Immunoblot analysis confirmed that A549/pBabe, A549/kdPKCι, and A549/kdPKCι/RacV12 tumors contained similar levels of CD31 polypeptide (FIG. 14D). Taken together, these results indicate that PKCι is necessary for A549 tumor cell growth by activating a Rac1, PAK1, MEK, ERK signaling pathway while having little or no effect on tumor cell survival or tumor vascularization.

PKCι Expression is Elevated in Primary Squamous Cell Carcinomas: The results provided herein demonstrate that PKCι expression is elevated in NSCLC cells, and that PKCι plays a role in NSCLC cell transformation in vitro and in vivo.

Figure 15:
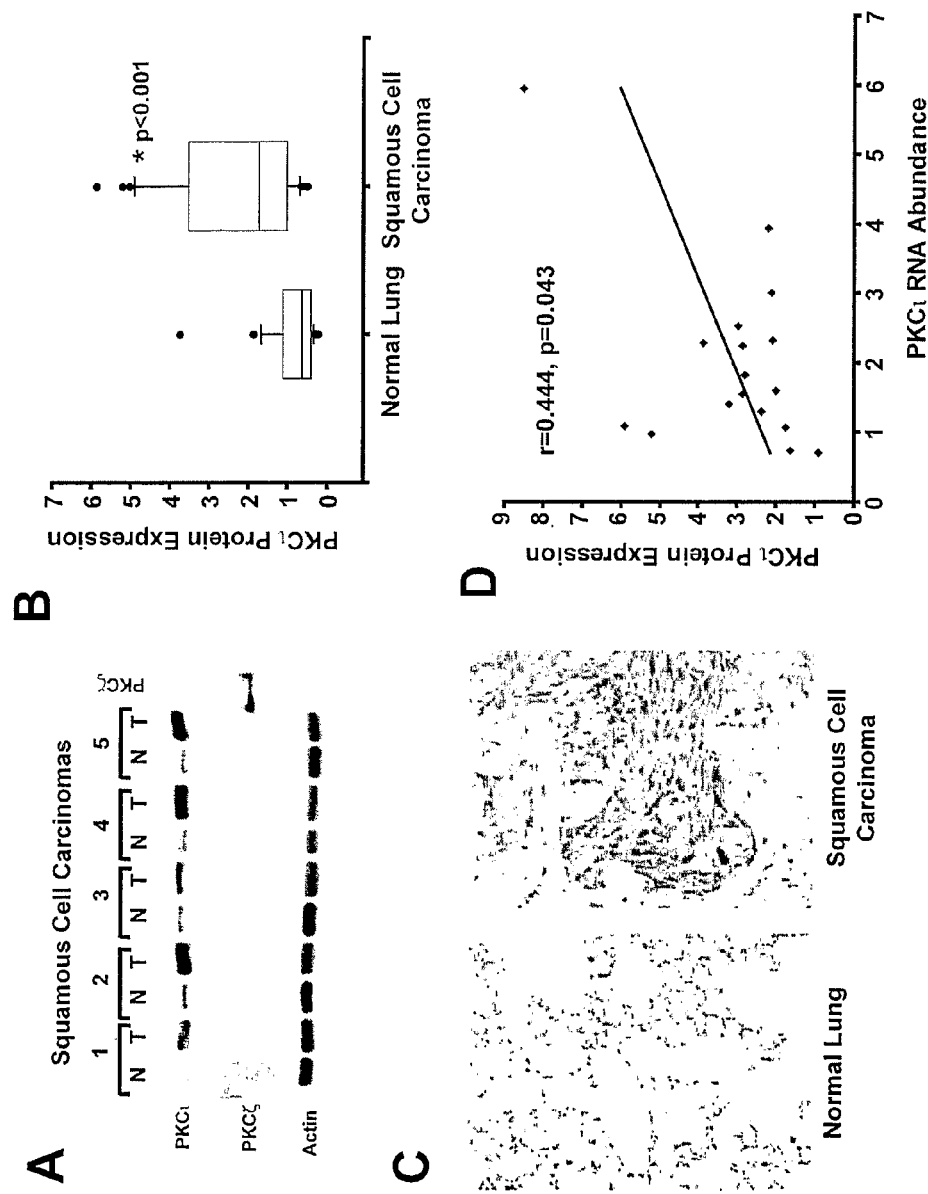
FIG. 15A contains a photograph of immunoblot analysis of primary SCCs and matched normal lung tissue for PKCι, PKCζ, and actin.
FIG. 15B is a bar graph plotting PKCι expression in primary SCCs. 36 cases of primary SCC and matched normal lung tissue were analyzed.
FIG. 15C contains photographs of immunohistochemistry of normal lung and SCC for PKCι.
FIG. 15D is a graph plotting the correlation between PKCι mRNA abundance and PKCι polypeptide expression in SCC.

In order to determine whether PKCι expression is relevant to human disease, atypical PKC expression in the two major sub-types of NSCLC, SCC and LAC, were assessed. Forty cases of SCC and matched normal lung tissues were initially selected for analysis. Three cases had received therapy prior to obtaining the tissue samples and were excluded from the analysis in order to eliminate the possible effect of treatment on PKCι expression. A fourth case was excluded because sufficient protein could not be obtained from both the normal and tumor tissues. The remaining 36 cases were analyzed by immunoblot analysis for expression of PKCι, PKCζ, and actin. Results from five representative cases are shown in FIG. 15A. Elevated PKCι expression was evident in 35/36 (97%) cases when compared to matched normal lung tissue. PKCζ was not detected in any of the tumor or normal lung tissue samples, indicating that PKCι is the predominant atypical PKC expressed in benign and malignant human lung tissue. Real time PCR analysis demonstrated that PKCι mRNA was routinely 10 fold more abundant than PKCζ mRNA in normal and malignant lung tissues, confirming the predominance of PKCι in the human lung.

Quantitative analysis of the immunoblot data demonstrated a statistically significant increase in PKCι expression in SCC compared to normal lung tissue (FIG. 15B). Elevated PKCι was confirmed by immunohistochemistry of all 36 cases contained on tissue microarrays. Light staining for PKCι was observed in normal lung epithelium with intense staining in tumor cells (FIG. 15C). Little or no staining of stromal elements associated with the tumors was observed. PKCι staining was consistent with localization of the enzyme to the cytoplasm, plasma membrane, and nucleus of both normal lung epithelial and tumor cells. No obvious changes in cellular distribution of PKCι were observed between the normal and lung cancer tissues.

Whether PKCι polypeptide expression correlates with PKCι mRNA abundance was assessed in SCC tumors. Total RNA was isolated from 21 SCCs and matched normal samples and assessed for PKCι mRNA abundance by quantitative real time PCR. Spearman rank order analysis demonstrated a positive correlation between PKCι mRNA abundance and PKCι polypeptide expression in SCC (FIG. 15D).

Figure 16:
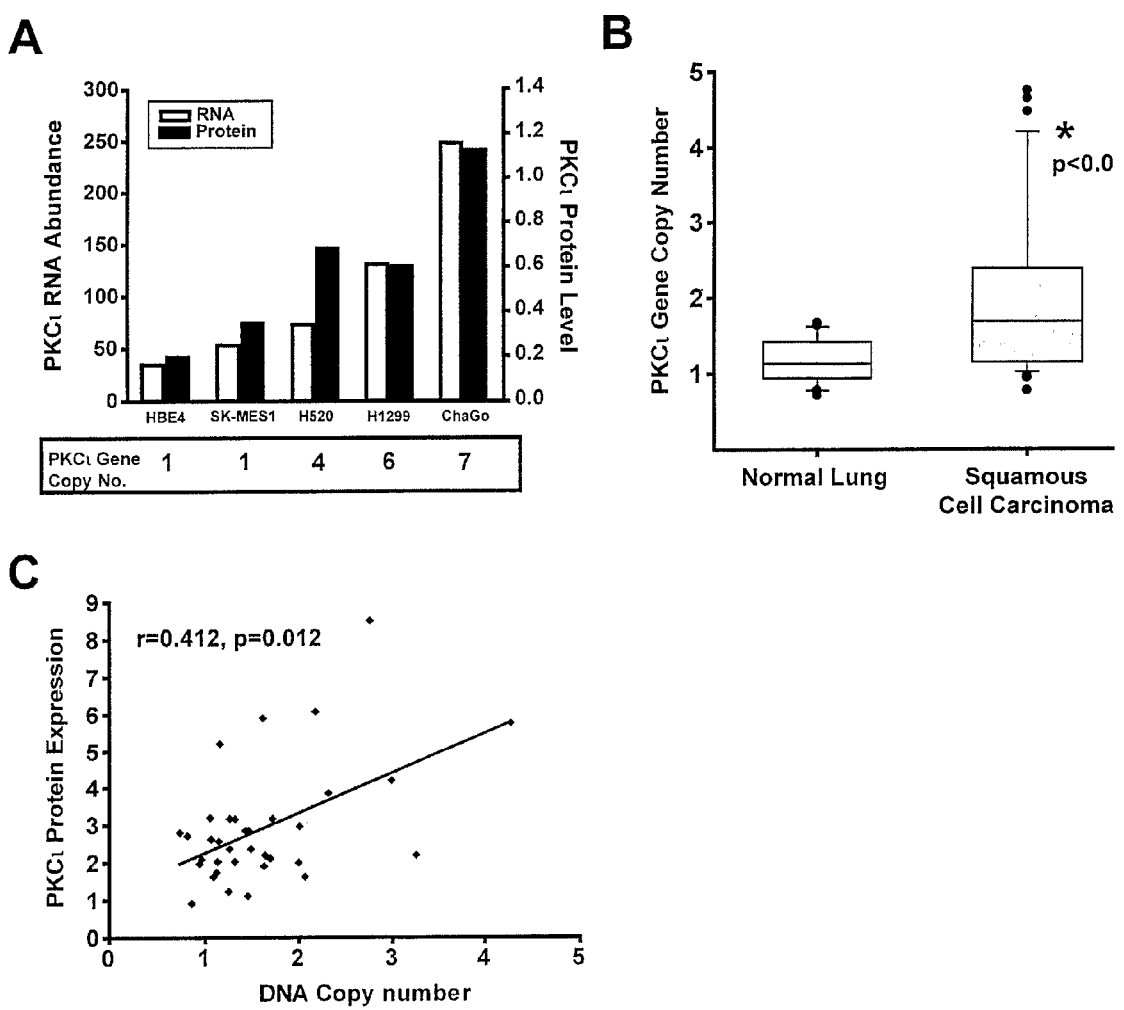
FIG. 16A is a graph of an analysis of human SCC cell lines for PKCι gene copy number, mRNA abundance, and polypeptide expression.
FIG. 16B is a graph plotting PKCι gene copy number for normal lung and primary squamous cell carcinomas.
FIG. 16C is a graph plotting the correlation between PKCι expression and PKCι gene copy number.

PKCι Gene Amplification Regulates PKCι Expression in SCC Cell Lines and Primary SCC Tumors: Among the cytogenetic changes commonly found in lung SCCs, amplification of chromosome 3q26 is among the most frequent, occurring in about 40-50 percent of SCCs (Balsara et al., *Cancer Res.*, 57, 2116-2120 (1997) and Brass et al., *Cancer Res.*, 57, 2290-2294 (1997)). Multiple candidate oncogenes reside in the chromosome 3q26 region including the Ski-like gene SnoN (Imoto et al., *Biochem. Biophys. Res. Commun.*, 286, 559-565 (2001)), the catalytic subunit of phosphatidylinositol-3 kinase (PI3Kα) (Singh et al., *Genes Dev.*, 16, 984-993 (2002)), the Evi1 oncogene (Imoto et al., *Biochem. Biophys. Res. Commun.*, 286, 559-565 (2001)), and the RNA component of human telomerase (TERC) (Yokoi et al., *Clin. Cancer Res.*, 9, 4705-4713 (2003)). However, the importance of these genes in SCC formation has not been systematically evaluated. Since the human PKCι gene resides at 3q26, whether PKCι gene amplification occurs in SCC cell lines and primary tumors was assessed. Quantitative real time PCR analysis revealed PKCι gene amplification in 3 of the 4 established human SCC cell lines tested. Specifically, amplification was detected in H520, H1299, and ChaGo cells, but not in Sk-Mes1 or nontransformed HBE4 lung epithelial cells (FIG. 16A). The presence of PKCι gene amplification was consistent with the presence of chromosome 3q26 amplification reported for these cell lines (Yokoi et al., *Clin. Cancer Res.*, 9, 4705-4713 (2003)), indicating that PKCι is part of the 3q26 amplicon. Quantitative real-time reverse transcriptase PCR and immunoblot analysis revealed a positive correlation between PKCι gene copy number, PKCι mRNA abundance, and PKCι polypeptide expression in these cell lines (FIG. 16A). Taken together, these results demonstrate that PKCι gene amplification occurs frequently in human SCC cell lines, that PKCι resides within the chromosome 3q26 amplicon, and that PKCι gene amplification is a mechanism by which PKCι expression is regulated in SCC cells.

Whether PKCι gene amplification occurs in primary SCC tumors was assessed. Genomic DNA isolated from 36 SCC cases was analyzed for PKCι gene copy number by quantitative real time PCR. Amplification was quantitated by normalizing PKCι gene copy number to the single copy RNAse P gene and standardized to patient-matched normal lung tissue. PKCι gene amplification was observed in 17/36 (47.2%) of the cases. Statistical analysis demonstrated a significant increase in PKCι gene copy number in SCC compared to matched normal lung tissue (FIG. 16B). In addition, Spearman rank order analysis revealed a positive correlation between PKCι gene copy number and PKCι protein expression (FIG. 16C), demonstrating that gene amplification is a mechanism by which PKCι expression is regulated in SCC tumors. This result is consistent with the reported 40-50% frequency of chromosome 3q26 amplification in SCCs (Balsara et al., *Cancer Res.*, 57, 2116-2120 (1997) and Brass et al., *Cancer Res.*, 57, 2290-2294 (1997)). Taken together, these results demonstrate that PKCι expression is elevated in virtually all SCCs, that the PKCι gene is frequently amplified in these tumors, and that the PKCι gene resides within the previously described chromosome 3q26 amplicon. With the functional data showing the involvement of PKCι signaling in lung cancer cell growth and tumorigenicity, these results provide compelling evidence that PKCι is a relevant target for gene amplification with chromosome 3q26 that promotes squamous cell carcinogenesis. Chromosome 3q26 amplification also occurs frequently in SCC of the head and neck (Snaddon et al., *Br. J. Cancer*, 84, 1630-1634 (2001)), esophagus (Imoto et al., *Biochem. Biophys. Res. Commun.*, 286, 559-565 (2001) and Pimkhaokham et al., *Jpn. J. Cancer Res.*, 91, 1126-1133 (2000)), cervix (Sugita et al., *Cancer Genet. Cytogenet.*, 117, 9-18 (2000)) and ovary (Balsara et al., *Cancer Res.*, 57, 2116-2120 (1997) and Sonoda et al., *Genes Chromosomes Cancer*, 20, 320-328 (1997)). Therefore, the PKCι gene appears to be frequently amplified in these tumors as well.

Figure 17:
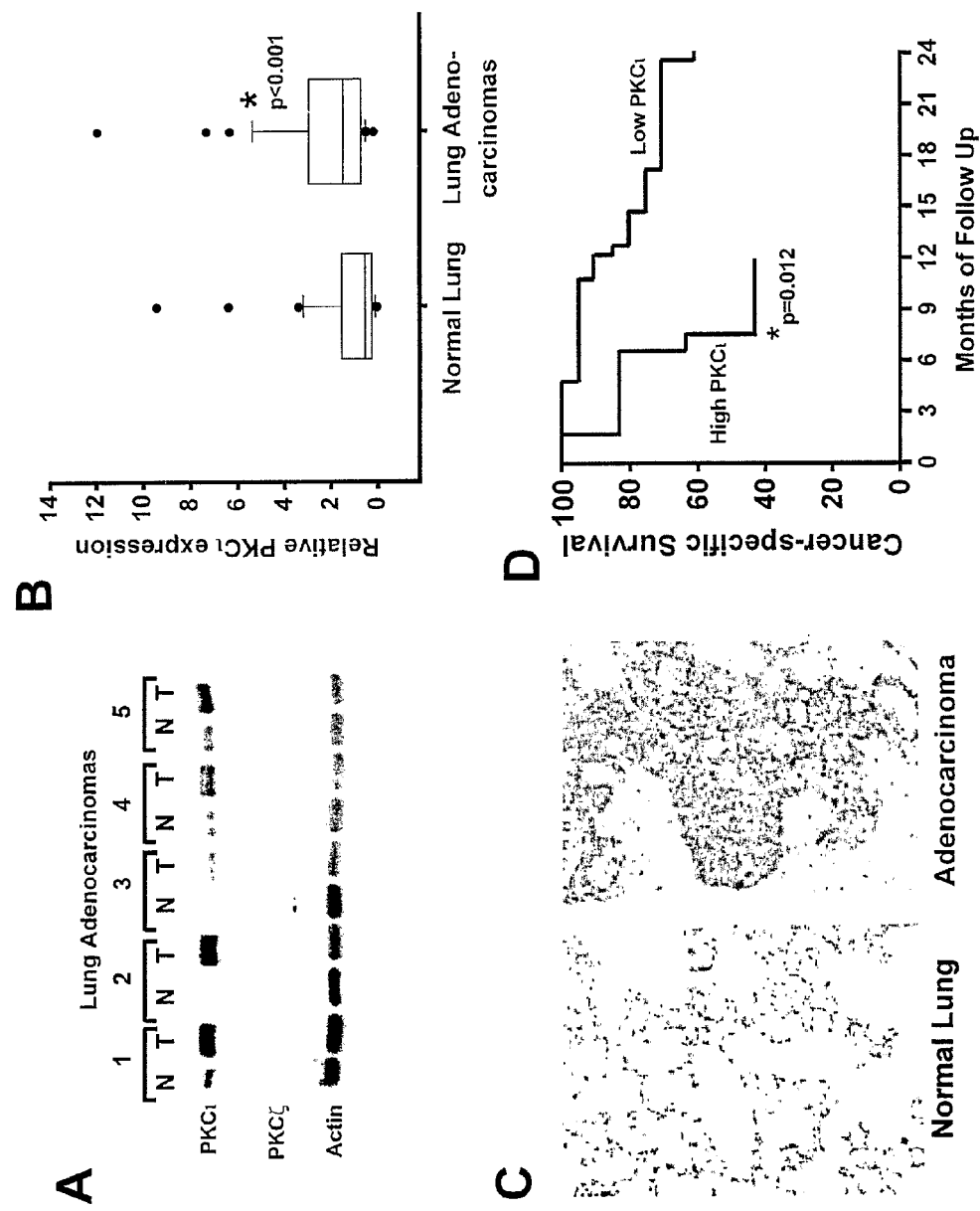
FIG. 17A contains a photograph of an immunoblot analysis of primary lung adenocarcinomas and matched normal lung tissue for PKCι, PKCζ, and actin.
FIG. 17B is graph plotting PKCι expression in normal lung and primary lung adenocarcinomas. 36 cases of primary LAC and matched normal lung tissue were analyzed.
FIG. 17C contains photographs of immunohistochemistry of normal lung and lung adenocarcinoma for PKCι.
FIG. 17D is a graph plotting the Kaplan-Meier survival curve for LAC expressing low versus high PKCι. PKCι expression correlates with poor survival.

PKCι Expression is Elevated in Lung Adenocarcinomas: Whether PKCι expression is elevated in LAC, the most prevalent form of NSCLC, was assessed. Forty primary LAC and matched normal lung tissue samples were initially selected for analysis. Four cases received therapy prior to sample collection and were excluded from the analysis. Immunoblot analysis from five representative cases is shown in FIG. 17A. As was observed with SCCs, PKCι was elevated in LACs when compared to matched normal lung tissue. PKCζ expression was not detected in either normal or cancerous lung tissue, indicating that just as in SCC, PKCι is the major atypical PKC isozyme expressed in LAC tumors.

The vast majority (33/36 or 91.7%) of LACs exhibited elevated PKCι expression, and Spearman rank order statistical analysis demonstrated a significant increase in PKCι polypeptide expression in LAC compared with matched normal lung tissue (FIG. 17B). Immunohistochemical analysis of tissue microarrays made from LAC samples confirmed elevated PKCι staining in epithelial cells within the tumor with little or no immunostaining of surrounding stromal elements (FIG. 17C). Real time PCR analysis revealed no PKCι gene amplification in any of the LAC samples, consistent with the rarity of chromosome 3q26 amplifications in LAC (Petersen et al., *Cancer Res.*, 57, 2331-2335 (1997)). Therefore, elevated PKCι expression is prevalent in both major forms of NSCLC.

PKCι Expression Predicts Poor Survival of Lung Adenocarcinoma Patients: The following was performed to determine whether PKCι polypeptide expression is of prognostic value for the assessment of patients with NSCLC. For this purpose, whether there is a correlation between PKCι expression and either disease stage or cancer-specific death in SCC and LAC was assessed. PKCι expression was determined on a continuous scale and normalized to matched normal lung tissue. In LAC, PKCι polypeptide expression correlated with an increased risk of cancer-specific death. Using Martingale residual analysis, the cases were divided into two groups based on PKCι expression. Patients in the high PKCι expression group were ten times more likely to die from LAC than patients in the low PKCι expression group (risk ratio 10.26, 95% CI 1.68-62.69; p=0.012) (FIG. 17D). Cancer-specific death correlated positively with tumor stage since tumor stage is a reliable predictor of survival in LAC. In this cohort, patients with stage 3 tumors were 3.7 times more likely to die from LAC than were patients with stage 1 or stage 2 tumors (risk ratio 3.65; 95% CI 1.03-12.99; p=0.045). Interestingly, PKCι expression did not correlate with tumor stage, but rather is elevated to a similar degree in tumors at all stages. These data indicate that PKCι expression is an early event during lung carcinogenesis, and may be an important prognostic indicator of cancer-specific death in LAC patients independent of tumor stage. This finding has implications for the use of PKCι expression as a prognostic marker.

In SCC patients, a trend was observed between PKCι expression and cancer-specific death but the correlation did not reach statistical significance (p=0.21). The lack of a statistically significant correlation between PKCι expression and death in SCC may be due to molecular and genetic differences in these two forms of NSCLC. For instance amplification of the PKCι gene and other potential oncogenes present in the chromosome 3q26 amplicon in SCC may obscure a correlation between PKCι expression and clinical outcome. Alternatively, the small sample size analyzed may not have sufficient power to reveal a correlation between these parameters. Indeed, the well-established correlation between tumor grade and death from SCC, while observed in this patient data set, did not reach statistical significance (risk ratio 3.10, p=0.057), indicating that the sample size did not provide sufficient power for the intended analysis. Additional analysis using a larger patient data set can be used to resolve between these possibilities. In conclusion, the results provided herein demonstrate that PKCι plays a role in lung cancer cell transformation. The results that PKCι is dispensable for adherent cell growth and survival indicate that PKCι signaling is an attractive target for the development of new therapeutics for the treatment of lung cancer.

Example 7

Identifying Compounds that Inhibit PKCι Binding PKCι Activity, and Tumorigenicity A primary screen was performed as follows to identify test compound having the potential to inhibit the interaction of PKCι polypeptides with PAR6 polypeptides. Bacterially expressed PKCι$_{1-113}$-YFP-N1 (PYN) was isolated from the soluble fraction of bacterial lysates by affinity purification according to the manufacturer's protocol (B-PER 6×His Purification Kit; Pierce). The purified polypeptide was dialyzed against Tris buffer (50 mM Tris, pH 8.0; 135 mM NaCl; 10% glycerol; 0.002% EDTA) containing 2 M urea. PAR6$_{125}$-CFP-C1 recombinant polypeptide was isolated from the inclusion body pellets of bacterial lysates using the B-PER reagent (Pierce) according to the manufacturer's protocol. The inclusion body pellet was solubilized in Tris buffer containing 8 M urea and dialyzed against the same buffer containing 4 M urea for 4 hours, and then overnight against Tris buffer containing 2 M urea. Yields were measured by fluorescence in a SpectraMax Gemini microplate reader (Molecular Devices).

To perform the assay, PYN was diluted to 4000 relative fluorescent units/50 µl in Tris buffer plus 1 M urea, and PAR6$_{125}$-CFP-C1 was diluted to 400 relative fluorescent units/50 µl Tris buffer plus 1 M urea. To each well of a 96-well, clear-bottom black plate (Costar 3631), 50 µl of PYN and 50 µl of PAR6$_{125}$-CFP-C1 were added, followed by 10 µl of undiluted test compound from the GenPlus library (final concentration of test compound=1 mM). Plates were incubated at 4° C. for about 3-4 hours. Fluorescence was measured in a SpectraMax Gemini plate reader. Cyan fluorescence was measured at excitation 395 nm, emission 475 nm, and cutoff of 455 nm. Yellow fluorescence was measured at excitation 395 nm, emission 529, and cutoff of 515=n. To determine the degree of FRET occurring in the sample, the cyan fluorescence was divided by yellow fluorescence, and compared to samples with only vehicle (DMSO) present.

142 test compounds were identified as being hits with the primary screen (Table 2). These positive hits were from various classes of compounds including flavonoids, dopamine agonist, selenium-containing compounds, etc.

TABLE 2

Test compounds identified as hits.

| Compound Name (identified as a hit in the primary screen) | Chemical Structure | Secondary Screen |
|---|---|---|
| Cianidanol | flavonoid | No effect (related compound hespiridin had no effect) |
| Rutoside | flavonoid | Not tested |
| Quercitin | flavonoid | Not tested |
| Citropten | flavonoid | Not tested |
| 6,4'-dihydroxyflavone | flavonoid | Not tested |
| 6,7-dihydroxyflavone | flavonoid | Not tested |
| 7,2'-dihydroxyflavone | flavonoid | Not tested |
| 7,3'-dihydroxyflavone | flavonoid | Not tested |

TABLE 2-continued

Test compounds identified as hits.

| Compound Name (identified as a hit in the primary screen) | Chemical Structure | Secondary Screen |
|---|---|---|
| 7,4'-dihycroxyflavone | flavonoid | Not tested |
| Naringin | flavonoid | No effect |
| Metergoline | ergot alkaloids | Not tested |
| Dihydroergotamine mesylate | ergot alkaloids | Not tested |
| Ergonovine maleate | ergot alkaloids | Not tested |
| Methylergonovine | ergot alkaloids | No effect |
| Aurothioglucose | gold salt | Confirmed |
| Thimerosal | organic mercury compound | Confirmed |
| Merbromin | organomercurial | Not tested |
| Phenylmercuric acetate | organomercurial | Confirmed |
| Ebselen | novel selenium-containing compound | Confirmed |
| Cisplatin | platinum-containing compound | Confirmed |
| Hydrastinine hydrochloride | isoquinoline alkaloid | Not tested |
| Emetine hydrochloride | isoquinoline alkaloid | Not tested |
| Berberine | isoquinoline alkaloid | Not tested |
| Hydrastine | isoquinoline alkaloid | No effect |
| Amodiaquine | aminoquinolone | No effect |
| Primaquine phosphate | aminoquinolone | No effect |
| Amoxicillin | cillin | Not tested |
| Ampicillin | cillin | Not tested |
| Hetacillin | cillin | Not tested |
| Metampicillin | cillin | Not tested |
| Bacampicillin | cillin | Not tested |
| Methacycline | tetracycline | Not tested |
| Meclocycline | tetracycline | Not tested |
| Doxycycline | tetracycline | No effect |
| Chlortetracycline | tetracycline | Not tested |
| Demeclocycline hydrochloride | tetracycline | Not tested |
| Minocycline hydrochloride | tetracycline | Not tested |
| Oxytetracycline | tetracycline | No effect |
| Tetracycline | tetracycline | Not tested |
| Anthralin | anthraquinone | Not tested |
| Danthron | anthraquinone | Not tested |
| Diacerin | anthraquinone | Not tested |
| Aloin | anthraquinone | Not tested |
| Apomorphine | non-ergoline dopamine agonist | Confirmed |
| R(−)-allylnorapomorphine hydrobromide | non-ergoline dopamine agonist | Not tested |
| Cephradine sodium | cephalosporin | Not tested (related cefadroxil had no effect) |
| cefoxitin | cephalosporin | Not tested |
| Chlorotrianisene | nonsteroidal estrogen | No effect (related compound hexestrol was confirmed) |
| Dantrolene | nitrofuran derivative | Not tested |
| Furazolidone | nitrofuran derivative | No effect |
| Nitrofurantoin | nitrofuran derivative | Not tested |
| Nitrofurazone | nitrofuran derivative | Not tested |
| Imipramine | Phenothiazines | Not tested |
| Propantheline bromide | Phenothiazines | No effect |
| Propiomazine | Phenothiazines | Not tested |
| Trifluoperazine | Phenothiazines | Not tested |
| Flufenazine | Phenothiazines | Not tested |
| Triflupromazine | Phenothiazines | No effect |
| Trazodone hydrochloride | Phenothiazines | Not tested |
| Norepinephrine | adrenergic | Not tested |
| Isoproterenol hydrochloride | adrenergic | No effect |
| Levonordefrin | adrenergic | Not tested |
| Oxidopamine | adrenergic | Not tested |
| Methotrexate | folic acid | Not tested |
| Folic acid | | No effect |
| Reserpine | indolealkylamine alkaloid | Not tested |
| Rescinnamine | indolealkylamine alkaloid | Not tested |
| Estradiol propionate | estrogen | Not tested (related b-estradiol had no effect) |
| Estradiol acetate | estrogen | Not tested |
| Oxolinic acid | quinone | Not tested |

TABLE 2-continued

Test compounds identified as hits.

| Compound Name (identified as a hit in the primary screen) | Chemical Structure | Secondary Screen |
|---|---|---|
| Ofloxacin | quinone | No effect |
| Piroxicam | NSAID - oxicam | Not tested |
| Tenoxicam | NSAID - oxicam | Not tested |
| Citrinin | mycotoxin | Not tested |
| Gentisic acid | aromatic acid | No effect |
| Veratrine sulfate | cevane | No effect |
| Amiloride | diuretic (triamterene) | No effect |
| amphotericin B | polyene | Not tested |
| Amprolium | thiamine analog | No effect |
| Bacitracin | metalloantibiotic | Not tested |
| Benserazide | dopamine agent | Not tested |
| beta-Carotene | carotenoid | Not tested |
| chlorhexidine | bisbiguanide antiseptic | No effect |
| Dipyridamole | pyrimidopyrimidine derivative | Not tested |
| Epinephrine bitartrate | epinephrines | No effect |
| Ergocalciferol | vitamin D | Not tested |
| Gentian violet | triphenylmethane dye | Not tested |
| Hyydroxyzine pamoate | 1st gen histaminergic receptor antagonist | No effect |
| Norfloxacin | 2nd gen quinolones | Not tested (related compounds enoxacin and lomefloxacin had no effect) |
| Phenazopyridine | other | No effect |
| Pyrantel pamoate | tetrahydropyrimidines | Confirmed |
| Pyrvinium pamoate | other | Not tested |
| Quinacrine | acridine derivative | Not tested |
| Roxarsone | arsenic compound | Not tested |
| Sulfasalazine | other | Not tested |
| Sulindac | NSAID - indomethacin | No effect |
| Triamterene | other | Not tested |
| Tyrothricin | mixture of tyrocidins/gramicidins | Not tested |
| Acriflavinium hydrochloride | other | No effect |
| Bergaptene | furocoumarin | Not tested |
| Rosolic acid | other | No effect |
| Calcein | fluorescein-iminodiacetic complex | Not tested |
| Glafenine | anthranilic acid derivative | No effect |
| Ethoxyquin | quinoline fungicide | Not tested |
| Fenbendazole | benzimidazole | Not tested |
| Pimozide | dopamine antagonist | Not tested (related compound droperidol had no effect) |
| Acecainide hydrochloride | other | Not tested |
| Erythromycin propionate lauryl sulfate | macrolide antibiotic | No effect |
| Benzamil hydrochloride | amiloride derivative | Not tested |
| 9-amino-1,2,3,4-tetrahydroacridine hydrochloride | acridine derivative | Not tested |
| Piromidic acid | Pyridopyrimidines; pyrrolidines; quinolones | Not tested |
| Alrestatin | quinazoline acetic acid derivatives | Not tested |
| N-carboxyheptylimidazole hydrochloride | other | Not tested |
| Anthracene-9-carboxylic acid | anthracene | Not tested |
| Gossypol-acetic acid complex | other | Confirmed |
| alpha-cyano-4-hydroxycinnamic acid | other | Not tested |
| 2-phenpropylamino-5-nitrobenzoic acid | other | Not tested |
| Ellagic acid | tannin; polyphenolic | Confirmed |
| Aclarubicin | anthracycline | Not tested |
| Alexidine | bisbiguanide antiseptic | Not tested |
| Tretinon | retinoic acid | No effect |
| Cetrimonium bromide | polycationic antiseptic | Not tested |
| Pararosaniline pamoate | other | Not tested |
| Nimesulide | sulfoanilide | Not tested |
| Lupitidine hydrochloride | other | Not tested |

TABLE 2-continued

Test compounds identified as hits.

| Compound Name (identified as a hit in the primary screen) | Chemical Structure | Secondary Screen |
|---|---|---|
| Methazolamide | carbonic anhydrase inhibitor | No effect |
| 3,5-dinitrocatechol | catechol derivative | Not tested |
| Thiram | pesticide | Not tested |
| Tetroquinone | polyhydroxylated aromatic compound | Not tested |
| Monensin, sodium | ionophore antibiotic | No effect |
| Dequalinium chloride | lipophilic cationic compound | No effect |
| Antimycin A | other | No effect |
| Mycophenolic acid | other | No effect |
| 3-hydroxymethyl-b-carboline | beta carboline alkaloid | Not tested |
| Etiocholanolone | androgen | No effect |
| Lapachol | naphtoquinone | Not tested |
| Benzalkonium chloride | quatenary ammonium compound | No effect |
| Trioxsalen | furocoumarin | Not tested (related compound 8-methoxypsoralen) |
| Prazosin | cationic drug | No effect |
| 4-naphthalimidobutyric acid | other | Not tested |
| Metolazone | chemically related to thiazides | Not tested (related compound bendroflumethiazide had no effect) |
| NPPB | other | Not tested |

Multiple test compounds that were classified as hits in the primary screen as well as additional related compounds were evaluated in a secondary screen designed as follows. Briefly, a 96-well microtiter plate coated with streptavidin (Nunc #436014) was incubated for 2-4 hours at room temperature with 100 μl of a 20-30 μg/ml solution of biotin-tagged PAR6 (whole polypeptide) in phosphate-buffered saline containing Tween-20 (PBST). Plates were washed twice with PBST, then once with incubation buffer (50 mM Tris, pH 8.0; 135 mM NaCl; 10% glycerol; 0.002% EDTA). Incubation buffer (50 μl) was added to each well. The compounds to be tested were added (10 μl) followed by PYN (50 μl) diluted in incubation buffer to an approximate concentration of 4000-5000 relative fluorescent units per 50 μl. Plates were incubated overnight at 4° C. Plates were washed twice with incubation buffer, after which 50 μl incubation buffer was added to retain moisture in the wells. The amount of PYN bound on the plates was determined by measuring yellow fluorescence (532/526) in a Typhoon imager. Fluorescence was quantitated by Softmax Pro software.

The following test compounds were confirmed via the secondary screen as having the potential to inhibit the interaction of PKCι polypeptides with PAR6 polypeptides: aurothioglucose, thimerosal, phenylmercuric acetate, ebselen, cisplatin, apomorphine, pyrantel pamoate, gossypol-acetic acid complex, ellagic acid, and hexestrol. A dose-response analysis was performed using the secondary screening assay and increasing amounts (e.g., 0, 0.1, 1, 10, 100, and 100 μM) of gossypol, hexestrol, thimerosal, ebselen, ATG, ATM, ellagic acid, cisplatin, apomorphine, or phenylmercuric acetate. In each case, a dose-dependent response was detected as the dose increased.

Figure 18:
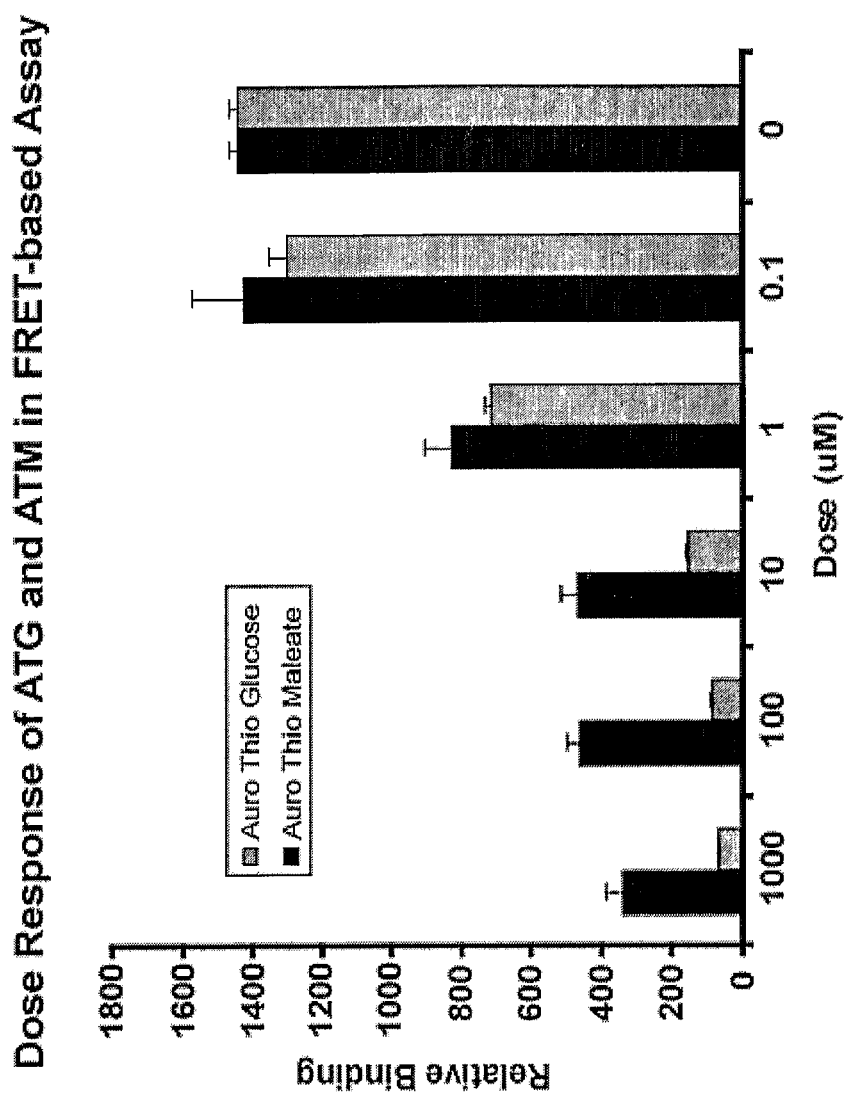
FIG. 18 is a bar graph plotting the dose response of ATG and ATM in a FRET-based assay designed to assess the interaction between PAR6 and PCKι polypeptides.

A dose-response analysis was performed using aurothioglucose (ATG) and aurothiomaleate (ATM) in the FRET assay that was used as the primary screen. Both compounds exhibited a dose-dependent effect on relative binding of PKCι and PAR6 polypeptides with less binding being observed as the ATG or ATM concentrations increased (FIG. 18).

Rac 1 Activity Assays: A549 cells were incubated with the indicated concentration of ATG for one hour prior to analysis. Rac1 activity in A549 cells was assessed by affinity isolation of GTP-bound Rac1 using binding domains of PAK as described elsewhere (Sander et al., *J. Cell Biol.*, 143:1385-98 (1998)). Briefly, cells were lysed in lysis buffer (50 mM Tris-HCl pH 7.5, 150 mM NaCl, 20 mM $MgCl_2$, 5 mM EGTA, 10% glycerol, 1% Triton X-100, 1% NP-40, 25 mM NaF, 1 mM phenylmethylsulfonyl fluoride, 1 mM sodium orthovanadate, 10 μg/ml leupeptin, and 10 μg/ml aprotinin) at 4° C. for 5 min. Cellular debris was removed by centrifugation at 20,000×g for 5 min, and supernatants were transferred to new tubes containing 20 μl of GST-p21-binding domain of PAK1 (PAK1-PBD) coupled to agarose beads (Upstate). An aliquot of each supernatant was reserved to determine total Rac1 and actin expression by immunoblot analysis. Following a 30 minute incubation at 4° C., the agarose beads were collected by centrifugation and washed three times in wash buffer (50 mM Tris-HCl pH 7.5, 150 mM NaCl, 20 mM $MgCl_2$, 5 mM EGTA, 10% glycerol, 1% Triton X-100, 1% NP-40, 25 mM NaF, 1 mM phenylmethylsulfonyl fluoride, 1 mM sodium orthovanadate, 10 μg/ml leupeptin, and 10 μg/ml aprotinin). Bound polypeptides were solubilized by the addition of 30 μl of SDS sample buffer, resolved by SDS-PAGE, and subjected to immunoblot analysis for Rac1.

Figure 19:
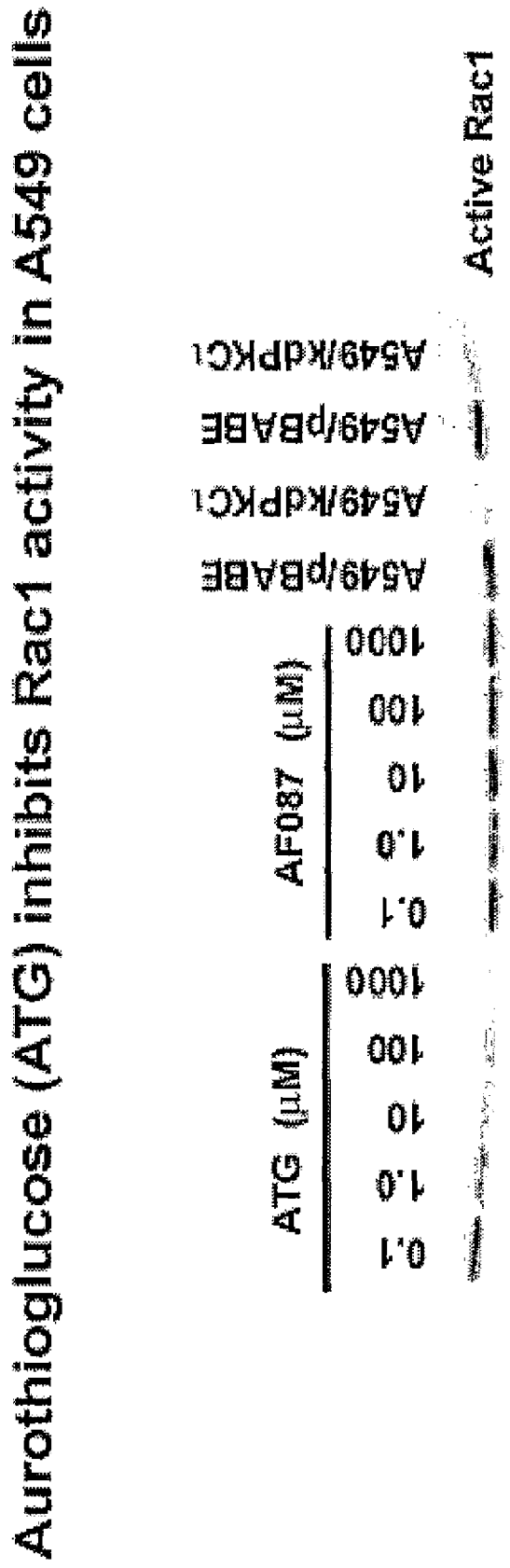
FIG. 19 contains a photograph of an immunoblot analysis of Rac1 activity in cells treated with ATG.

Treatment of cells with ATG resulted in decreased Rac1 activity (FIG. 19). In addition, ATG exhibited a dose-dependent effect on Rac1 activity with less Rac1 activity being observed as the ATG concentrations increased.

Soft Agar Growth Assays: Anchorage-independent growth was assayed by the ability of cells to form colonies in soft agar. The bottom agar consisted of growth medium containing 10% FBS and 0.75% agarose in 60-mm tissue culture dishes. Nine hundred cells were resuspended in growth medium containing 10% FBS and 0.75% agarose and plated on top of the bottom agar. ATG was added at the indicated concentration to both bottom and top agar solutions. The cells were incubated at 37° C. in 5% $CO_2$. Cell colonies were visualized and quantified under a dissecting microscope (Olympus) after 4-6 weeks in culture.

Figure 20:
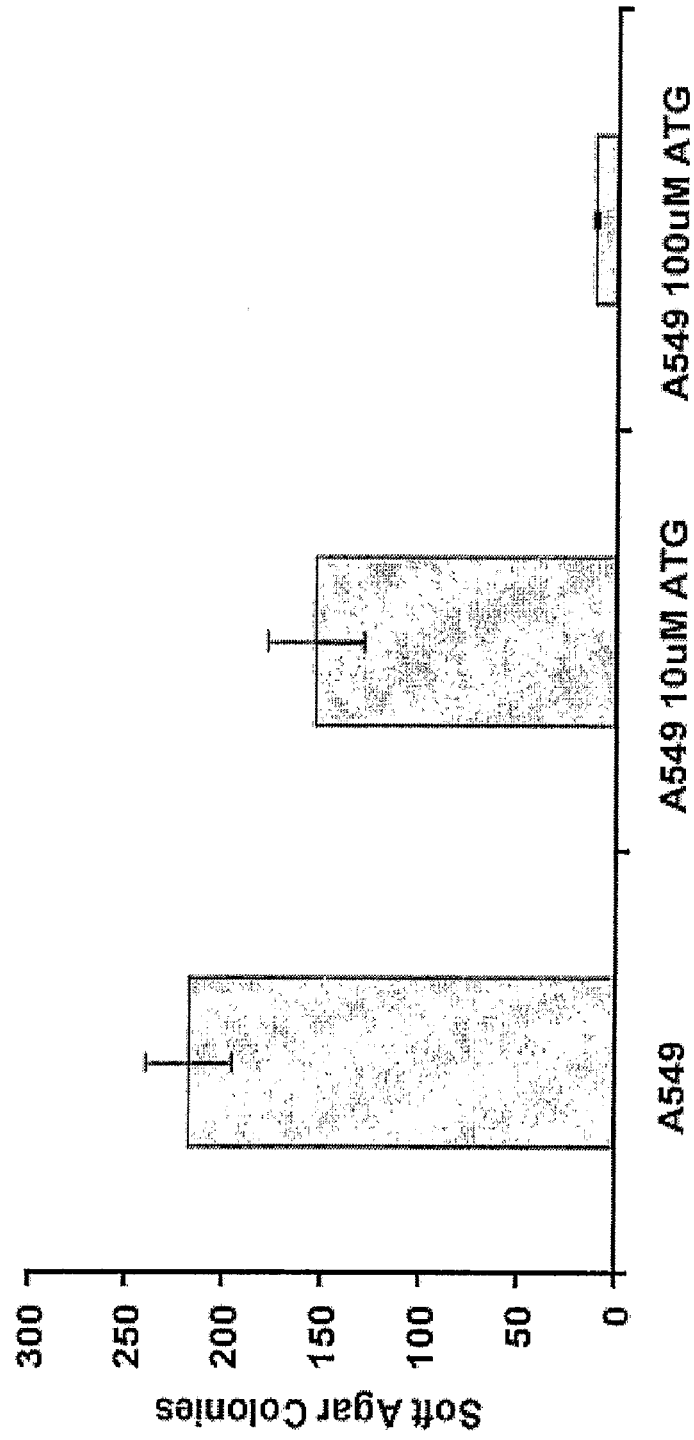
FIG. 20 is a bar graph plotting the number of colonies formed by anchorage-independent growth of A549 cells in soft agar. The cells were either untreated or treated with ATG (10 μM or 100 μM).

Treatments with 10 μM and 100 μM of ATG resulted in decreased soft agar growth (FIG. 20).

Tumorigenicity in Nude Mice: The growth of A549 human lung carcinoma cells as established subcutaneous tumors was studied in athymic nude mice (Harlan-Sprague-Dawley, Indianapolis, Ind.) in a defined pathogen-free environment. Briefly, A549 cells were grown in F-12K Nutrient Mixture containing 10% FBS. A549 cells were harvested and resuspended in serum-containing medium. $5 \times 10^6$ cells in 100 μl of growth medium were injected subcutaneously into the flank of 4-6 week old female nude mice. Once palpable tumors were established (15 days after inoculation) animals were randomly segregated into two groups. One group received intraperitoneal injections of ATG (200 mg/kg body weight) daily; the second group received an equivalent volume of diluent control solution. Tumor size was measured daily. Tumor growth was quantified by measuring the tumors in three dimensions with calipers. Tumor volume ($mm^3$) was calculated using the formula: 0.5236 (L×W×H), where L represents the length of the tumor, W represents the width of the tumor, and H represents the height of the tumor. Animals were individually monitored throughout the experiment.

Figure 21:
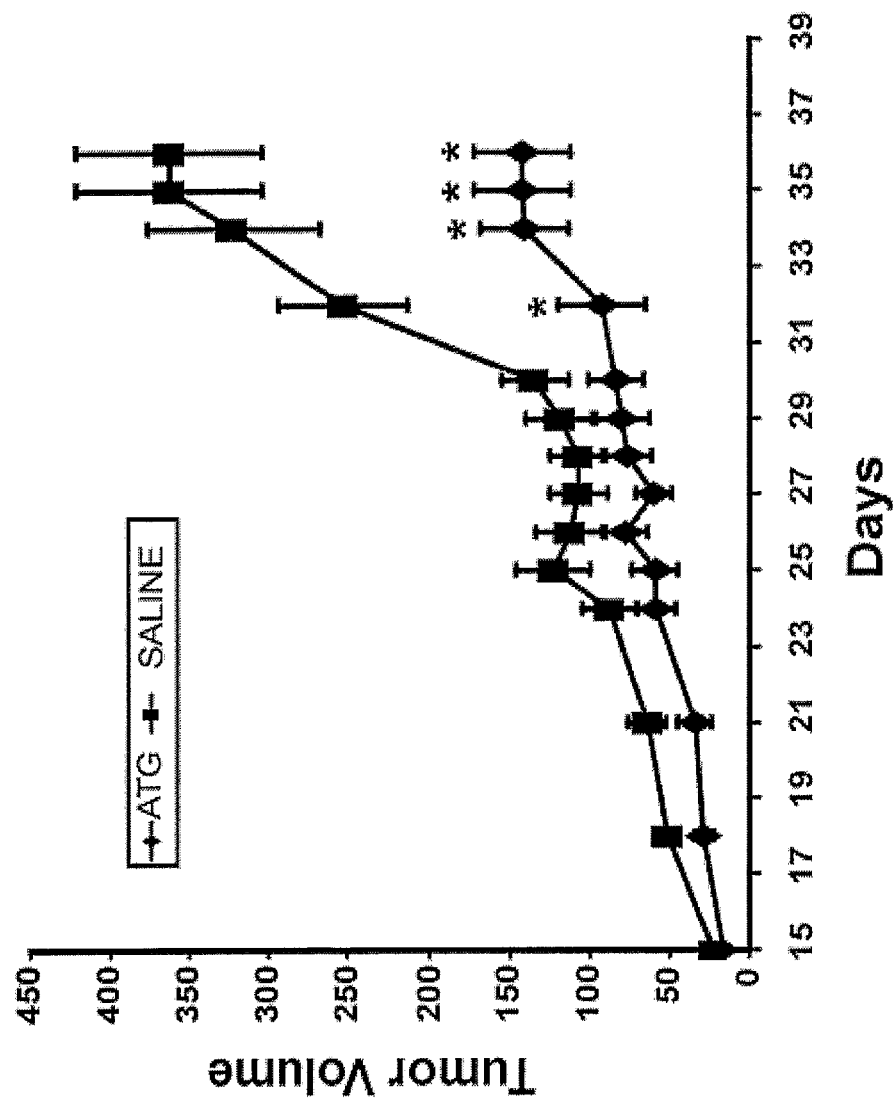
FIG. 21 is a graph plotting tumor volume for mice treated with saline or ATG.

Animals treated with ATG exhibited less tumor growth than the tumor growth exhibited in animals treated with saline (FIG. 21). These results demonstrate that test compound identified using the methods and materials provided herein can be used to inhibit PKCι activity and reduce, for example, tumor growth.

Example 8

Animal Model of Lung Cancer

A tetracycline-based bitransgenic, regulatable expression system has been used to create conditional expression of transgenes specifically in the lung epithelium. Transgenic mice expressing reverse tet transactivator (rtTA) from either the surfactant protein C(SP-C) or Clara Cell Specific Protein (CCSP) promoter allow conditional expression of tet-responsive gene constructs in the lung epithelium. When SP-C-rtTA (or CCSP-rtTA) mice are crossed to transgenic mice expressing a (tetO)7-CMV-transgene, expression of the transgene can be targeted to the lung epithelium under the control of doxycycline. This system has been used to establish the role of oncogenic K-Ras mutations in LAC development and maintenance (Fisher et al., *Genes Dev.*, 15:3249-3262 (2001)). Crossing CCSP-rtTA mice to transgenic mice expressing (tetO)7-CMV-K-RasG12D, generated mice in which oncogenic K-Ras can be conditionally expressed in the lung epithelium by addition of doxycycline to the drinking water. CCSP-rtTA/(tetO)7-K-RasG12D bitransgenic mice develop multiple LACs only after administration of doxycycline. Interestingly, when doxycycline is withdrawn, tumors rapidly regress due to massive apoptosis, showing that K-RasG12D is necessary for both tumor establishment and maintenance.

Bitransgenic mice were developed to allow conditional expression of kdPKCι in the lung epithelium under the control of doxycycline. To construct this model, transgenic SP-C-rtTA "inducer" mice expressing the reverse tetracycline transactivator protein (rtTA) specifically in the lung epithelium under the control of the SP-C promoter were obtained. In addition, transgenic "responder" mice expressing kdPKCι under the control of a tet responsive promoter, tet(07)-CMV were generated. These mice exhibit germline transmission of a tet(O7)-CMV-FLAG-kdPKCι transgene designed to support tet-regulated expression of FLAG-kdPKCι. Three independent transgenic tet(O7)-CMV-FLAG-kdPKCι mouse lines were established. One of these lines was crossed to SP-C-rtTA mice to establish bitransgenic SPC-rtTA/tet-kdPKCι mice. When bitransgenic SPC-rtTA/tet-kdPKCι mice are given doxycycline in their drinking water, they exhibit tet-regulated expression of FLAG-kdPKCι mRNA in the lung epithelium as determined by QRT-PCR. The kdPKCι transgene was not detected in other tissues (liver, thymus, colon or kidney), indicating that conditional expression is specific to the lung.

Similar mice can be made to express wild-type PKCι polypeptides or caPKCι polypeptides instead of kdPKCι polypeptides.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic mouse whose genome comprises a transgene, said transgene comprising a nucleic acid sequence encoding a constitutively active protein kinase C iota polypeptide operably linked to a liver fatty acid-binding protein promoter, wherein said transgenic mouse expresses said constitutively active protein kinase C iota polypeptide and develops more preneoplastic colonic lesions after azoxymethane treatment than a corresponding wild-type mouse treated with said azoxymethane.

2. The transgenic mouse of claim 1, wherein the promoter is an $Fabpl^{4 \times at -132}$ promoter.

3. Progeny of the transgenic mouse of claim 1, wherein the progeny have a genome comprising the transgene, and wherein said progeny expresses said constitutively active protein kinase C iota polypeptide and develop more preneoplastic colonic lesions after azoxymethane treatment than a corresponding wild-type mouse treated with said azoxymethane.

4. An isolated cell of a transgenic mouse whose genome comprises a transgene, said transgene comprising a nucleic acid sequence encoding a constitutively active protein kinase C iota polypeptide operably linked to a liver fatty acid-binding protein promoter, wherein said transgenic mouse expresses said constitutively active protein kinase C iota polypeptide and develops more preneoplastic colonic lesions after azoxymethane treatment than a corresponding wild-type mouse treated with said azoxymethane.

5. A method for identifying an agent that inhibits transformation of a cell, wherein said method comprises: (a) administering a test agent and carcinogen to transgenic mouse whose genome comprises a transgene, said transgene comprising a nucleic acid sequence encoding a constitutively active protein kinase C iota polypeptide operably linked to a liver fatty acid-binding protein promoter, wherein said transgenic mouse expresses said constitutively active protein kinase C iota polypeptide and develops more preneoplastic colonic lesions after azoxymethane treatment than a corresponding wild-type mouse treated with said azoxymethane, and (b) determining if said test agent inhibits cell transformation in said transgenic mouse as compared with a corresponding transgenic mouse to which said test agent has not been administered.

6. The method of claim 5, comprising determining if said test agent inhibits intestinal cell transformation in said transgenic mouse as compared with a corresponding transgenic mouse to which said test agent has not been administered.

7. The method of claim 5, wherein said test agent is a test polypeptide.

8. The method of claim 7, wherein said test polypeptide comprises an amino acid sequence present in a protein kinase C iota polypeptide.

9. The method of claim 5, wherein said carcinogen is azoxymethane or dimethylhydrazine.

* * * * *

UNITED STATES PATENT AND TRADEMARK OFFICE
CERTIFICATE OF CORRECTION

| | | |
|---|---|---|
| PATENT NO. | : 7,642,400 B2 | |
| APPLICATION NO. | : 10/592289 | |
| DATED | : January 5, 2010 | |
| INVENTOR(S) | : Fields et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 147 days.

Signed and Sealed this
Thirty-first Day of May, 2011

David J. Kappos
*Director of the United States Patent and Trademark Office*